United States Patent [19]

Senter et al.

[11] Patent Number: 4,975,278
[45] Date of Patent: Dec. 4, 1990

[54] ANTIBODY-ENZYME CONJUGATES IN COMBINATION WITH PRODRUGS FOR THE DELIVERY OF CYTOTOXIC AGENTS TO TUMOR CELLS

[75] Inventors: Peter D. Senter, Seattle, Wash.; Mark G. Saulnier, Middletown, Conn.; Joseph P. Brown; David E. Kerr, both of Seattle, Wash.

[73] Assignee: Bristol-Myers Company, New York, N.Y.

[21] Appl. No.: 211,301

[22] Filed: Jun. 29, 1988

Related U.S. Application Data

[63] Continuation-in-part of Ser. No. 161,068, Feb. 26, 1988, abandoned, which is a continuation-in-part of Ser. No. 81,382, Aug. 4, 1987, abandoned.

[51] Int. Cl.$^5$ .................. A61K 37/48; A61K 39/395; C12N 11/16; C12N 9/96
[52] U.S. Cl. ................... 424/94.3; 424/85.91; 424/94.1; 424/94.6; 514/27; 514/33; 514/34; 514/80; 530/387; 530/389; 530/391; 435/188; 435/196; 435/200; 435/212; 435/219; 536/64; 536/18.1
[58] Field of Search .................. 536/6.4, 18.1; 514/34, 514/80, 27, 33; 424/85.91, 94.1, 94.3, 94.6; 530/387, 389, 391; 435/68, 188, 196, 212, 219, 200

[56] References Cited

U.S. PATENT DOCUMENTS

| | | | |
|---|---|---|---|
| 4,185,111 | 1/1980 | Ducep et al. | 424/283 |
| 4,564,675 | 1/1986 | Kurabayashi et al. | 536/18.1 |
| 4,675,187 | 6/1987 | Konishi et al. | 424/117 |
| 4,762,707 | 8/1988 | Jansen et al. | 424/85.91 |

FOREIGN PATENT DOCUMENTS

| | | | |
|---|---|---|---|
| 1216791 | 1/1987 | Canada . | |
| 0142905 | 5/1985 | European Pat. Off. . | |
| 287353 | 10/1988 | European Pat. Off. | 536/6.4 |
| 3192793 | 8/1988 | Japan | 536/18.1 |
| WO87/03205 | 6/1987 | PCT Int'l Appl. . | |

OTHER PUBLICATIONS

Hellstrom et al., Cancer Research, 46, (Aug. 1986), 3917–3923.
Philpott et al., Cancer Research, 34, (1974), 2159–2164.
Hellstrom et al., J. Immunol., 127(1), (1981), 157–160.
Stella et al., in *Directed Drug Delivery*, (1985), pp. 247–267.
Nishiyama et al., Cancer Research, 45, (1985), 1753–1761.

(List continued on next page.)

*Primary Examiner*—Jacqueline Stone
*Attorney, Agent, or Firm*—Deborah J. Barnett

[57] ABSTRACT

This invention relates to a novel method for the delivery of cytotoxic drugs to tumor cells by the administration of a tumor-specific antibody-enzyme conjugate that binds to the tumor cells, and the additional administration of a prodrug that is converted at the tumor site, in the presence of the antibody-bound enzyme, to an active cytotoxic drug. According to preferred embodiments of this invention, antibody-enzyme conjugates containing the enzyme, alkaline phosphatase ("AP"), have been used in conjunction with the novel prodrug, etoposide-4'-phosphate or 7-(2'-aminoethyl phosphate)-mitomycin or a combination thereof, to effect killing of tumor cells. According to another embodiment of the invention, an antibody-enzyme conjugate containing the enzyme, penicillin V amidase ("PVA"), has been used in conjunction with a novel prodrug, N-(p-hydroxyphenoxyacetyl)adriamycin to effect killing of tumor cells. Still another embodiment of the invention relates to the use of an antibody-enzyme conjugate containing the enzyme, cytosine deaminase ("CD"), in combination with the prodrug, 5-fluorocytosine, to effect killing of tumor cells. The method, antibody-enzyme conjugates, prodrugs, pharmaceutical compositions and combinations of this invention provide for enhanced selective killing of tumor cells and are thus useful in the treatment of cancers and other tumors.

64 Claims, 28 Drawing Sheets

OTHER PUBLICATIONS

Wilman, Biochem. Soc. Trans., 14, (615th Meeting, Belfast, 1986), 375–382.

O'Dwyer et al., N. Eng. J. Med., 312, (1985), 692–700.

A. P. Albino et al., "Heterogeneity in Surface Antigen and Glycoprotein Expression of Cell Lines Derived from Different Melanoma Metastases of the Same Patient", J. Exp. Med., 154, pp. 1764–1778, (1981).

R. Arnon et al., "In Vitro and In Vivo Efficacy of Conjugates of Daunomycin with Anti-Tumor Antibodies", Immunological Rev., 62, pp. 5–27, (1982).

K. D. Bagshawe, "Antibody Directed Enzymes Revive Anti-Cancer Prodrugs Concept", Br. J. Cancer, 56, (No. 5), pp. 531–532, (Nov. 1987), (Bagshawe I).

K. D. Bagshawe et al., "A Novel Approach to Prodrug Activation Using a Monoclonal Antibody Conjugated to Carboxypeptidase $G_2$", from the Third International Conference on Monoclonal Antibody Immunoconjugates for Cancer, Abstract #43, p. 70, (San Diego, Feb. 4–6, 1988) (Bagshawe II).

R. W. Baldwin et al., "Design and Therapeutic Evaluation of Monoclonal Antibody 791T/36-Methotrexate Conjugates", in Monoclonal Antibodies and Cancer Therapy, pp. 215–231, (Alan R. Liss, Inc., 1985), (Baldwin I).

R. W. Baldwin et al., "Monoclonal Antibodies in Cancer Treatment", Lancet, pp. 603–605, (Mar. 15, 1986), (Baldwin II).

R. W. Baldwin et al., "Monoclonal Antibody Drug Conjugates for Cancer Therapy", in Monoclonal Antibodies in Cancer: Advances in Diagnosis and Treatment, Jack A. Roth (ed.)., pp. 215–257, (Futura Publishing Co., 1986), (Baldwin III).

J. P. Brown et al., "Structural Characterization of Human Melanoma-Associated Antigen p97 with Monoclonal Antibodies", J. Immunol., 127, (No. 2), pp. 539–546, (1981).

E. A. Clark et al., "Role of the Bp35 Cell Surface Polypeptide in Human B-Cell Activation", Proc. Natl. Acad. Sci., 82, pp. 1766–1770, (1985).

S. T. Crooke et al. (eds.), Antiracyclines: Current Status and New Developments, Academic Press, (New York, 1980).

R. A. DeWeger et al., "Eradication of Murine Lymphoma and Melanoma Cells by Chlorambucil-Antibody Complexes", Immunological Rev., 62, pp. 29–45, (1982).

M. J. Embleton et al., "Antibody Targeting of Anti-Cancer Agents", in Monoclonal Antibodies for Cancer Detection and Therapy, R. W. Baldwin and V. S. Byers (eds.), pp. 321–322, (Academic Press, 1985), (Embleton I).

M. J. Embleton, "Targeting of Anti-Cancer Therapeutic Agents by Monoclonal Antibodies", Biochemical Society Transactions, 14, pp. 393–395, (615th Meeting, Belfast, 1986), (Embleton II).

N. Endo et al., "In Vitro Cytotoxicity of a Human Serum Albumin-Mediated Conjugate of Methotrexate with Anti-MM46 Monoclonal Antibody", Cancer Research, 47, pp. 1076–1080, (Feb. 1987).

P. J. Fraker et al., "Protein and Cell Membrane Iodinations with a Sparingly Soluble Chloroamide, 1,3,4,6-Tetrachloro-3a,6a-Diphenylglycoluril", Biochem. Biophys. Res. Commun., 80, (No. 4), pp. 849–857, (1978).

I. Hellstrom et al., "Antitumor Effect of L6, an $IgG_{2a}$ Antibody that Reacts with Most Human Carcinomas", Proc. Natl. Acad. Sci. U.S.A., 83, pp. 7059–7063, (1986).

I. Hellstrom et al., "Antibodies for Drug Delivery", in Controlled Drug Delivery, (2nd ed.), Robinson and Lee (eds.), p. 639, (1987), (Hellstrom IV).

P. L. Ipata et al., "Baker's Yeast Cytosine Deaminase. Some Enzymatic Properties and Allosteric Inhibition by Nucleosides and Nucleotides", Biochemistry, 10, pp. 4270–4276, (1971).

T. Katsuragi et al., "Affinity Chromatography of Cytosine Deaminase from Escherichia coli with Immobilized Pyrimidine Compounds", Agric. Biol. Chem., 50, (No. 7), pp. 1713–1719, (1986).

J. M. Lambert et al., "Purified Immunotoxins That Are Reactive with Human Lymphoid Cells", J. Biol. Chem., 260, (No. 22), pp. 12035–12041, (1985).

J. P. Mach et al., "Improvement of Colon Carcinoma Imaging: from Polyclonal Anti-CEA Antibodies and Static Photoscanning to Monoclonal Fab Fragments and ECT", in Monoclonal Antibodies for Cancer Detection and Therapy, R. W. Baldwin et al. (eds.), pp. 53–64, (Academic Press, 1985).

R. B. McComb et al. (eds.), Alkaline Phosphatase, Plenum Press, (New York, 1979).

R. G. Melton et al., "In Vivo Localization of Carboxypeptidase $G_2$: Antibody Conjugates in Human Colon (List continued on next page.)

OTHER PUBLICATIONS

Carcinoma Xenografts", from the Third International Conference on Monoclonal Antibody Immunoconjugates for Cancer, Abstract #83, p. 110, (San Diego, Feb. 4-6, 1988).

S. Monfardini et al. (eds), *Manual of Cancer Chemotherapy*, (3rd ed.), UICC Technical Report Series, vol. 56, (Geneva, 1981).

F. L. Moolten et al., "Antibodies Conjugated to Potent Cytotoxins as Specific Antitumor Agents", *Immunological Rev.*, 62, pp. 47-73, (1982).

K. Ohkawa et al., "Selective In Vitro and In Vivo Growth Inhibition Against Human Yolk Sac Tumor Cell Lines by Purified Antibody Against Human α-Fetoprotein Conjugated with Mitomycin C via Human Serum Albumin", *Cancer Immunol. Immunother.*, 23, pp. 81-86, (1986).

C. W. Parker et al., "Enzymatic Activation and Trapping of Luminol-Substituted Peptides and Proteins. A Possible Means of Amplifying the Cytotoxicity of Anti-Tumor Antibodies", *Proc. Natl. Acad. Sci. U.S.A.*, 72, (No. 1), 338-342, (1975).

G. W. Philipott et al., "Selective Iodination and Cytotoxicity of Tumor Cells with an Antibody-Enzyme Conjugate", *Surgery*, 74, pp. 51-58, (1973), (Philpott I).

G. W. Philpott et al., "Selective Cytotoxicity of Hapten-Substituted Cells with an Antibody-Enzyme Conjugate", *J. Immunol.*, 111, (No. 3), pp. 921-929, (1973), (Philpott II).

M. J. Robins et al., "Nucleic Acid Related Compounds. 16. Direct Fluorination of Uracil Nucleotides Using Trifluoromethyl Hypofluorite", *Can. J. Chem.*, 53, pp. 1302-1306, (1975).

G. F. Rowland et al., "Drug Localization and Growth Inhibition Studies of Vindesine-Monoclonal Anti-CEA Conjugates in a Human Tumour Xenograft", *Cancer Immunol. Immunother.*, 21, pp. 183-187, (1986).

F. Searle et al., "Antibody Carboxypeptidase $G_2$ Conjugates as Anti-Tumor Agent", *Tumor Biology*, 6, (No. 4), p. 355, (1985), (Searle I).

F. Searle et al., "Carboxypeptidase $G_2$ Conjugates with Localizing Anti-Tumour Antibodies: Potential Therapeutic Agents", *Tumor Biology*, 7, (No. 4), p. 320, (1986), (Searle II).

F. Searle et al., "The Potential of Carboxypeptides $G_2$-Antibody Conjugates as Anti-Tumour Agents. I. Preparation of Antihuman Chorionic Gonadotrophin-Carboxypeptidase $G_2$ and Cytotoxicity of the Conjugate Against JAR Choriocarcinoma Cells In Vitro", *Br. J. Cancer*, 53, pp. 377-384, (1986), (Searle III).

W. T. Shearer et al., "Cytotoxicity with Antibody-Glucose Oxidase Conjugates Specific for a Human Colonic Cancer and Carcinoembryonic Antigen", *Int. J. Cancer*, 14, pp. 539-547, (1974).

V. J. Stella et al., "Prodrugs: Do They Have Advantages in Clinical Practice?", *Drugs*, 29, pp. 455-473, (1985), (Stella I).

W. A. Thomas, "Prodrugs", *Biochemical Society Tranactions*, 14, pp. 383-387, (615th Meeting, Belfast, 1986).

P. E. Thorpe et al., "The Preparation and Cytotoxic Properties of Antibody-Toxin Conjugates", *Immunological Rev.*, 62, pp. 119-158, (1982), (Thorpe I).

P. E. Thorpe, "Antibody Carriers of Cytotoxic Agents in Cancer Therapy: A Review", in *Monoclonal Antibodies '84: Biological and Clinical Applications*, A. Pinchera et al., (eds.), pp. 475-506, (1985), (Thorpe II).

E. S. Vitetta et al., "Redesigning Nature's Poisons to Create Anti-Tumor Reagents", *Science*, 238, pp. 1098-1104, (1987).

M. Y. Yeh et al., "Cell Surface Antigens of Human Melanoma Identified by Monoclonal Antibody", *Proc. Natl. Acad. Sci.*, 76, (No. 6), pp. 2927-2931, (1979), (Yeh I).

M. Y. Yeh et al., "Clonal Variation in Expression of a Human Melanoma Antigen Defined by a Monoclonal Antibody", *J. Immunol.*, 126, (No. 4), pp. 1312-1317, (1981), (Yeh II).

ANTIBODY-ENZYME CONJUGATE BINDS TO CELL POPULATION

ENZYME CONVERTS PRODRUG INTO ACTIVE DRUG

DRUG (d) ENTERS CELLS RESULTING IN CELL DEATH

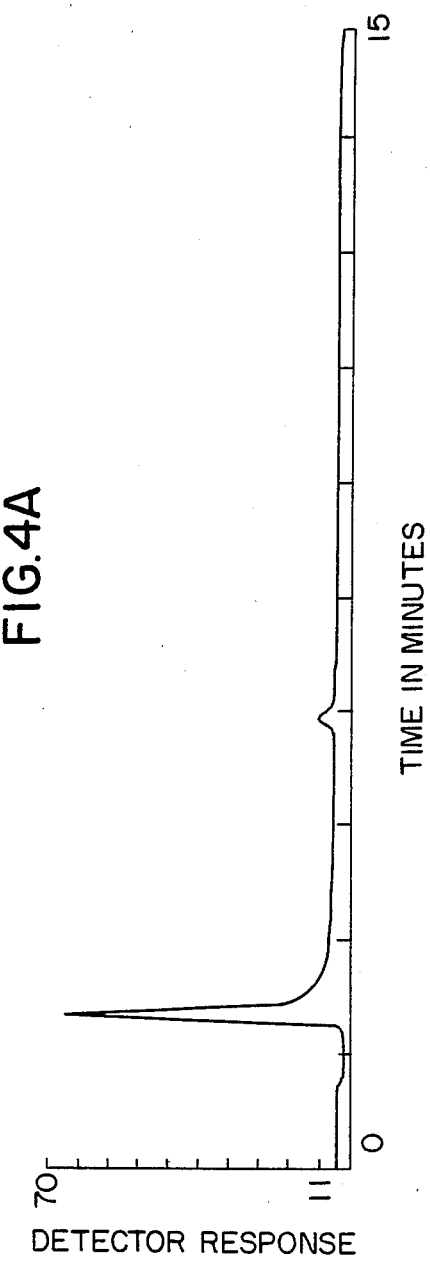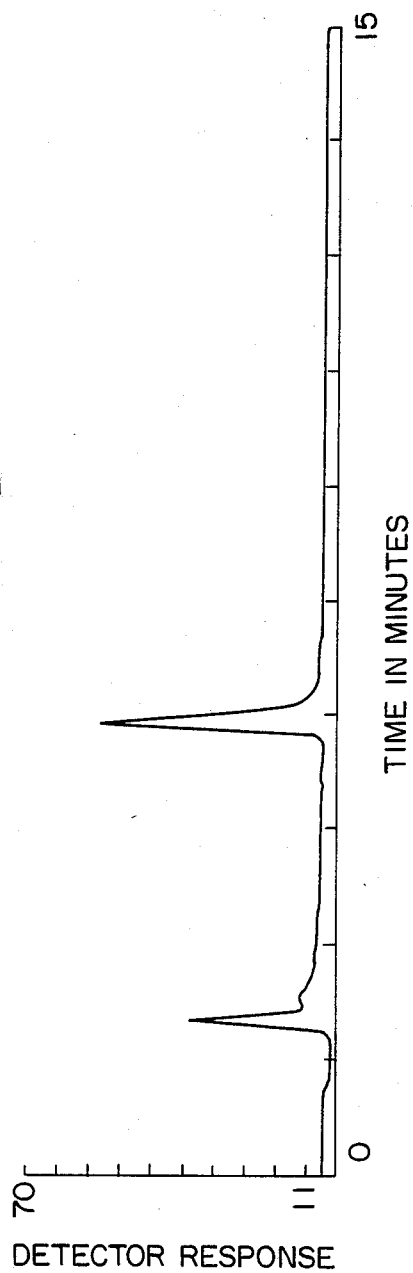

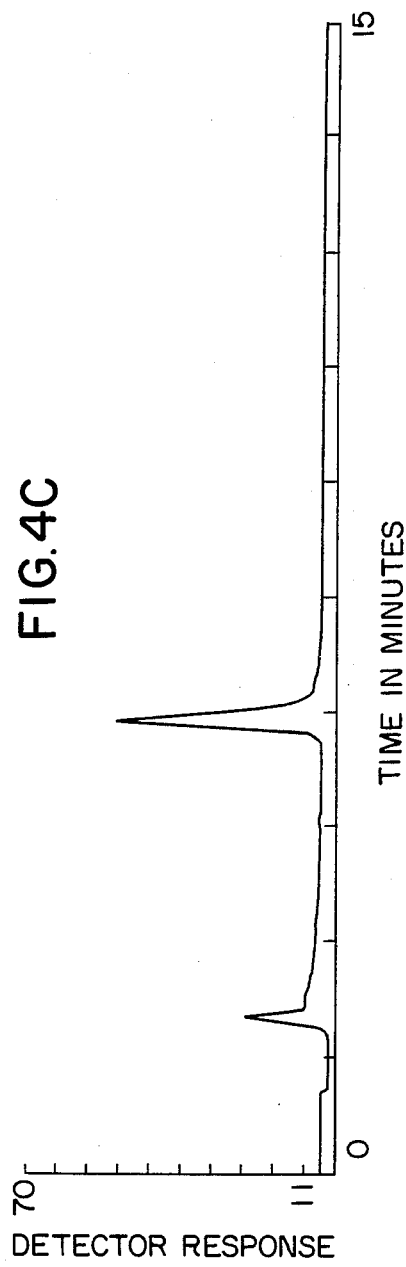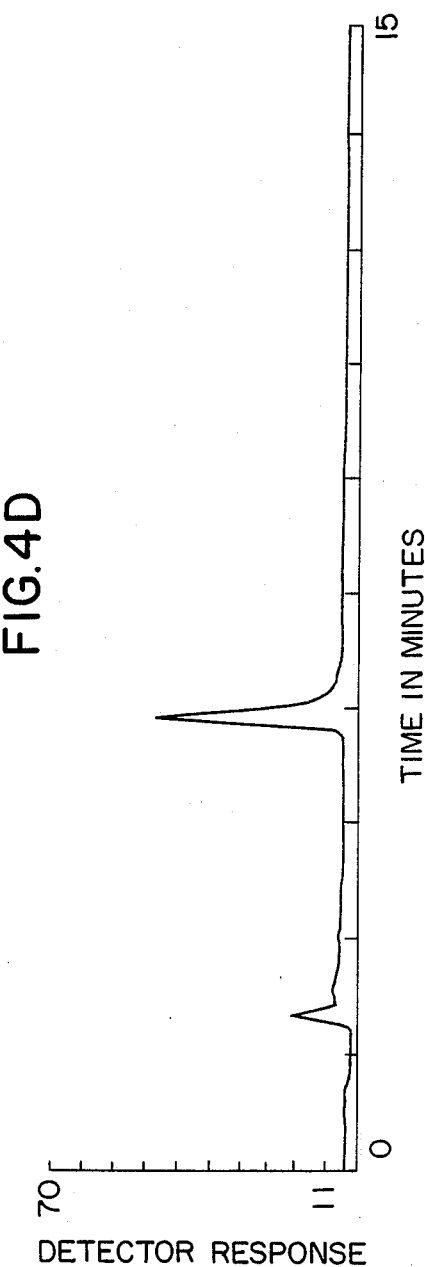

R = NH$_2$  (MMC)

R = HOCH$_2$CH$_2$NH—  (MOH)

R = Na$_2$O$_3$POCH$_2$CH$_2$NH—  (MOP)

ANTIBODY-ENZYME CONJUGATES IN COMBINATION WITH PRODRUGS FOR THE DELIVERY OF CYTOTOXIC AGENTS TO TUMOR CELLS

This application is a continuation-in-part of U.S. patent application, Ser. No. 161,068, filed on Feb. 26, 1988 in the United States Patent and Trademark Office, which application is a continuation-in-part of U.S. patent application, Ser. No. 081,382, filed on Aug. 4, 1987, both now abandoned.

TECHNICAL FIELD OF THE INVENTION

The present invention relates to a novel method for the delivery of cytotoxic agents to tumor cells by the combined use of antibody-enzyme conjugates and prodrugs. More particularly, this invention relates to a method for the delivery of cytotoxic drugs to the site of a tumor by the administration of a tumor-specific antibody-enzyme conjugate that binds to the tumor cells, and the additional administration of a prodrug that is converted at the tumor site, in the presence of the antibody-bound enzyme, to an active cytotoxic drug. The methods, antibody-enzyme conjugates and prodrugs of this invention overcome many of the drawbacks of the antibody-mediated drug delivery systems currently used in the treatment of cancers and other tumors.

BACKGROUND OF THE INVENTION

The use of immunoconjugates for the selective delivery of cytotoxic agents to tumor cells in the treatment of cancer is known in the art. The delivery of cytotoxic agents to the site of tumor cells is much desired because systemic administration of these agents often results in the killing of normal cells within the body as well as the tumor cells sought to be eliminated. Thus, according to the antitumor drug delivery systems currently in use, a cytotoxic agent is conjugated to a tumor-specific antibody to form an immunoconjugate that binds to the tumor cells and thereby "delivers" the cytotoxic agent to the site of the tumor. The immunoconjugates utilized in these targeting systems include antibody-drug conjugates [see, e.g., R. W. Baldwin et al., "Monoclonal Antibodies For Cancer Treatment," *Lancet*, pp. 603–05 (Mar. 15, 1986)] and antibody-toxin conjugates [see, e.g., P. E. Thorpe, "Antibody Carriers Of Cytotoxic Agents In Cancer Therapy: A Review," in *Monoclonal Antibodies '84: Biological And Clinical Applications*, A. Pinchera et al. (ed.s), pp. 475–506 (1985)].

Both polyclonal antibodies and monoclonal antibodies have been utilized in these immunoconjugates [see, e.g., K. Ohkawa et al., "Selective In Vitro And In Vivo Growth Inhibition Against Human Yolk Sac Tumor Cell Lines By Purified Antibody Against Human α-Fetoprotein Conjugated With Mitomycin C Via Human Serum Albumin," *Cancer Immunol. Immunother.*, 23, pp. 81–86 (1986) and G. F. Rowland et al., "Drug Localisation And Growth Inhibition Studies Of Vindesine-Monoclonal Anti-CEA Conjugates In A Human Tumour Xenograft," *Cancer Immunol. Immunother.*, 21, pp. 183–87 (1986). Drugs used in these immunoconjugates include daunomycin [see, e.g., J. Gallego et al., "Preparation Of Four Daunomycin-Monoclonal Antibody 791T/36 Conjugates With Anti-Tumour Activity," *Int. J. Cancer*, 33, pp. 737–44 (1984) and R. Arnon et al., "In Vitro And In Vivo Efficacy Of Conjugates Of Daunomycin With Anti-Tumor Antibodies," *Immunological Rev.*, 62, pp. 5–27 (1982)], methotrexate [N. Endo et al., "In Vitro Cytotoxicity Of A Human Serum Albumin-Mediated Conjugate Of Methotrexate With Anti-MM46 Monoclonal Antibody," *Cancer Research*, 47, pp. 1076–80 (1987)], mitomycin C [K. Ohkawa et al., supra], and vindesine [G. F. Rowland et al., supra]. Toxins used in the antibody-toxin conjugates include bacterial toxins such as diptheria toxin and plant toxins such as ricin [see, e.g., F. L. Moolten et al., "Antibodies Conjugated To Potent Cytotoxins As Specific Antitumor Agents," *Immunol. Rev.*, 62, pp. 47–73 (1982)].

Despite the amount of research directed towards the use of immunoconjugates for therapeutic purposes, several limitations involved with these delivery approaches have become apparent [see, e.g., M. J. Embleton, "Targeting Of Anti-Cancer Therapeutic Agents By Monoclonal Antibodies," *Biochemical Society Transactions* 14, pp. 393–395 (615th Meeting, Belfast 1986)]. Firstly, the large amount of drug required to be delivered to the target tumor cell to effect killing of the cell is often unobtainable because of limitations imposed by the number of tumor-associated antigens on the surface of the cells and the number of drug molecules that can be attached to any given antibody molecule. This limitation has led to the use of more potent cytotoxic agents such as plant toxins in these conjugates and to the development of polymer-bound antibody-drug conjugates having very high drug multiplicity ratios [see, e.g., P. E. Thorpe, supra, pp. 475–506 and R. W. Baldwin et al., "Design And Therapeutic Evaluation Of Monoclonal Antibody 791T/36 —Methotrexate Conjugates," in *Monoclonal Antibodies And Cancer Therapy*, pp. 215–31 (Alan R. Liss, Inc. 1985)]. However, even with large drug loading ratios or with the use of potent toxins, many immunoconjugates still display sub-optimal cytotoxic activity and are unable to effect complete killing at doses where all available antigenic sites are saturated.

Secondly, it has been recognized that the cytotoxic activity of an immunoconjugate is often dependent on its uptake, mediated by the antibody component of the conjugate, into the tumor cell [see, e.g., J. M. Lambert et al., "Purified Immunotoxins That Are Reactive With Human Lymphoid Cells," *J. Biol. Chem.*, 260 (No. 22), pp. 12035–12041 (1985)]. This internalization is crucial when using an antibody-drug conjugate in which the drug has an intracellular site of action or when using antibody-toxin conjugates. However, the vast majority of tumor-associated antigens and thus the antibody-drug or antibody-toxin conjugates bound to those antigens, are not internalized. Those conjugates that are internalized are often transported to the lysosome of the cell where the drug or toxin is degraded [see, E. S. Vitetta et al., *Science*. 238, pp. 1098–1104 (1987)]. Accordingly, although an antibody-drug or antibody-toxin conjugate may have excellent tumor-binding characteristics, the conjugate may nonetheless have a limited cytotoxic utility due to an inability to reach its site of action within the cell.

In addition, it is well established that tumor cell populations are often heterogeneous with respect to antigen expression [see, e.g., A. P. Albino et al., "Heterogeneity In Surface Antigen And Glycoprotein Expression Of Cell Lines Derived From Different Melanoma Metastases Of The Same Patient," *J. Exp. Med.*, 154, pp. 1764–78(1981)]. Furthermore, it has been demonstrated that antigen-positive tumor cells may give rise to antigen-negative progeny [see, e.g., M. Yeh et al., "Clonal Variation In Expression Of A Human Melanoma Antigen Defined By A Monoclonal Antibody," *J. Immunol.*, 126 (No. 4), pp. 1312–17 (1981)]. Thus, in any population of tumor cells, there will be a certain number of cells that do not possess the antigen for which a particular immunoconjugate is specific. The immunoconjugate will therefore not be able to bind to these cells and mediate their killing.

Due to these drawbacks, the currently utilized antitumor drug or toxin delivery systems have had a limited amount of success, especially when used for in vivo treatment.

In addition to the immunoconjugates discussed above, antibody-enzyme conjugates have been studied in vitro in combination with a second untargeted enzyme for the conversion of iodide or arsphenamine to their toxic forms in order to amplify antibody-mediated cytotoxicity [see, e.g., C. W. Parker et al., "Enzymatic Activation And Trapping Of Luminol-Substituted Peptides And Proteins. A Possible Means Of Amplifying The Cytotoxicity Of Anti-Tumor Antibodies," *Proc. Natl. Acad. Sci. USA*, 72 (No. 1), pp. 338–42 (1975) and G. W. Philpott et al., "Affinity Cytotoxicity Of Tumor Cells With Antibody-Glucose Oxidase Conjugates, Peroxidase, And Arsphenamine," *Cancer Research*, 34, pp. 2159–64 (1974)].

According to these in vitro studies, the enzyme, glucose oxidase, is attached to an antibody and used in combination with an untargeted peroxidase enzyme to convert iodide or arsphenamine to cytotoxic iodine or arsenical, respectively. This approach, therefore, requires not only the targeting of glucose oxidase to tumor cells with antibody, but also the presence at the tumor site of two other untargeted agents. The likelihood that all three of these agents will be present in vivo at the tumor site at the same time is small and therefore this approach is unlikely to be of therapeutic importance.

Canadian patent No. 1,216,791, issued to F. Jansen et al., on Jan. 20, 1987, discloses the conjugation to an antibody of an enzyme capable of liberating ammonium ions from substrates. The ammonium ions are then said to potentiate the cytotoxic action of certain immunotoxins targeted to the tumor site.

Finally, European patent application No. 84302218.7 discloses a method for treating a diseased cell population such as a tumor wherein an antibody is used to target a non-metabolizable antigen to the tumor cells. The antigen accumulates within at least a percentage of the tumor cells, which are then lysed to release the antigen into a ubiquitous fibronectin capturing matrix formed at the tumor site. At this point in the method of the invention, an iodine-containing ligand which is specific for and will bind to the antigen affixed to the matrix is administered. The cytotoxic iodine then acts to kill the tumor cells at that site. Many alternative embodiments are disclosed in this application, one of which suggests the use of an antibody-enzyme conjugate to target enzyme to a tumor site and the addition of a non-lethal substrate which the enzyme can convert to a cytotoxic material [see European application, pp. 34–35]. However, nowhere in the application is there any disclosure of how one is to perform this embodiment. Similarly, Hellstrom et al., "Antibodies For Drug Delivery," in *Controlled Drug Delivery* (2nd ed.), Robinson and Lee (ed.s), p. 639(1987) suggest that "[d]rugs which would be non-toxic until 'activated' by an agent (e.g., an enzyme) localized to tumor may be considered as another approach. . . ."

To date, however, no one has disclosed or suggested how the approach provided herein might be carried out nor has anyone actually attempted this approach to drug targeting.

SUMMARY OF THE INVENTION

The present invention addresses the problems referred to above by providing a novel method for delivering cytotoxic agents to tumor cells by the combined use of antibody-enzyme conjugates and prodrugs. According to this invention, an enzyme that is capable of converting a poorly or non-cytotoxic prodrug into an active cytotoxic drug is conjugated to a tumor-specific antibody. This antibody-enzyme conjugate is administered to a tumor-bearing mammalian host and binds, due to the antibody specificity, to the surface of those tumor cells which possess the tumor antigen for which the antibody is specific. The prodrug is then administered to the host and is converted at the tumor site by the action of the antibody-bound enzyme into a more active cytotoxic drug.

The present invention also encompasses a method of delivering cytotoxic drugs to tumor cells wherein a series of prodrugs is activated by a single antibody-bound enzyme. In addition, a series of different immunoconjugates, i.e., tumor-specific antibodies bearing different enzymes, can be utilized according to this invention to convert a number of different prodrugs into their more cytotoxic forms for the treatment of tumors. Alternatively, a series of different immunoconjugates wherein the specificity of the antibody component of the conjugate varies, i.e., each immunoconjugate contains an antibody against a different antigenic site on the tumor cell, can be utilized according to this invention to convert a prodrug or a number of prodrugs into a more active cytotoxic form.

According to preferred embodiments of this invention, antibody-enzyme conjugates containing the enzyme, alkaline phosphatase ("AP"), have been used in conjunction with the novel prodrug, etoposide-4'-phosphate or 7-(2'-aminoethyl phosphate)mitomycin or a combination thereof, to effect killing of tumor cells. According to another embodiment of the invention, an antibody-enzyme conjugate containing the enzyme, penicillin V amidase ("PVA"), has been used in conjunction with a novel prodrug, N-(p-hydroxyphenoxyacetyl)adriamycin to effect killing of tumor cells. Still another embodiment of the invention relates to the use of an antibody-enzyme conjugate containing the enzyme, cytosine deaminase ("CD"), in combination with the prodrug, 5-fluorocytosine, to effect killing of tumor cells.

The immunoconjugates and prodrugs of this invention may be used in antitumor compositions, such as those comprising a pharmaceutically effective amount of at least one immunoconjugate or prodrug of the invention and a pharmaceutically acceptable carrier. In addition, the immunoconjugates and prodrugs may be used in combinations and methods for treating tumors in mammals comprising the step of treating a mammal with a pharmaceutically effective amount of the compositions of this invention.

Advantageously, the methods, immunoconjugates, prodrugs, pharmaceutical compositions and combinations of this invention provide a relatively simple and direct procedure for delivering cytotoxic drugs to tumor cells, allowing enhanced selective cytotoxicity while avoiding the problems of heterogeneous antigen expression, antigen/antibody internalization and insufficient drug potency inherent in conventional antibody-directed immunotherapy techniques.

BRIEF DESCRIPTION OF THE DRAWINGS

FIG. 4 depicts the high pressure liquid chromatography (HPLC) (as monitored at 254 nm) of: (A) etoposide-4'-phosphate alone, i.e., in the absence of AP or the AP-L6 conjugate; (B) etoposide alone; (C) the product produced 5 minutes after the reaction of the etoposide-4'-phosphate prodrug with AP; and (D) the product produced 5 minutes after the reaction of the etoposide-4'-phosphate prodrug with the L6-AP conjugate of the invention.

FIG. 10 depicts analyses of the phosphatase activity in tumors that were untreated or treated with the conjugates of the invention.

DETAILED DESCRIPTION OF THE INVENTION

The present invention relates to a novel method for the delivery of cytotoxic agents to tumor cells and provides for enhanced selective killing of tumor cells in the treatment of cancers, such as carcinomas and melanomas, as well as other tumors.

Figure 1:
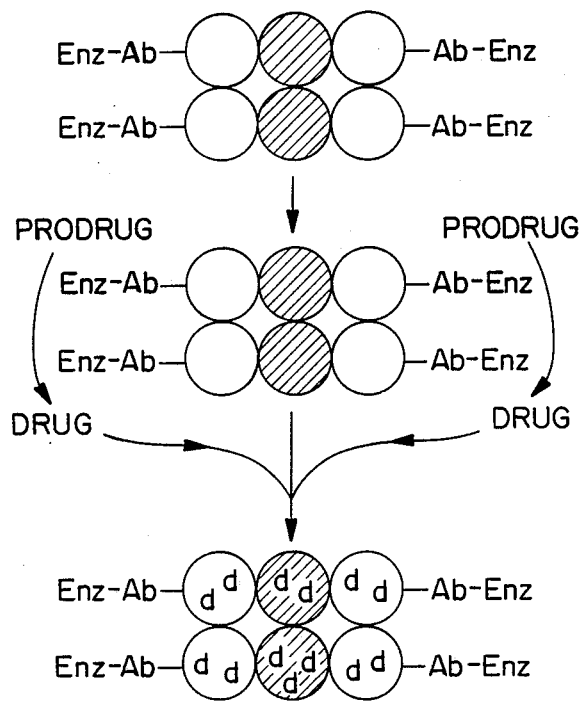
FIG. 1 depicts the strategy used for the activation of prodrugs at tumor cells that bind antibody-enzyme conjugates.

According to the method of this invention, an antibody-enzyme conjugate is administered to a tumor-bearing mammalian host. This antibody-enzyme conjugate consists of a tumor-specific antibody linked to an enzyme that is capable of converting a prodrug, that is less cytotoxic to tumor cells than the parent drug, into the more active parent drug. When introduced into the host, the antibody component of the conjugate, which is reactive with an antigen found on the tumor cells, directs the conjugate to the site of the tumor and binds to the tumor cells. The antibody can therefore be viewed as delivering the enzyme to the site of the tumor. A prodrug that is a substrate for the enzyme is then introduced into the host and is converted, at the tumor site, by the enzyme into an active cytotoxic drug. The drug is thus activated extracellularly and can diffuse into all of the tumor cells at that site, i.e., those cells bearing the particular tumor antigen to which the antibody of the conjugate is specific and to which the antibody has bound as well as those cells that are negative for that antigen but are nonetheless present at the site of the tumor (see FIG. 1). The method of this invention therefore overcomes the current problems of tumor antigen heterogeneity and the requirement of antigen/conjugate internalization associated with conventional immunoconjugate drug delivery techniques.

Furthermore, because the present method does not require the drug to be bound directly to the antibody and thereby limit the amount of drug that can be delivered, the commonplace problem of drug potency at the tumor site does not arise. In fact, the present method amplifies the number of active drug molecules present at the tumor site because the antibody-bound enzyme of the conjugate can undergo numerous substrate turnovers, repeatedly converting prodrug into active drug. Moreover, the present method is capable of releasing the active drug specifically at the tumor site as opposed to release at other tissues. This is so because the concentration of the enzyme at the tumor site is higher than its concentration at other tissues due to the coating of the tumor cells with the antibody-enzyme conjugate.

The antibody component of the immunoconjugate of the invention includes any antibody which binds specifically to a tumor-associated antigen. Examples of such antibodies include, but are not limited to, those which bind specifically to antigens found on carcinomas, melanomas, lymphomas and bone and soft tissue sarcomas as well as other tumors. Antibodies that remain bound to the cell surface for extended periods or that are internalized very slowly are preferred. These antibodies may be polyclonal or preferably, monoclonal, may be intact antibody molecules or fragments containing the active binding region of the antibody, e.g., Fab or F(ab')$_2$, and can be produced using techniques well established in the art [see, e.g., R. A. DeWeger et al., "Eradication Of Murine Lymphoma And Melanoma Cells By Chlorambucil-Antibody Complexes, *Immunological Rev.*, 62, pp. 29–45 (1982) (tumor-specific polyclonal antibodies produced and used in conjugates); M. Yeh et al., "Cell Surface Antigens Of Human Melanoma Identified By Monoclonal Antibody," *Proc. Natl. Acad. Sci.*, 76, p. 2927 (1979); J. P. Brown et al. "Structural Characterization Of Human Melanoma-Associated Antigen p97 With Monoclonal Antibodies," *J. Immunol.*, 127 (No.2), pp. 539–546 (1981) (tumor-specific monoclonal antibodies produced); and J. P. Mach et al., "Improvement Of Colon Carcinoma Imaging: From Polyclonal Anti-CEA Antibodies And Static Photoscanning To Monoclonal Fab Fragments And ECT", in *Monoclonal Antibodies For Cancer Detection And Therapy*, R. W. Baldwin et al. (ed.s), pp. 53–64 (Academic Press 1985) (antibody fragments produced and used to localize to tumor cells)]. In addition, if monoclonal antibodies are used, the antibodies may be of mouse or human origin or chimeric antibodies [see, e.g., V. T. Oi, "Chimeric Antibodies," *BioTechniques* 4 (No. 3), pp. 214–221 (1986)].

The enzyme component of the immunoconjugate of the invention includes any enzyme capable of acting on a prodrug in such a way so as to convert it into its more active, cytotoxic form. The term "prodrug" as used in this application refers to a precursor or derivative form of a pharmaceutically active substance that is less cytotoxic to tumor cells compared to the parent drug and is capable of being enzymatically activated or converted into the more active parent form [see, e.g., D.E.V. Wilman, "Prodrugs In Cancer Chemotherapy," *Biochemical Society Transactions*, 14, pp. 375–382 (615th Meeting, Belfast 1986) and V. J. Stella et al.,"Prodrugs: A Chemical Approach To Targeted Drug Delivery," *Directed Drug Delivery*, R. Borchardt et al. (ed.), pp.247–267 (Humana Press 1985)].

Enzymes that are useful in the method of this invention include, but are not limited to alkaline phosphatase useful for converting phosphate-containing prodrugs into free drugs, arylsulfatase useful for converting sulfate-containing prodrugs into free drugs, cytosine deaminase useful for converting non-toxic 5-fluorocytosine into the anti-cancer drug, 5-fluorouracil, proteases, such as serratia protease, thermolysin, subtilisin, carboxypeptidases and cathepsins (such as cathepsins B and L), that are useful for converting peptide-containing prodrugs into free drugs, D-alanylcarboxypeptidases, useful for converting prodrugs that contain D-amino acid substituents, carbohydrate-cleaving enzymes such as β-galactosidase and neuraminidase useful for converting glycosylated prodrugs into free drugs, β-lactamase useful for converting drugs derivatized with β-lactams into free drugs, and pencillin amidases, such as pencillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as abzymes, can be used to convert the prodrugs of the invention into free active drugs [see, e.g., R. J. Massey, *Nature*, 328, pp. 457–458 (1987)]. Antibody-abzyme conjugates can be prepared as described herein for delivery of the abzyme to a tumor cell population.

Similarly, the prodrugs of this invention include, but are not limited to, the above-listed prodrugs, e.g., phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted by the enzyme of the conjugate into the more active, cytotoxic free drug. Examples of cytotoxic drugs that can be derivatized into a prodrug form for use in this invention include, but are not limited to, etoposide, teniposide, adriamycin, daunomycin, carminomycin, aminopterin, dactinomycin, mitomycins, cis-platinum and cis-platinum analogues, bleomycins, esperamicins [see U.S. Pat. No. 4,675,187], 5-fluorouracil, melphalan and other related nitrogen mustards.

The enzymes of this invention can be covalently bound to the antibodies of this invention by techniques well known in the art such as the use of the heterobifunctional crosslinking reagent, SPDP (N-succinimidyl-3-(2-pyridyldithio)propionate) or SMCC (succinimidyl 4-(N-maleimidomethyl) cyclohexane-1-carboxylate [see, e.g., P. E. Thorpe et al., "The Preparation And Cytotoxic Properties Of Antibody-Toxin Conjugates," *Immunological Rev.*, 62, pp. 119–58 (1982); J. M. Lambert et al., supra, at p. 12038; G. F. Rowland et al., supra, at pp. 183–84 and J. Gallego et al., supra, at pp. 737–38]. Alternatively, fusion proteins comprising at least the antigen binding region of an antibody of the invention linked to at least a functionally active portion of an enzyme of the invention can be constructed using recombinant DNA techniques well known in the art [see, e.g., M. S. Neuberger et al., *Nature*, 312, pp. 604–608 (1984)]. These fusion proteins act in essentially the same manner as the antibody-enzyme conjugates described herein.

Figure 3:
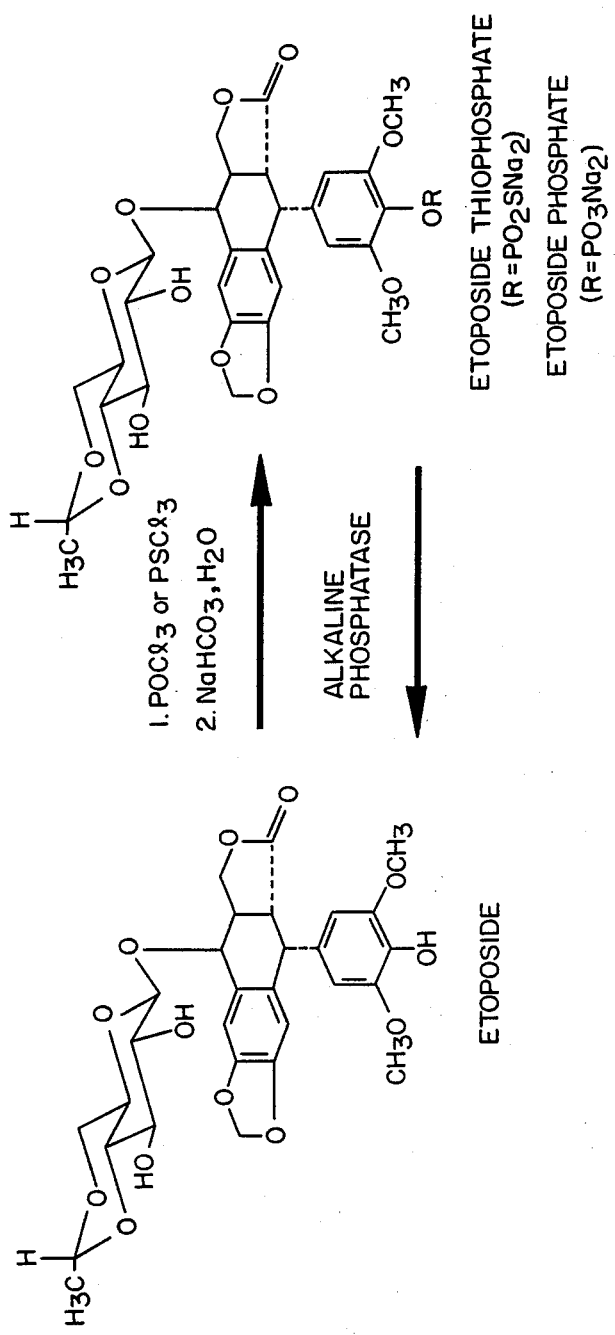
FIG. 3 depicts the preparation and hydrolysis of etoposide phosphate and etoposide thiophosphate prodrugs of this invention.

According to a preferred embodiment of this invention, an antibody specific for a human cancer antigen was conjugated to the enzyme, alkaline phosphatase, and used according to the method of the invention to convert a 4'-phosphate derivative of the epipodophyllotoxin glucosides into an active anti-cancer drug. Such derivatives include etoposide-4'-phosphate, etoposide-4'-thiophosphate and teniposide-4'-phosphate (see FIG. 3 for the structures of these derivatives; the teniposide derivative has a 2-thienyl group in place of the methyl group on the sugar moiety of the structures depicted). Other embodiments of the invention may include phosphate derivatives of these glucosides wherein the phosphate moiety is placed at other hydroxyl groups on the glucosides. According to a more preferred embodiment, however, the phosphate derivative used as a prodrug in this invention is etoposide-4'-phosphate or etoposide-4'-thiophosphate.

According to the present invention, alkaline phosphatase, AP, was covalently linked to the monoclonal antibody, L6, an IgG2a antibody that binds to a glycoprotein antigen on human lung carcinoma cells [I. Hellstrom et al., "Antitumor Effects Of L6, An IgG2a Antibody That Reacts With Most Human Carcinomas," *Proc. Natl. Acad. Sci. USA*, 83, pp. 7059–63 (1986)]. The immunoconjugate that resulted showed no loss of enzymatic activity when compared to that of the unconjugated enzyme. In addition, most of the binding activity of the L6 antibody was preserved in the immunoconjugate.

Using in vitro cytotoxicity assays, we demonstrated that treatment of cells from a human carcinoma cell line with the L6-AP immunoconjugate followed by exposure of the cells to an etoposide phosphate prodrug resulted in a cytotoxicity comparable to the use of etoposide alone on those cancer cells. In contrast, the etoposide phosphate alone showed little cytotoxicity.

Furthermore, our in vivo studies in nude mice have demonstrated that the L6-AP immunoconjugate localizes to L6-positive tumor xenografts. Histological evaluation of those tumors indicated that the targeted AP enzyme was distributed throughout the tumor mass.

In addition, the L6-AP immunoconjugate demonstrated strong in vivo antitumor activity in therapy experiments wherein the conjugate was administered to nude mice bearing subcutaneous L6-positive tumors followed by treatment with an etoposide phosphate prodrug. The antitumor effect of this treatment included the complete regression of some tumors and was superior to the effect of treatment with the prodrug or parent drug alone.

According to another preferred embodiment of the invention, the L6-AP immunoconjugate was used to convert a novel mitomycin phosphate prodrug into an active mitomycin drug. As is the case with the etoposide phosphate prodrug, the AP enzyme of the conjugate removes the phosphate group from the prodrug, releasing an active antitumor agent. The mitomycin phosphate prodrug of this embodiment may be an $N^7$-$C_{1-8}$ alkyl phosphate derivative of mitomycin C or porfiromycin, or pharmaceutically acceptable salts thereof. $N^7$ refers to the nitrogen atom attached to the 7-position of the mitosane nucleus of the parent drug. According to a more preferred embodiment, the derivative used is 7-(2'-aminoethylphosphate)mitomycin ("MOP") (see FIG. 12 for the structures of mitomycin C and MOP in the form of a disodium salt; the porfiromycin derivative corresponding to MOP has a methyl group on the aziridine nitrogen of mitomycin C). Alternatively, the MOP compound may be termed, 9a-methoxy-7-[[(phosphonooxy)ethyl]amino]mitosane disodium salt. Other embodiments of the invention may include the use of $N^7$-alkyl mitomycin phosphorothioates as prodrugs.

In vitro studies indicated that treatment of cells from a human lung tumor line with the L6-AP immunoconjugate followed by exposure of the cells to MOP resulted in a cytotoxicity comparable to the use of the recognized antitumor agent, mitomycin, alone on the tumor cells. Use of the mitomycin phosphate prodrug alone on the tumor cells resulted in little cytotoxicity. Similarly, the L6-AP immunoconjugate showed a pronounced antitumor effect in vivo in therapy experiments wherein the conjugate was administered to nude mice bearing human lung tumors followed by treatment with the mitomycin phosphate prodrug. This antitumor effect was greater than that seen using the prodrug alone, the parent drug alone, or the prodrug given along with a non-binding antibody-AP conjugate.

In still another embodiment of the invention, a penicillin amidase enzyme was covalently linked to the L6 monoclonal antibody and the resulting immunoconjugate was used to convert a novel adriamycin prodrug into the active antitumor drug, adriamycin. The particular amidase utilized was a penicillin V amidase ("PVA") isolated from *Fusarium oxYsporum* that hydrolyzes phenoxyacetyl amide bonds. Thus, the particular prodrug utilized was N-(p-hydroxyphenoxyacetyl)adriamycin ("APO"), which was hydrolyzed by the amidase to release the potent antitumor agent, adriamycin. The L6-PVA immunoconjugate showed no loss of enzymatic activity when compared to that of the unconjugated enzyme and most of the binding activity of the L6 antibody was preserved in the conjugate.

According to our in vitro studies, treatment of human lung tumor cells with the L6-PVA conjugate followed by exposure of the cells to the APO prodrug resulted in a cytotoxicity comparable to that seen upon treatment of the cells with adriamycin alone. Importantly, the APO prodrug alone demonstrated much less cytotoxicity toward the tumor cells.

Similar in vitro studies were also performed using an 1F5-PVA conjugate in which the PVA enzyme was conjugated to 1F5, a monoclonal antibody reactive with an antigen found on lymphoma cells. Treatment of Daudi lymphoma cells with the 1F5-PVA conjugate followed by exposure of the cells to APO resulted in a cytotoxicity comparable to that seen upon treatment with adriamycin alone, while treatment of the cells with APO alone resulted in very little cytotoxicity.

Although the synthesis and use of the novel adriamycin prodrug, N-(p-hydroxyphenoxyacetyl)adriamycin, is described herein, it should be understood that the present invention includes the synthesis and use of other related adriamycin prodrugs that can be derivatized in substantially the same manner. For example, the prodrug, N-(phenoxyacetyl) adriamycin is also within the scope of the invention in that the prodrug can be synthesized using the protocol described herein but substituting phenoxyacetic acid for the reactant, p-hydroxyphenoxyacetic acid (see Example 4, infra). In addition, it is to be understood that the adriamycin prodrugs of this invention include other N-hydroxyphenoxyacetyl derivatives of adriamycin, e.g., substituted at different positions of the phenyl ring, as well as N-phenoxyacetyl derivatives containing substituents on the phenyl ring other than the hydroxyl group described herein.

Furthermore, the present embodiment encompasses the use of other amidases, such as penicillin G amidase, as the enzyme component of the immunoconjugate as well as other prodrugs correspondingly derivatized such that the particular amidase can hydrolyze that prodrug to an active antitumor form. For example, when a penicillin G amidase is used as the enzyme, the prodrug should contain a phenylacetylamide group (as opposed to the phenoxyacetylamide group of APO) because penicillin G amidases hydrolyze this type of amide bond [see, e.g., A. L. Margolin et al., *Biochim. Biophys. Acta.* 616, pp. 283–89 (1980)]. Thus, other prodrugs of the invention include N-(p-hydroxyphenylacetyl)adriamycin, N-(phenylacetyl) adriamycin and other optionally substituted N-phenylacetyl derivatives of adriamycin.

It should also be understood that the present invention includes any prodrug derived by reacting the amine group of the parent drug with the carboxyl group of phenoxyacetic acid, phenylacetic acid or other related acids. Thus, prodrugs of anthracyclines other than adriamycin that are capable of being derivatized and acting in substantially the same manner as the adriamycin prodrugs described herein falls within the scope of this invention. For example, other prodrugs that can be produced and used in accordance with this invention include hydroxyphenoxyacetylamide derivatives, hydroxyphenylacetylamide derivatives, phenoxyacetylamide derivatives and phenylacetylamide derivatives of anthracyclines such as daunomycin and carminomycin. Other amine-containing drugs such as melphalan, mitomycin, aminopterin, bleomycin and dactinomycin can also be modified as described herein to yield prodrugs of the invention.

It is apparent therefore that the present invention encompasses compounds having formulae I and II:

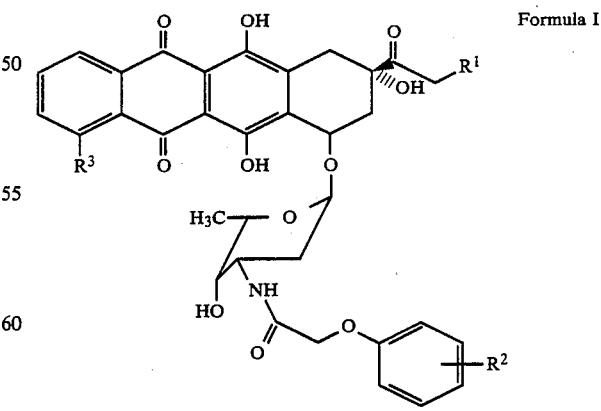

Formula I wherein:
$R^1$ is H, and $R^3$ is OH or OCH$_3$; or
$R^1$ is OH and $R^3$ is OCH$_3$; and
$R^2$ is H or OH; and

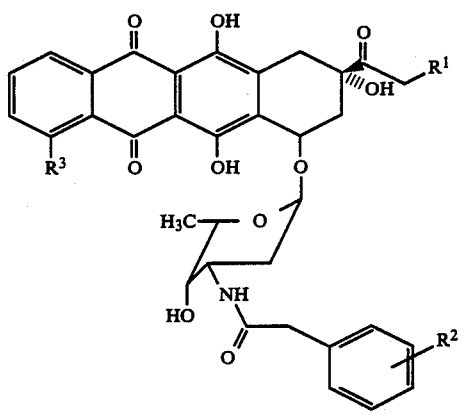

Formula II wherein:
$R^1$ is H, and $R^3$ is OH or $OCH_3$; or
$R^1$ is OH and $R^3$ is $OCH_3$; and
$R^2$ is H or OH.

Yet another preferred embodiment of the invention involves the conjugation of the enzyme, cytosine deaminase ("CD"), to the L6 monoclonal antibody. The deaminase enzyme catalyzes the conversion of 5-fluorocytosine ("5-FC"), a compound lacking in antineoplastic activity, to the potent antitumor drug, 5-fluorouracil ("5-FU") (see FIG. 24). Thus, the L6-CD immunoconjugate of the invention was used to convert the prodrug, 5-FC, into 5-FU, resulting in a significant cytotoxic effect on tumor cells in vitro.

As was true for the immunoconjugates of the invention described hereinbefore, the L6-CD conjugate showed no significant loss of enzymatic or binding activity due to conjugation. Furthermore, our in vitro studies demonstrated that treatment of human lung tumor cells with the L6-CD conjugate followed by exposure of the cells to the prodrug, 5-FC, resulted in a cytotoxic effect equal to that seen upon treatment of the cells with the potent antitumor drug, 5-FU, alone. Treatment of those tumor cells with the prodrug alone resulted in an insignificant cytotoxic effect.

It is apparent from the extensive data described herein that the immunoconjugate/prodrug combination of this invention provides a selective mechanism for killing tumor cells wherein a prodrug is administered that has diminished cytotoxic activity, the prodrug being converted to a highly cytotoxic state at the site of tumor cells, due to the presence there of the antibody-targeted enzyme. Furthermore, the cytotoxicity achieved by this method is enhanced over conventional antibody-targeting techniques because the active drug released at the tumor site is not encumbered by the physical limitations that accompany antibody-drug conjugate delivery systems, as discussed above. It is clear, therefore, that the method of this invention provides a way to enhance selective cytotoxicity with respect to tumor cells in the treatment of cancers and other tumors.

Another embodiment of the method of this invention provides a method of combination chemotherapy using several prodrugs and only a single antibody-enzyme conjugate. According to this embodiment, a number of prodrugs are used that are all substrates for the same enzyme in an immunoconjugate. Thus, a particular antibody-enzyme conjugate converts a number of prodrugs into cytotoxic form, resulting in increased antitumor activity at the tumor site. For example, a pronounced antitumor effect was obtained in in vivo studies wherein the L6-AP immunoconjugate of the invention was administered to nude mice bearing human lung tumors followed by treatment with a combination of novel prodrugs, i.e., an etoposide phosphate prodrug and a mitomycin phosphate prodrug, given together. Similarly, administration of an etoposide phosphate, adriamycin phosphate [see U.S. Pat. No. 4,185,111] and 5-fluorouridine monophosphate [see, e.g., C. Heidelberger et al., "Fluorinated Pyrimidines And Their Nucleosides", in Adv. Enzymol. Relat. Areas Mol. Biol., 54, pp. 57-119 (1983)] after treatment with an antitumor antibody-AP conjugate results in the formation of a combination of potent antitumor drugs at the site of the tumor, i.e., etoposide, adriamycin and 5-fluorouridine.

According to another embodiment, a number of different immunoconjugates are used, wherein the enzyme component of the conjugate varies. Each immunoconjugate can be used to convert its respective prodrug or prodrugs into cytotoxic form at the tumor site. For example, an antitumor antibody can be linked to AP to form one conjugate and can be linked to cytosine deaminase to form another conjugate. Both immunoconjugates are then administered to a tumor-bearing host and will bind to the tumor antigen at the tumor site via the antibody specificity. Administration of the prodrugs, etoposide phosphate and 5-fluorocytosine, will result in the formation of etoposide and 5-fluorouracil, both potent antitumor agents, at the tumor site.

Still another embodiment of this invention involves the use of a number of immunoconjugates wherein the specificity of the antibody component of the conjugate varies, i.e., a number of immunoconjugates are used, each one having an antibody that binds specifically to a different antigen on the tumor of interest. The enzyme component of these immunoconjugates may be the same or may vary. This embodiment may be especially useful in situations where the amounts of the various antigens on the surface of a tumor is unknown and one wants to be certain that sufficient enzyme is targeted to the tumor site. The use of a number of conjugates bearing different antigenic specificities for the tumor increases the likelihood of obtaining sufficient enzyme at the tumor site for conversion of a prodrug or series of prodrugs. Additionally, this embodiment is important for achieving a high degree of specificity for the tumor because the likelihood that normal tissue will possess all of the same tumor-associated antigens is small [cf., I. Hellstrom et al., "Monoclonal Antibodies To Two Determinants Of Melanoma-Antigen p97 Act Synergistically In Complement-Dependent Cytotoxicity", J. Immunol., 127 (No. 1), pp. 157-160 (1981)].

The present invention also encompasses pharmaceutical compositions, combinations and methods for treating cancers and other tumors. More particularly, the invention includes combinations comprising the antibody-enzyme conjugates of the invention and the corresponding prodrug or prodrugs for use in a method for treating tumors wherein a mammalian host is treated in a pharmaceutically acceptable manner with a pharmaceutically effective amount of an antibody-enzyme conjugate or conjugates and a pharmaceutically effective amount of a prodrug or prodrugs. The combination and methods of this invention are useful in treating any mammal, including humans, dogs, cats, and horses.

According to a preferred embodiment, the antibody-enzyme conjugate is administered prior to the introduction of the prodrug into the host. Sufficient time should be allowed between administration of the conjugate and the prodrug to allow the antibody of the conjugate to target and localize the enzyme to the tumor site. Such sufficient time may range from 12 hours to one week depending upon the conjugate used.

The conjugates and prodrugs of the invention can be administered using conventional modes of administration including, but not limited to, intravenous, intraperitoneal, oral, intralymphatic, or administration directly into the tumor. Intravenous administration is preferred.

The compositions of the invention—comprising the immunoconjugates or prodrugs—may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application. For example, oral administration of the antibody-enzyme conjugate may be disfavored because the conjugate proteins tend to be degraded in the stomach if taken orally, e.g., in tablet form.

The conjugate or prodrug compositions also preferably include conventional pharmaceutically acceptable carriers and adjuvants known in the art such as human serum albumin, ion exchangers, alumina, lecithin, buffer substances such as phosphates, glycine, sorbic acid, potassium sorbate, and salts or electrolytes such as protamine sulfate.

The most effective mode of administration and dosage regimen for the compositions of this invention depends upon the severity and course of the disease, the patient's health and response to treatment and the judgment of the treating physician. Accordingly, the dosages of the immunoconjugates and prodrugs should be titrated to the individual patient.

Nevertheless, an effective dose of the antibody-enzyme conjugate of this invention may be in the range of from about 1.0 to about 100 mg/m$^2$. An effective dose of the prodrug of the invention will depend upon the particular prodrug used and the parent drug from which it is derived. Since the prodrug is less cytotoxic than the parent drug, dosages in excess of those recognized in the art for the parent drug may be used. For example, an effective dose of the etoposide prodrugs may be in the range of from about 75–500 mg/m$^2$. An effective dose of the mitomycin phosphate prodrugs may be in the range of from about 50–1000 mg/m$^2$. An effective dose of the adriamycin prodrugs may be in the in the range of from about 15–150 mg/m$^2$. And, an effective dose of 5-fluorocytosine and other 5-fluorouridine prodrugs may be in the range of from about 600–2000 mg/m$^2$.

In order that the invention described herein may be more fully understood, the following examples are set forth. It should be understood that these examples are for illustrative purposes only and are not to be construed as limiting the scope of this invention in any manner.

EXAMPLE 1

The following example demonstrates the use of the immunoconjugates and methods of this invention for the conversion of an etoposide phosphate prodrug into etoposide by antibody-bound alkaline phosphatase and the resulting in vitro cytotoxicity towards tumor cells and in vivo antitumor effects demonstrated by the use of the methods of this invention.

Preparation Of Antibody-Alkaline Phosphatase Conjugates Of The Invention

In this example, three immunoconjugates were prepared and studied, comprising either the monoclonal antibody L6, 96.5 or 1F5 conjugated to the enzyme, alkaline phosphatase (AP). L6 is a monoclonal antibody of the IgG2a subclass that is specific for and binds to a glycoprotein antigen on human lung carcinoma cells [see I. Hellstrom et al., (1986), supra. 96.5 is a monoclonal IgG2a antibody that is specific for p97, a melanoma-associated antigen [see J. P. Brown et al., "Structural Characterization Of Human Melanoma-Associated Antigen p97 With Monoclonal Antibodies," *J. Immunol.*, 127 (No. 2), pp. 539–46 (1981)]. 1F5 is a monoclonal IgG2a antibody that is specific for the CD-20 antigen on normal and neoplastic B cells [see, E. A. Clark et al., "Role Of The Bp35 Cell Surface Polypeptide In Human B-Cell Activation," *Proc. Natl. Acad. Sci. USA*, 82, pp. 1766–70 (1985)]. The L6 hybridoma that produces the L6 monoclonal antibody was deposited with the American Type Culture Collection (ATCC) under accession number HB8677 in connection with the filing of European patent application No. 207963, published on Jan. 14, 1987. The 1F5 hybridoma that produces the 1F5 monoclonal antibody was deposited with the ATCC on Feb. 12, 1988 under ATCC No. HB9645. The 96.5 monoclonal antibody is commercially available.

The antibody-enzyme conjugates were prepared by covalently linking AP to the monoclonal antibodies L6, 96.5, or 1F5 through a thioether linkage using a method similar to that described in J. M. Lambert et al., "Purified Immunotoxins That Are Reactive With Human Lymphoid Cells," *J. Biol. Chem.*, 260 (No. 22), pp. 12035–12041 (1985). According to one experimental protocol, the conjugates, L6-AP and 96.5-AP, were prepared as follows: We added 2-iminothiolane (50 mM in 0.5M triethanolamine hydrochloride with 10 mM EDTA at pH 8.0) to a 8.0 mg/ml solution of L6 or 96.5 antibody (in 50 mM triethanolamine hydrochloride and 1 mM EDTA at pH 8.0) so that the final concentration of the 2-iminothiolane was 1.3 mM. After 90 min at 0° C., the reaction was stopped by gel filtration on Sephadex G-25 using phosphate buffered saline (PBS) at pH 7.2 as eluant. Reaction of the antibodies with 2-iminothiolane introduced sulfhydryl groups, the number of which was determined to be 1.9–3.5 using Ellman's reagent [see P. W. Riddles et al., "Ellman's Reagent: 5,5'-Dithiobis(2-nitrobenzoic Acid)-A Reexamination," Analytical Biochemistry, 94, pp. 75–81 (1979)].

Alkaline phosphatase (calf intestine, Boehringer Mannheim, 10 mg/ml) in 100 mM phosphate buffer at pH 7.0 was treated with sulfosuccinimidyl 4-(N-maleimidomethyl)cyclohexane-1-carboxylate (sulfo-SMCC)(Pierce Chemical Co., 20 mM in dimethyl formamide (DMF)) so that the final sulfo-SMCC concentration was 2.4 mM. After 30 min at 30° C., the modified enzyme was purified by gel filtration on G-25 Sephadex and eluted with PBS.

The modified AP was then added to the thiolated antibody in a 2:1 molar ratio. Reaction of AP with sulfo-SMCC introduced maleimido groups into the enzyme that when reacted with the sulfhydryl groups on each modified antibody resulted in the formation of a thioether linkage between the antibody and AP.

Figure 2:
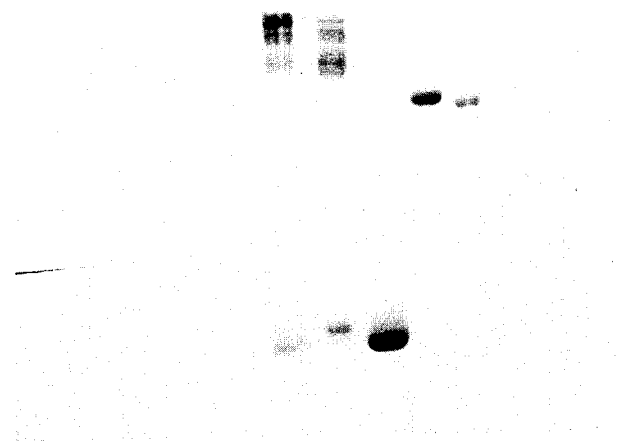
FIG. 2 depicts an SDS-polyacrylamide gel analysis (5–12.5% gradient gel, non-reducing) of: (A) the 96.5-AP immunoconjugate; (B) the L6-AP immunoconjugate; (C) AP; (D) monoclonal antibody 96.5; and (E) monoclonal antibody L6.

Iodoacetamide (final concentration 1 mM) was added to the protein solution after 1 hour of reaction time in order to block any remaining unreacted thiols, and the conjugates were purified on a Sephacryl S-300 column using PBS as eluant. Fractions were monitored at 280 nm and the AP activity of each fraction (diluted 64,000 fold) was assayed for at pH 9.5 using p-nitrophenylphosphate as substrate [P. Tijssen, *Laboratory Techniques In BiochemistrY And Molecular Biology*, pp. 366–67, (Elsevier Press 1985)]. Those fractions containing conjugates with appropriate levels of AP-antibody ratios were determined by SDS-PAGE on a 5–12.5% gradient gel (see FIG. 2) and were then pooled. The protein concentration was determined at 280 nm where 0.1% solution of the antibodies and AP absorb 1.4 and 0.76 OD's, respectively. Analysis of the conjugates on the gel indicated that they consisted primarily of 1:1 ratios of antibody to enzyme. Under the denaturing conditions used for the gel, AP, which exists in nature as a homo-dimer of molecular weight 140 kd, migrates as a single band of 70 kd. This 70 kd protein band was observed on the gel in those columns which also contained the higher molecular weight conjugate bands because one of the subunits of the enzyme dissociated from the covalently linked antibody-enzyme conjugate (see FIG. 2, lanes A and B). Gel filtration on an S-300 Sephacryl column indicated that there was no free enzyme present in the conjugate preparation.

We also used a second, similar experimental protocol to prepare the L6-AP and 1F5-AP conjugates of the invention, wherein the antibody was modified With iminothiolane (0.5 mM) to introduce a single free thiol group and AP was modified with succinimidyl 4-(N-maleimidomethyl)-cyclohexane-1-carboxylate (SMCC)(Pierce Chemical Co., Rockford, Ill.) so that the final concentration of SMCC was 1.0 mM. The modified proteins were then combined and the resulting conjugates purified by gel filtration on S-300 Sephacryl. Subsèquent SDS-PAGE analysis indicated that these conjugate preparations were free of unconjugated proteins and aggregates. As described above, the protein concentrations of the preparations were determined by absorbance at 280 nm where 1 mg/ml solutions of the antibody (molecular weight: 160 kd) and AP (molecular weight: 140 kd) absorb 1.4 and 0.76 OD units, respectively.

Preparation Of The Prodrugs, Etoposide Phosphate And Etoposide Thiophosphate

According to the next step of the method of this invention, each antibody-enzyme conjugate was reacted with a novel etoposide phosphate or etoposide thiophosphate prodrug. More particularly, the prodrugs utilized were the 4'-disodium phosphate ester of etoposide and the 4'-disodium thiophosphate ester of etoposide, respectively, having the formulae depicted in FIG. 3.

Etoposide phosphate and etoposide thiophosphate were synthesized by reacting etoposide with phosphorous oxychloride or thiophosphoryl chloride, respectively, to produce either a dichlorophosphate or dichlorothiophosphate intermediate. The phosphorylation reaction is performed in a suitable anhydrous organic solvent, e.g., acetonitrile, and preferably in the presence of a tertiary amine base, e.g., N,N-diisopropylethylamine. The course of the reaction is monitored by thin layer chromatography (TLC), by which the optimum reaction time may be judged by the appearance of product of the disappearance of the starting material, or both. According to our experience, the reaction may take from about 4 hours to about 72 hours, depending on the quality of the phosphorous reagents used. Hydrolysis of the dichlorophosphate or dichlorothiophosphate intermediate to the disodium phosphate or thiophosphate prodrug, respectively, was carried out by adding a solution of sodium bicarbonate (20–50 fold excess) in water directly to the reaction mixture and allowing the mixture to stir at room temperature for 1.5 or 3 hours, respectively. Partitioning with ethyl acetate and water followed by reverse phase chromatography of the aqueous layer using water-methanol yields the desired prodrugs after lyophilization or evaporation of the aqueous media in vacuo.

A more detailed description of the preparation of the 4'-disodium phosphate derivative of etoposide which was used as one prodrug in the method of this invention is as follows:

A magnetically stirred suspension of etoposide (Bristol-Myers Co., 2.30 g, 3.91 mmol) in dry acetonitrile (210 ml) was warmed to give a nearly complete solution, cooled to room temperaturè, and treated with N,N-diisopropylethylamine (2.36 ml, 13.5 mmol). The mixture was then cooled to 0° C. and treated via syringe over 30 sec with phosphoryl chloride, $POCl_3$ (666 mg, 4.34 mmol). The mixture was allowed to slowly come to room temperature over 2–3 hours and stirred at room temperature for 63 hours. At the end of this period, the reaction mixture was treated with a solution of sodium bicarbonate (6.0 g, 71.4 mmol) in deionized $H_2O$ (110 ml), the mixture was stirred at room temperature for 80 min, and then partitioned with saturated aqueous sodium bicarbonate (20 ml), deionized $H_2O$ (125 ml), and ethyl acetate (350 ml). The organic layer was further extracted with deionized $H_2O$ (1×50 ml) and the combined aqueous layers were washed with ethyl acetate (250 ml) and then subjected to a vacuum of 0.5 mm at room temperature for 1 hour to remove dissolved solvents. The aqueous portion was then applied to a 4 cm diameter column containing 15 cm of octadecylsilane (C-18) bonded· to silica gel that had been packed in methanol and then equilibrated with $H_2O$. After all of the aqueous portion was applied, the column was eluted with $H_2O$ (175 ml) to remove inorganic salts and then the product was eluted with 20% methanol in water. Concentration of the solvent at 0.5 torr provided 744 mg (36%) of the pure etoposide phosphate compound as a colorless solid. Alternatively, lyophilization provides the pure compound as a very fluffy low density solid.

According to another embodiment, the etoposide phosphate prodrug of the invention was prepared as follows:

A magnetically stirred suspension of etoposide (10.50 g, 17.84 mmol, dried over $P_2O_5$ at 80° C./0.5 torr) in dry acetonitrile (450 ml) was treated with diisopropylethylamine (4.20 ml, 24.1 mmol). Diphenyl chlorophosphate (2.00 ml, 9.65 mmol) was then added via syringe. The mixture was stirred under $N_2$ for 2 h at 50° C. at which point all of the etoposide had dissolved. Additional diphenyl chlorophosphate (1.80 ml, 8.68 mmol) was added and the reaction mixture was held at 45° C. for 72 h. After more of the amine base (0.75 ml) and diphenyl chlorophosphate (0.80 ml, 3.86 mmol) were added, the mixture was stirred at 40–45° C. for 27 h, treated with more diphenyl chlorophosphate (0.40 ml), and maintained at 40–45° C. for 22 h. Isopropanol (20 ml) was then added, the solvent was evaporated in vacuo, and the solid residue was dissolved in $CH_2Cl_2$ (500 ml), and partitioned with $H_2O$ (400 ml). The aqueous layer was further extracted with $CH_2Cl_2$ (100 ml) and the combined organic extracts were washed with brine (250 ml) and dried ($Na_2SO_4$/$MgSO_4$). Rotary evaporation followed by flash chromatography on silica gel using 2–3% $CH_3OH$ in $CH_2Cl_2$ provided 12.50 g (85%) of etoposide-4'-diphenyl phosphate as a colorless solid.

Next, platinum oxide (0.198 g, 0.87 mmol) from a freshly opened bottle (Aldrich Chemical Co.) was added to a solution of the etoposide 4'-diphenyl phosphate (0.79 g, 0.962 mmol) in 95 ml of absolute ethanol. The solution was hydrogenated on a Parr apparatus under 45–50 PSI for 4 h at room temperature. The reaction mixture was filtered through a pad of celite using ethanol as eluant. Concentration in vacuo and drying over $P_2O_5$ for 14 h in vacuo provided etoposide-4'-phosphate as a white solid (0.627, 94%):

FAB MS m/e 669 $(M+H)^+$

IR (KBr) 3440, 2930, 1778, 1604, 1498 $cm^{-1}$.

$^1H$ NMR (DMSO-$d_6$) δ 6.93 (s,1H), 6.46 (s,1H), 6.12 (s,2H), 5.94 (m,2H), 5.17 (bs,1H), 4.86 (d,J=3.93 Hz,1H), 4.64 (q,J=7.5,5.8 Hz,1H), 4.51–4.42 (m,2H), 4.20 (d,J=10.7 Hz,1H), 4.01 (dd,J=12.1, 5.3 Hz,1H), 3.51 (s,6H), 3.51–2.75 (m,7H), 2.83 (m,1H), 1.16 (d,J=5.1 Hz,3H).

$^{13}C$ NMR (DMSO-$d_6$) δ 174.5, 151.2, 151.1, 147.7, 146.2, 126.1, 132.3, 128.8, 109.8, 109.7, 107.9, 101.5, 101.2, 98.5, 80.0, 74.3, 72.7, 71.7, 67.6, 67.2, 65.7, 55.8, 43.0, 37.1, 20.2, 18.5.

Anal. Calcd. for $C_{29}H_{33}O_{16}P$. 0.85% $H_2O$: C,50.95; H, 5.11. Found: C,51.42; H,4.97.

The etoposide-4'-phosphate was then converted to its disodium salt by adding deionized $H_2O$ (50 ml) and solid sodium bicarbonate (3.00 g, 35.7 mmol) to 2.90 g (4.34 mmol) of the etoposide-4'-phosphate product. The mixture was stirred at room temperature for 0.5 h during which time the evolution of $CO_2$ ceased. This mixture was then applied directly to a C-18 column as described in the previous embodiment. The column was first eluted with 300 ml of deionized $H_2O$ to remove the excess salts and was then eluted with 4:1 $H_2O$/$CH_3OH$ to yield 1.90 g (61%) of pure etoposide 4'-phosphate disodium salt as a fluffy white solid following lyophilization.

The 4'-disodium phosphate or thiophosphate derivatives of etoposide represent highly water soluble prodrugs of etoposide with reduced cytotoxic activity. However, reaction of these compounds with alkaline phosphatase removes the phosphate or thiophosphate moiety, respectively, releasing the potent anti-cancer drug, etoposide (see FIG. 3).

Figure 5:
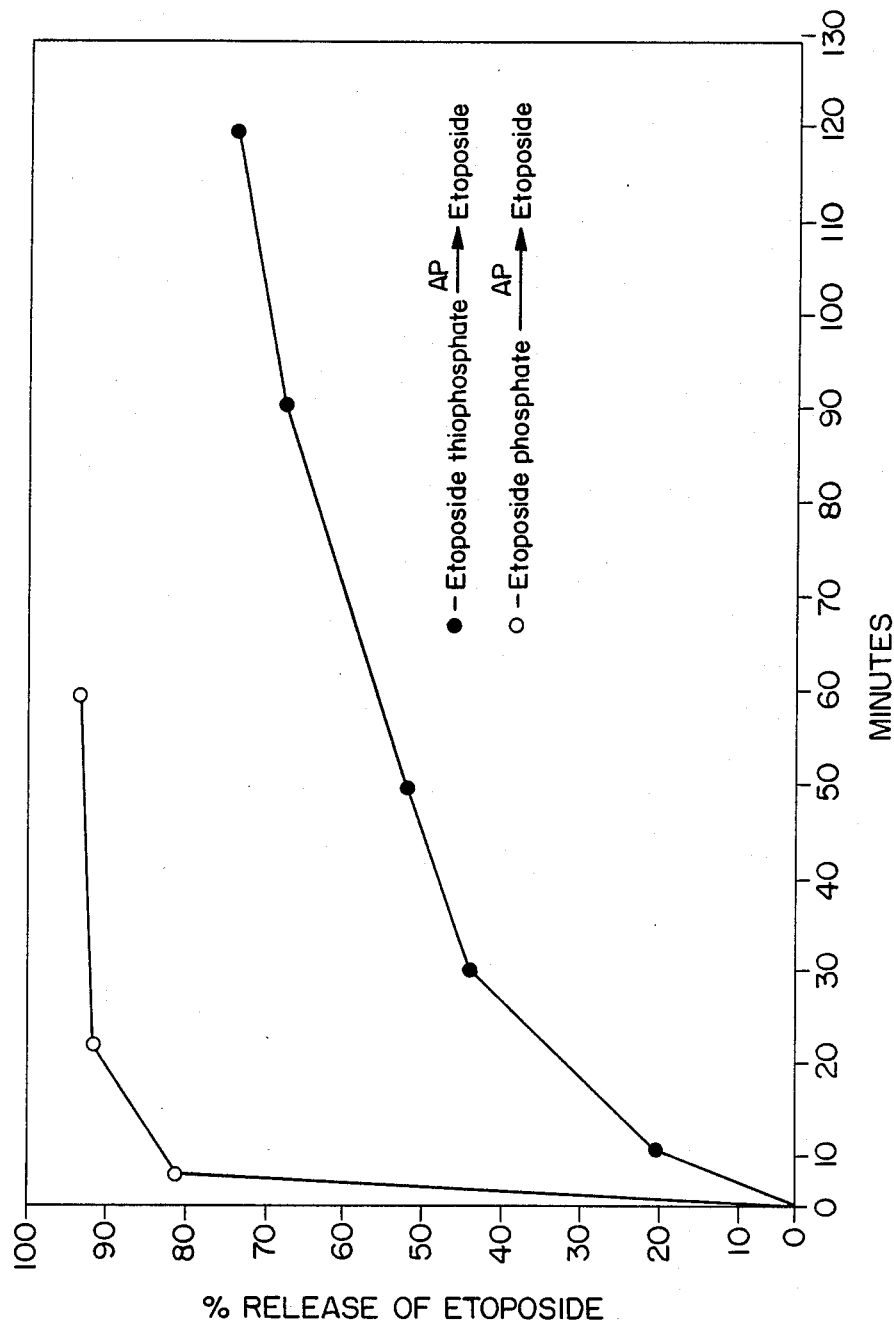
FIG. 5 is a comparative graphical presentation of the percentage of etoposide release over time upon exposure of etoposide-4'-phosphate or etoposide-4'-thiophosphate to alkaline phosphatase.

An experiment wherein etoposide-4'-phosphate and etoposide-4'-thiophosphate were each reacted with alkaline phosphatase indicated that both prodrugs are substrates for the enzyme. As FIG. 5 demonstrates, the etoposide phosphate is hydrolyzed by the enzyme more rapidly than the etoposide thiophosphate prodrug. However, the etoposide thiophosphate may, under certain conditions, have a particular utility due to its increased stability towards hydrolysis.

Reaction Of The Antibody-Alkaline Phosphatase Conjugates With An Etoposide Phosphate Prodrug The conjugates of this invention did not exhibit any apparent loss in enzymatic activity due to the attachment of the enzyme to the antibody as evidenced by the fact that the conjugates and free enzyme displayed equal activities on the substrates, p-nitrophenyl phosphate [see P. Tijssen, supra] or etoposide phosphate.

For example, either AP alone or the antibody-enzyme conjugate, L6-AP, produced as described above (final AP concentration 5 μg/ml) were added to a solution of etoposide-4'-phosphate (0.1 mM) in Tris buffer (100 mM) containing $MgCl_2$ (1 mM) and $ZnCl_2$ (0.1 mM) at pH 7.0. The reaction was monitored by HPLC using an IBM C-18 column (3 μ, 4.5×100 mm) and 50% aqueous methanol as eluant (0.5 ml/min, monitored at 254 nm). It was found that within 5 min of the start of the reaction, AP, whether in its free enzyme form or as part of the L6 antibody-enzyme conjugate, had effected the hydrolysis of at least 85% of the etoposide-4'-phosphate to etoposide (see FIGS. 4C and 4D). As the figures indicate, there was no loss in AP enzyme activity due to its attachment to the antibody in the conjugate. In the absence of enzyme, no phosphate hydrolysis occurred (see FIG. 4A). Aqueous solutions of etoposide phosphate or etoposide thiophosphate were stable for at least 8 hours at room temperature and for several days at 4° C.

Binding Of The Antibody-Alkaline Phosphatase Conjugates To H3347 Tumor Cells

Figure 6:
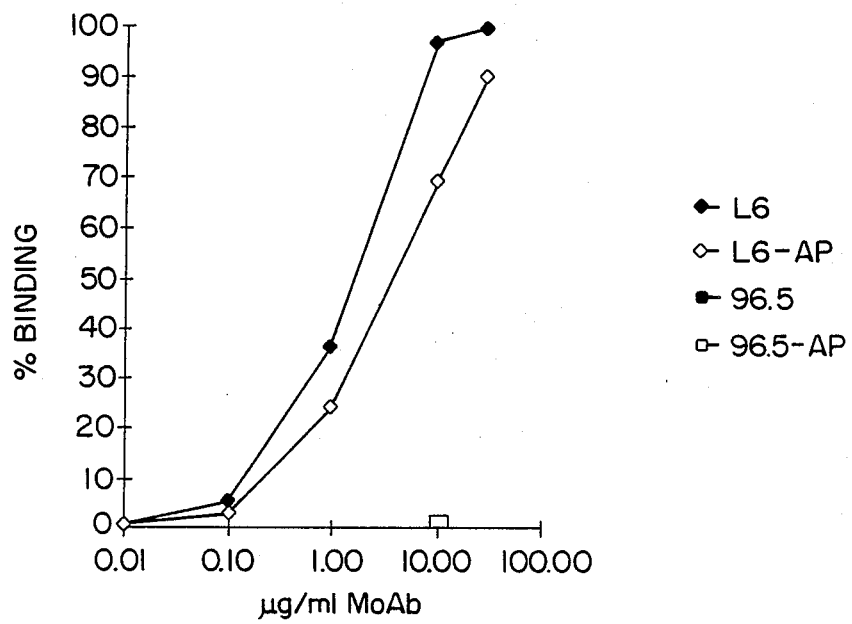
FIG. 6 depicts the comparative binding to H3347 tumor cells of the L6 and 96.5 monoclonal antibodies and the L6-AP and 96.5-AP conjugates of this invention.

FIG. 6 depicts the results of a conjugate binding assay performed to test the ability of the L6-AP and 96.5-AP conjugates as well as the free L6 and 96.5 antibodies to bind to tumor cells from the metastatic human colon carcinoma cell line, H3347 (provided by Judy Anderson, Oncogen).

The binding assay was performed as follows: the immunoconjugates or free antibodies were serially diluted in incomplete modified Delbecco's medium (IMDM, Gibco) and 100 μl aliquots were incubated at 4° C. with $10^6$ cells for 30 min.

The cells were washed and incubated with 50 μl of FITC-goat anti-mouse antibody (Tago, diluted 1:12.5) for an additional 30 min at 4° C. Cells were washed and analyzed on a Coulter Epics-C fluorescence cell analyzer. Dead cells were gated out and the mean log green fluorescent intensity of each sample was obtained. This number was converted to a linear scale and ratios between the negative control (cells+FITC-goat anti-mouse antibody) and all test samples were calculated.

FIG. 6 demonstrates that most of the binding ability of the antibodies was preserved in the conjugates, i.e., conjugation did not affect the antibodies' binding ability. Furthermore, the figure shows the specificity of binding of the antibodies, i.e., that both the 96.5 free antibody and the 96.5-AP conjugate bound much more weakly to the tumor cells than the L6 antibody and L6-AP conjugate. This result may be expected when it is considered that the H3347 tumor cells are from a human carcinoma and the L6 antibody is specific for a carcinoma antigen while the 96.5 antibody is specific for a melanoma antigen.

Figure 7:
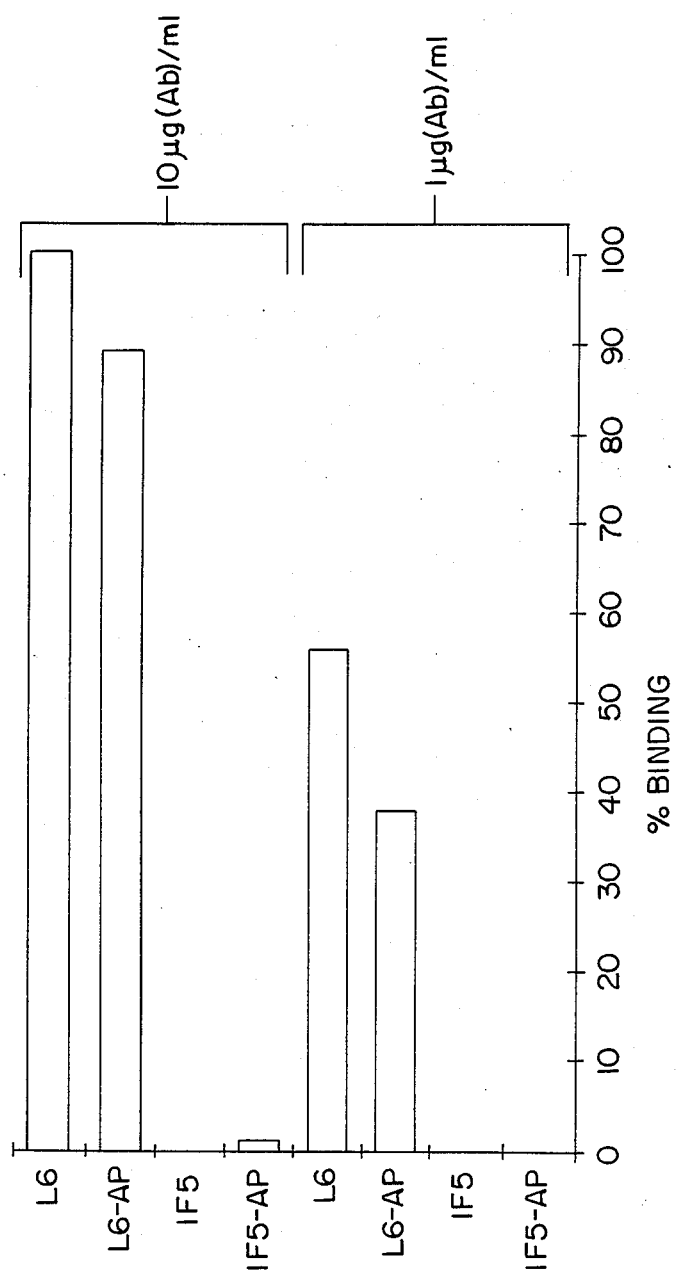
FIG. 7 depicts the comparative binding to H3347 tumor cells of the L6 and 1F5 monoclonal antibodies and the L6-AP and 1F5-AP conjugates of this invention.

Similar binding experiments using L6, L6-AP, 1F5 and 1F5-AP also showed that L6 and L6-AP bound to the H3347 carcinoma cell line (saturation at 10 μg/ml antibody) while very little or no detectable binding by 1F5 or 1F5-AP was observed (see FIG. 7). This result demonstrated again the specificity of binding of the conjugates, with the L6-AP conjugate binding to the L6-positive tumor cell line and the 1F5-AP conjugate, with a specificity for B lymphoma cells, showing no binding.

In Vitro Cytotoxicity Of A Conjugate/Prodrug Combination Of The Invention

Next, the cytotoxic effect of the conjugate/prodrug combinations of this invention was demonstrated in vitro using either a clonogenic cytotoxicity assay or a $^3$H-thymidine uptake assay.

The clonogenic cytotoxicity assay we used was the colony inhibition assay described by I. Hellstrom et al., "Colony Inhibition And Cytotoxicity Assays," in *In Vitro Methods In Cell-Mediated Immunity*, Bloom and Glade (ed.s), pp. 409–14 (1971). The cells used to detect cytotoxicity were the H3347 tumor cells described above. Both the L6-AP and 96.5-AP conjugates were tested for their ability to convert prodrug into the free drug.

Briefly, the H3347 cells ($10^6$/ml) were suspended in IMDM growth media (containing 10 μg/ml of each immunoconjugate based on antibody concentration) and incubated for 30 min at 37° C. The cells were washed twice, resuspended in IMDM, and the drug or prodrug in medium was added. Incubation at 37° C. was continued for 15 hours. After washing twice, the cells were plated out and the number of colonies (>8 cells/-colony) were counted 7-10 days later.

Figure 8:
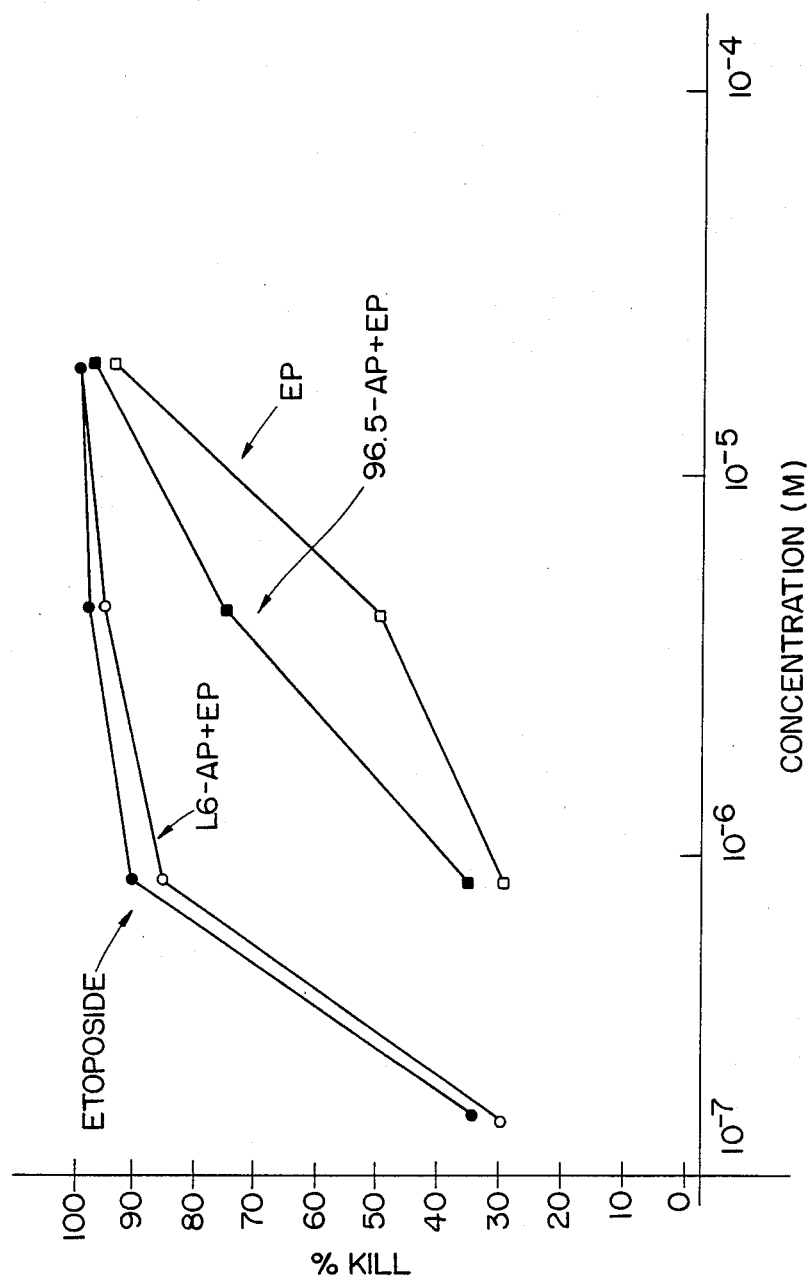
FIG. 8 is a comparative graphical presentation of the percentage of tumor cells killed vs. molar concentration of etoposide or the etoposide phosphate prodrug. The graph depicts the increased percentage killing that results from the reaction of the relatively non-cytotoxic prodrug with either the L6-AP conjugate or the 96.5-AP conjugate of the invention.

The results of the assay are shown in FIG. 8 (the percent inhibition is the average of six samples). As shown in the figure, etoposide ($IC_{50}$=0.20 μM) was much more cytotoxic than the etoposide-4'-phosphate (EP) ($IC_{50}$=5.8 μM). The prodrug alone showed very little cytotoxic activity. Treatment of the H3347 cells with the L6-AP conjugate, followed by exposure to etoposide phosphate, resulted in a very large increase in cytotoxic activity over that seen with the prodrug alone, the increased cytotoxic activity being comparable to the cytotoxic activity seen with etoposide alone. Treatment of the cells with the 96.5-AP conjugate and etoposide phosphate showed a much smaller increase in cytotoxic activity over that seen with the prodrug alone. This result may be attributable to the small amount of 96.5-AP conjugate that binds to the H3347 cells as discussed above (see FIG. 6). The conjugates are not themselves cytotoxic since treatment of the cells with the conjugates alone did not cause any cell death.

The cytotoxic effect of the conjugates of this invention was also studied using a $^3$H-thymidine uptake assay. According to this assay, a suspension of $10^6$ H3347 tumor cells in 0.1 ml of IMDM with 10% fetal calf serum was incubated for 1 h at 4° C. in the presence of 5 μg/ml of conjugate. The cells were washed twice with the medium containing 10% fetal calf serum, resuspended (in 1 ml) and plated into 96-well microtiter plates (10,000 cells/well). The drug or prodrug in IMDM was then added and incubation at 37° C. was commenced for 6 h. The cells were washed twice and the incubation was continued an additional 12 h, followed by a 6 h pulse with $^3$H-thymidine (1.0 μCi/well). The plates were frozen at −20° C. to detach the cells and the cells were harvested onto glass fiber discs. The filters were counted on a Beckman 3801 scintillation counter.

Figure 9:
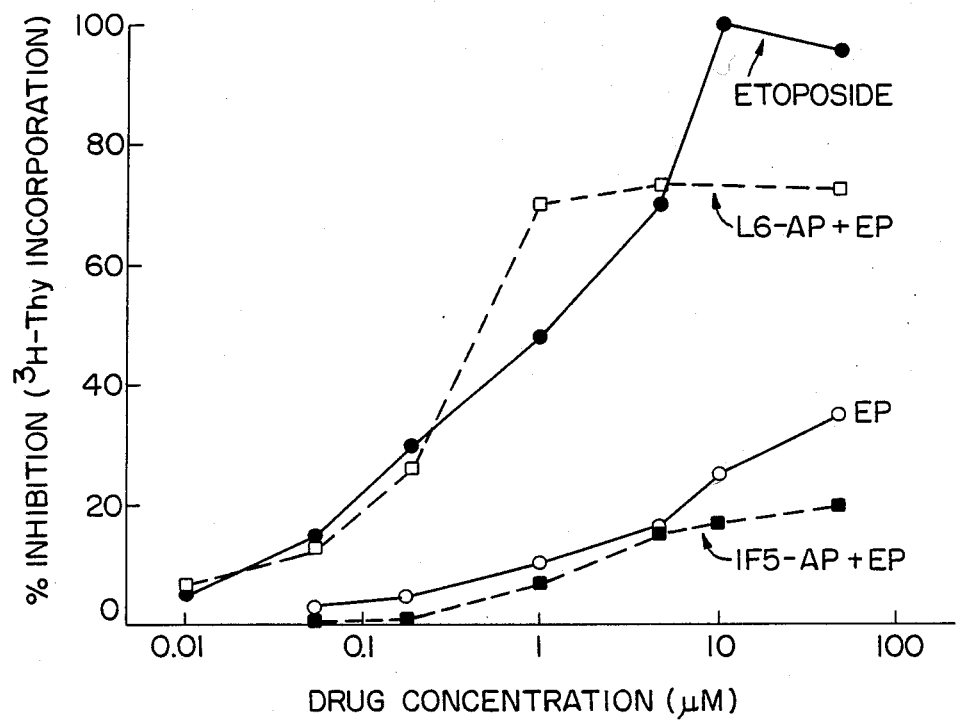
FIG. 9 is a comparative graphical presentation of the percent inhibition of $^3$H-thymidine incorporation into the DNA of H3347 tumor cells treated with ●: etoposide, O: EP, □: L6-AP+EP or ■: 1F5−AP+EP. The graph depicts the increase in cytotoxic activity observed when the tumor cells were treated with L6-AP and EP as compared to the activity seen upon treatment with EP alone.

Using this assay, we measured the inhibition of $^3$H-thymidine incorporation into the DNA of the tumor cells and thus, the cytotoxic effect of etoposide or the prodrug, EP, on the cells in the absence or presence of the L6-AP or 1F5-AP conjugates. As shown in FIG. 9, etoposide ($IC_{50}$=1 μM) was more than 100-fold more toxic than EP (35% inhibition at 100 μM). Pretreatment of the cells with 1F5-AP prior to EP exposure resulted in no enhancement of cytotoxicity. However, a dramatic increase in cytotoxic activity was observed when the cells were first exposed to L6-AP and then to EP. Thus, in both assays used to determine in vitro cytotoxicity, the cytotoxic effect of the conjugate/prodrug combination of this invention was comparable to that of etoposide alone, and this effect was antigen-specific, as indicated by the fact that EP cytotoxicity was not similarly enhanced by treatment of the H3347 cells with the control conjugates, 96.5-AP and 1F5-AP, respectively.

Localization Of The Conjugates In Tumor Xenografts In Mice

In vivo localization studies were undertaken next to find out how rapidly and to what extent the conjugates of the invention accumulated in a tumor. This information would prove useful in determining an appropriate interval of time between the administration of the antibody-enzyme conjugate and the prodrug in our tumor therapy studies.

First, Balb/C nu/nu female mice (4-6 wk old) (obtained from Life Sciences, St. Petersburg, Fla.) were injected with $10^7$ H3347 tumor cells subcutaneously (s.c.) in the left and right hind flanks. The tumor cells were obtained from in vitro cultures that had been suspended by treatment for 2 min with trypsin (0.5 g/l) and EDTA (0.2 g/l). The cells were washed twice with IMDM and incubated for 1 h at 37° C. in IMDM with 10% fetal calf serum. The cells were washed, suspended in PBS, and kept at 4° C. prior to injection. Both the localization and therapy studies described herein were initiated when the tumors reached an average size of 225 mm$^3$.

For our localization studies, L6 and L6-AP were labeled with $^{125}$I and 1F5 and 1F5-AP were labeled with $^{131}$I, using the iodogen method [see P. J. Fraker et al., *Biochem. Biophys. Res. Commun.*, 80, pp. 849–857 (1978)]. Two days prior to the localization experiments, the animals were put on 0.5% (v/v) Lugol's iodine solution. Each mouse was injected i.p. with 100 μg (based on each monoclonal antibody) of either of the following solutions: L6-AP (5 μCi) and 1F5-AP (2.5 μCi) in 0.2 ml of PBS at pH 7.2 or a combination of L6 (5 μCi) and 1F5 (2.5 μCi) in 0.2 ml of PBS. At periodic intervals, the mice were anesthetized, bled through the orbital plexis and sacrificed. Tissues were weighed and then counted on a gamma counter. Localization was determined by comparing $^{125}$I-L6 localization with that of $^{131}$I-1F5, i.e., by determining the ratios of specific ($^{125}$I) to non-specific ($^{131}$I) uptake of counts in various tissues. The results for tumor and liver uptake are summarized in Table 1 below.

TABLE 1

| | PERCENT INJECTED DOSE PER GRAM TISSUE WEIGHT OF ADMINISTERED PROTEINS | | | |
|---|---|---|---|---|
| | L6 | | L6-AP | |
| | tumor | liver | tumor | liver |
| 2 hours | 1.6 (8.0) | 4.9 (2.0) | 1.5 (7.5) | 5.2 (0.7) |
| 24 hours | 3.6 (12.0) | 2.3 (1.4) | 1.0 (10.0) | 1.3 (1.3) |
| 48 hours | 4.0 (8.0) | 2.5 (1.3) | 0.5 (5.0) | 0.8 (1.0) |

Numbers in parentheses represent ratios of L6/1F5 or L6-AP/1F5-AP.

As the table indicates, unconjugated L6 localized efficiently to the tumor within 24h and remained there for at least 48 h. During this period, the ratio of L6 to 1F5 in the tumor ranged from 8-12, while the ratio in the liver was quite low (1.3-1.4). The maximum level of specific uptake in the tumor for L6-AP occurred at approximately 24 h, at which point the ratio of L6-AP to 1F5-AP was 10.0. These results indicate that the L6-AP conjugate localized within the tumor far better than did 1F5-AP, but not as well as unmodified L6.

Figure 10A:
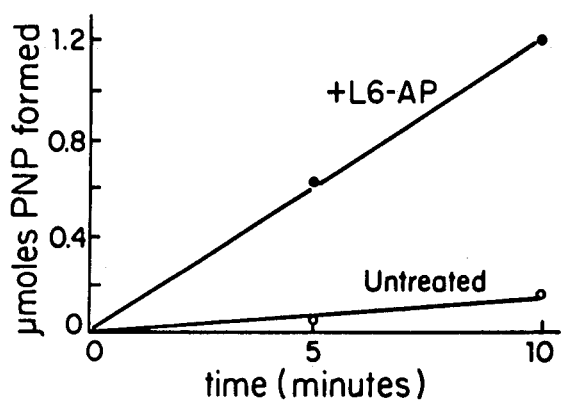
FIG. 10A depicts the total phosphatase activity of H3347 tumors over time in untreated mice vs. mice treated 24hours earlier with the L6-AP conjugate of the invention.

Next, we determined the amount of natural phosphatase activity in the tumor and the degree to which this activity could be raised by targeting AP to the tumor using the conjugates of this invention. Tumors were excised from mice that had been treated for 24 h with 100 μg (based on L6) of L6-AP and the total phosphatase activity was measured, using p-nitrophenyl phosphate as a substrate as follows: The excised tumor was washed and then gently rotated at 23° C. with p-nitrophenyl phosphate (1 mg/ml) in pH 9.5 Tris (100 mM) containing NaCl (100 mM) and $MgCl_2$ (5 mM). The course of the reaction was monitored by measurement of the p-nitrophenol released at 410 nm and the results were corrected for tumor weight. It was found that tumors from mice that had received the L6-AP conjugate displayed as much as 10 times the level of phosphatase activity observed in tumors from untreated mice (see FIG. 10A).

A more detailed histological analysis of the phosphatase activity of the tumor was undertaken on cross-sections of tumors obtained from mice that had been untreated or previously treated 24 h earlier with 300 μg (based on antibody) of either L6-AP or 1F5-AP. Phosphatase activity was estimated by immunohistology, using a phosphatase substrate that deposited a dark precipitate at the site of enzyme activity as follows: Excised tumors were quickly frozen to −28° C. and 8 μm sequential cross-sections were made using a Reichert-Jung microtome. The phosphatase activity was measured with an AP substrate kit from Vector Laboratories (Burlingame, Calif.) and the results were compared to sections that were stained with hematoxylin and eosin (H. and E., see FIG. 10B).

Figure 10B:
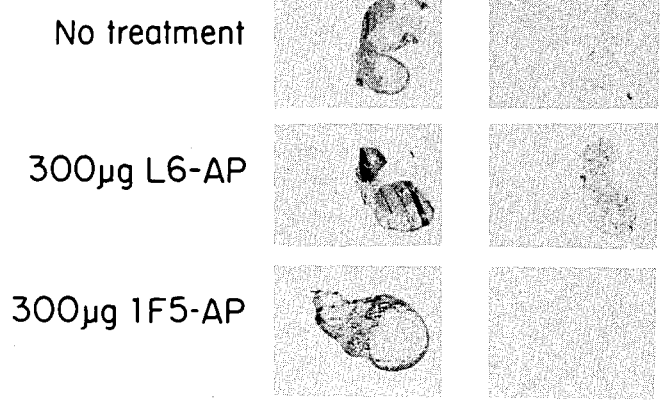
FIG. 10B shows tumor cross-sections from untreated or L6-AP or 1F5-AP-pretreated mice stained either with hematoxylin and eosin or with an AP substrate. Dark areas indicate high phosphatase activity.

As FIG. 10B demonstrates, little enzyme activity was detected in tumors from mice that were untreated or treated with 1F5-AP. However, in mice that received L6-AP, phosphatase activity was highly elevated and could be seen distributed throughout the tumor. Microscopic evaluation revealed that most of the tumor cells in the L6-AP treated mice stained highly positive for phosphatase activity.

In Vivo Antitumor Effect Of A Conjugate/Etoposide Phosphate Prodrug Combination Of The Invention Therapy experiments were performed on nude mice that had s.c. tumors approximately 225 mm³ in volume. The conjugates, L6-AP and 1F5-AP, were administered (i.p.) 18-24 h prior to treatment with EP. Tumor growth was compared to that in untreated mice and in mice treated with maximum tolerated doses of etoposide or EP alone.

More particularly, a group of 8 nude mice with bilateral H3347 tumors was treated with either etoposide (0.2 ml containing 1.2 mg etoposide in 2:3 DMSO:$H_2O$) or EP (0.2 ml containing 2 mg EP in $H_2O$) alone or with L6-AP (0.1 ml containing 300 μg antibody in PBS) or 1F5-AP (0.1 ml containing 300 μg antibody in PBS) followed by EP treatment Each experiment contained a control group of mice that was untreated. Tumor volumes were estimated at various days post tumor implant, using the formula:

[(perpendicular width $^2/2$)] × longest length

Figure 11:
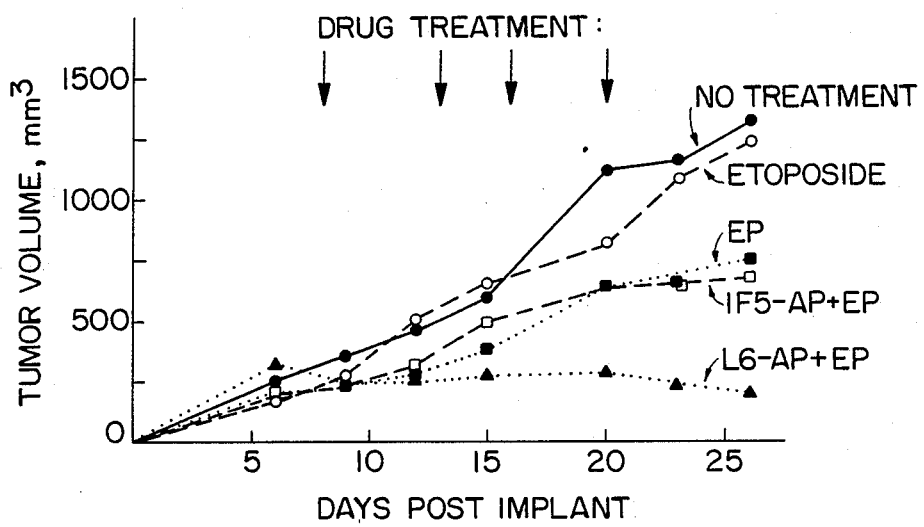
FIG. 11 is a comparative graphical presentation of tumor volume over time in mice ●: untreated or treated with O: etoposide, ■: EP, □: 1F5-AP+EP or ▲: L6-AP+EP. Arrows indicate the start of drug treatment and where applicable, the conjugates were administered b 18–24 hours earlier. The graph depicts the pronounced antitumor effect observed upon treatment with L6-AP and EP.

The results of these experiments are shown in FIG. 11. Etoposide had very little effect on tumor growth at the dose used and higher doses were not well tolerated. The prodrug, EP, was less toxic to the animals, and the higher dose that could therefore be administered resulted in a greater antitumor effect than seen with etoposide itself. A similar degree of antitumor activity was observed in mice receiving the control conjugate, 1F5-AP, prior to treatment with EP. However, when the mice were treated with L6-AP followed by EP, a much more pronounced antitumor effect was observed. L6-AP alone had no effect on tumor growth (data not shown).

A summary of the responses of each individual tumor to the therapy is shown in Table 2 below. Out of 16 tumors in the 8 mice treated with L6-AP and EP, 6 tumors underwent complete regression and 2 others became smaller in size than at the start of treatment. No complete or partial responses were observed in any of the other treatment protocols.

TABLE 2

EFFECT OF VARIOUS TREATMENTS ON TUMOR GROWTH

| Agent | RESPONSE* | | | |
|---|---|---|---|---|
|  | progression | stable | partial | complete |
| None | 16 | 0 | 0 | 0 |
| Etoposide | 12 | 4 | 0 | 0 |
| EP | 6 | 10 | 0 | 0 |
| 1F5-AP + EP | 9 | 7 | 0 | 0 |
| L6-AP + EP | 3 | 5 | 2 | 6 |

Data represents responses of 16 tumors in each group 23 days after tumor implant.
*Response: progression - continued tumor growth; stable - no additional tumor growth; partial - decrease in size; complete - regression leading to no apparent tumor.

The present example clearly demonstrates the applicability of the method of this invention for the delivery of a cytotoxic antitumor drug to tumor cells using a tumor-specific antibody-enzyme conjugate and a prodrug capable of being converted by the enzyme from a relatively non-cytotoxic to a potent, cytotoxic form.

EXAMPLE 2

This example demonstrates the use of the immunoconjugates and methods of this invention to convert a relatively non-cytotoxic mitomycin phosphate prodrug into an active mitomycin drug, leading to in vitro cytotoxicity toward tumor cells. Furthermore, as was demonstrated in Example 1 above, the following example demonstrates the applicability of the immunoconjugates, prodrugs and methods of this invention for the delivery of a cytotoxic antitumor drug to tumor cells in vivo.

This example utilizes the L6-AP and 1F5-AP immunoconjugates prepared as described in Example 1 above. According to this embodiment of the invention, each of these antibody-enzyme conjugates was reacted with a novel mitomycin phosphate prodrug. More particularly, the prodrug utilized was a disodium salt of an $N^7$—$C_{1-8}$ alkyl phosphate of mitomycin C. The antitumor agent released as a result of this reaction was a mitomycin alcohol derivative. The L6-AP/mitomycin phosphate prodrug combination of this invention resulted in cytotoxicity toward tumor cells in vitro and a pronounced in vivo antitumor effect in mice.

Preparation Of A Novel Mitomycin Phosphate Prodrug

The novel mitomycin phosphate prodrug, 7-(2'-aminoethyl phosphate)mitomycin (referred to hereinafter as "MOP") is the 2-aminoethyl phosphate derivative of mitomycin C ("MMC") and was prepared as follows:

A solution of 2-aminoethyl dihydrogen phosphate (56 mg, 0.4 mmol) in water (0.35 ml) and triethylamine (0.3 ml, 2 mmol) was added to mitomycin A (referred to hereinafter as "MMA") (140 mg, 0.4 mmol) in methanol (6 ml) and the reaction was allowed to proceed at room temperature overnight. 1.4 ml of saturated aqueous sodium bicarbonate was then added and the solution was partitioned between water and methylene chloride. The aqueous phase was concentrated to dryness and several portions of methanol were added and evaporated. The residue was taken up into methanol, filtered, and applied to a 2×10 cm C-18 (reverse phase) silica column. The product was eluted with water and all volatile material was evaporated. Methanol was added and evaporated as before and the residue was dried for 24 h under high vacuum in a desiccator with phosphorus pentoxide. The mitomycin phosphate derivative, MOP, was obtained as a fine blue powder (190 mg, 97%).

360 MHz $^1$H-NMR (D$_2$O) $\delta$ 1.94 (s, 3H, CH$_3$), 2.9–3.1 (m, 4H), 3.20 (s, OCH$_3$), 3.28 (s, 1H), 3.36 (s, 1H), 3.5–3.65 (m, 4H), 4.1–4.25 (m, 2H), 4.50–4.57 (dd, 1H, 10-H).

Figure 12:
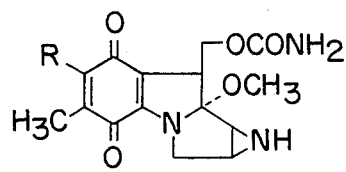
FIG. 12 depicts the chemical structures of the mitomycin derivatives used according to this invention, including the novel prodrug, 7-(2'-aminoethyl phosphate)mitomycin ("MOP").

Thus, MOP was prepared by displacement of the 7-methoxy group of MMA with 2-aminoethyl phosphoric acid (see FIG. 12). The product was converted to the water soluble disodium salt upon treatment with sodium bicarbonate.

The corresponding known mitomycin alcohol derivative, 7-[(2-hydroxyethyl)amino]-9a-methoxymitosane (referred to hereinafter as "MOH") was prepared by reacting MMA (100 mg, 0.286 mmol) with ethanolamine (26 mg, 0.429 mmol) according to the method of B. S. Iyengar et al., "Mitomycin C and Porfiromycin Analogues With Substituted Ethylamines At Position 7", *J. Med. Chem.*, 26, pp. 16–20 (1983). The product was obtained as a fine blue powder (58 mg, 54%).

Reactivity And Stability Of The Mitomycin Phosphate Prodrug

Figure 13:
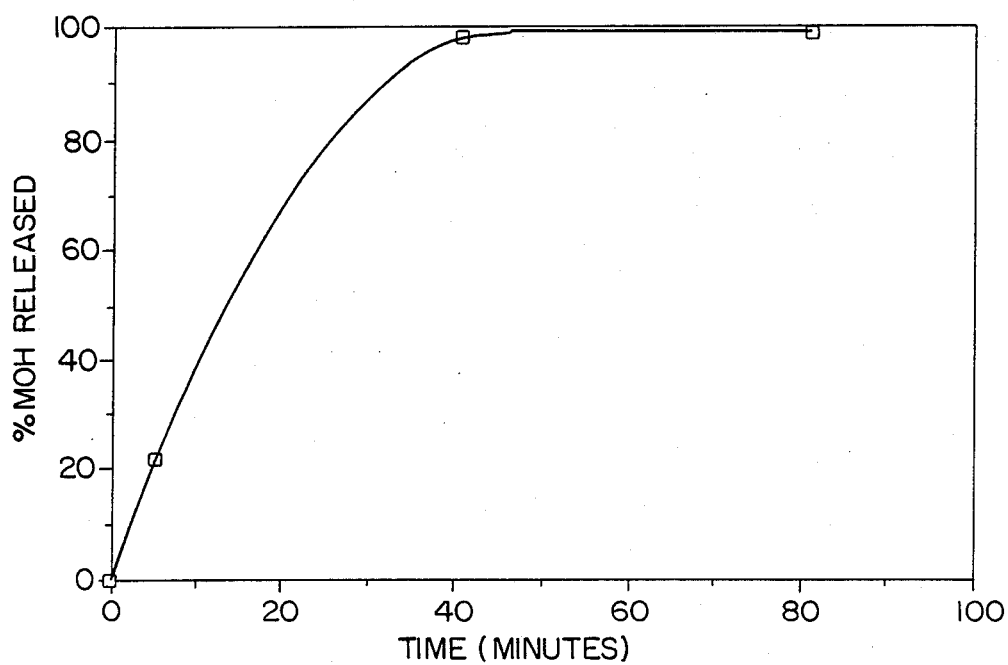
FIG. 13 depicts the reaction of MOP with the alkaline phosphatase enzyme over time. The course of the reaction was monitored by HPLC for the release of MOH, the mitomycin alcohol derivative of MOP.

The MOP prodrug was then tested for its reactivity with AP. To a solution of MOP (1 mM) in 100 mM Tris, pH 7.2 buffer at room temperature was added either calf intestinal or human placental AP (final conc. 1 $\mu$g/ml). The course of the reaction was monitored by HPLC using a C-18 column (4.6×150 mm) and the following conditions: detection at 280 nm; 30–95% methanol in acetate buffer (100 mM, pH 5.2) over 8 min, re-equilibration after 15 min; 0.8 ml/min flow rate. Under these conditions, MMC eluted at 7.0 min, MOH eluted at 8.5 min, and MOP eluted 4.0 min. As demonstrated in FIG. 13, the phosphate group on the MOP prodrug was rapidly cleaved with AP. HPLC served to confirm that the corresponding alcohol, MOH, was formed. Under the reaction conditions used, the half life for hydrolysis of MOP was about 10 min and the reaction went to completion within 40 min.

The stability of MOP and EP in human serum was determined using HPLC by measuring both the rate of disappearance of the prodrugs and the rate of formation of MOH and etoposide. Thus, for example, a solution of MOP (1 mM in 100 mM Tris, pH 7.2) was added to fresh human serum so that the final drug concentration was 0.1 mM. Aliquots (0.25 ml) were diluted with methanol (0.25 ml) and EDTA (50 $\mu$l at 100 mM) to precipitate the serum proteins and stop the reaction. The samples were centrifuged and analyzed by HPLC as described immediately above. It was found that 50% hydrolysis of EP took place after 1 h, but that only 25% of the MOP hydrolyzed after 4 h. Complete hydrolysis could be rapidly achieved by adding AP to the serum.

Binding Of The Antibody-Alkaline Phosphatase Conjugates To H2981 Tumor Cells The ability of the L6-AP and 1F5-AP antibody-enzyme conjugates of the invention to bind to H2981 tumor cells was then measured. The H2981 cell line was established from a primary human adenocarcinoma of the lung [see, I. Hellstrom et al., "Monoclonal Mouse Antibodies Raised Against Human Lung Carcinomas", *Cancer Res.*, 46 (No. 8), pp. 3917–23 (1986)]. The L6 antibody is known to bind strongly to H2981 cells (saturation at 10 $\mu$g/ml) while 1F5 shows very little binding to these cells.

Figure 14:
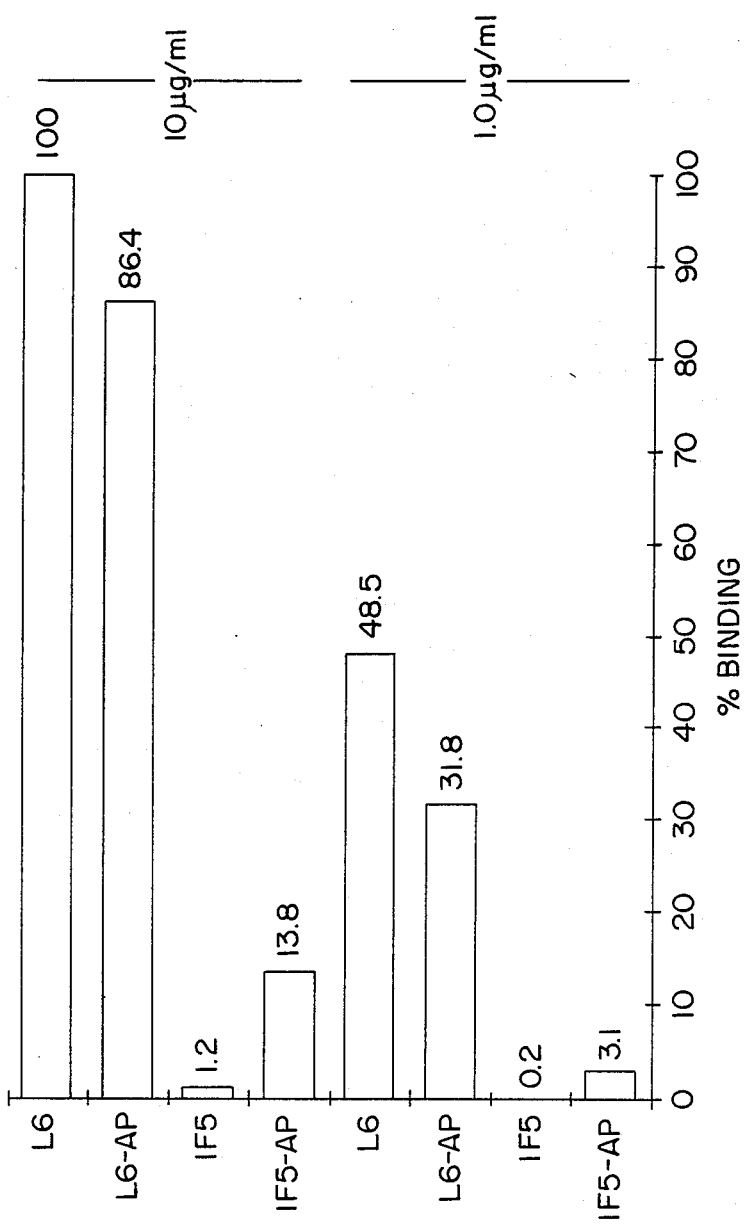
FIG. 14 depicts the comparative binding to H2981 tumor cells of the L6 and 1F5 monoclonal antibodies and the L6-AP and 1F5-AP conjugates of this invention.

The binding assay was performed as described in Example 1. FACS analysis indicated that L6 and L6-AP bound strongly to the cells, while much weaker binding was displayed for 1F5 and 1F5-AP (see FIG. 14).

In Vitro Cytotoxicity Of The Conjugate/Prodrug Combination Of The Invention On H2981 Tumor Cells The cytotoxic effect of the conjugate/prodrug combinations of this invention was demonstrated in vitro via the $^3$H-thymidine uptake assay described in Example 1; in this case using H2981 tumor cells to test for in vitro cytotoxicity and using CEM cells as a control. The T cell ALL cell line, CEM, was obtained from the ATCC and does not bind the L6 or 1F5 monoclonal antibodies. The cytotoxic effects of the prodrugs, EP and MOP, on the tumor cells in the absence or presence of the L6-AP or 1F5-AP immunoconjugates were analyzed. The cytotoxic effects of these combinations were also compared to the cytotoxic effect of each parent drug alone.

Figure 16:
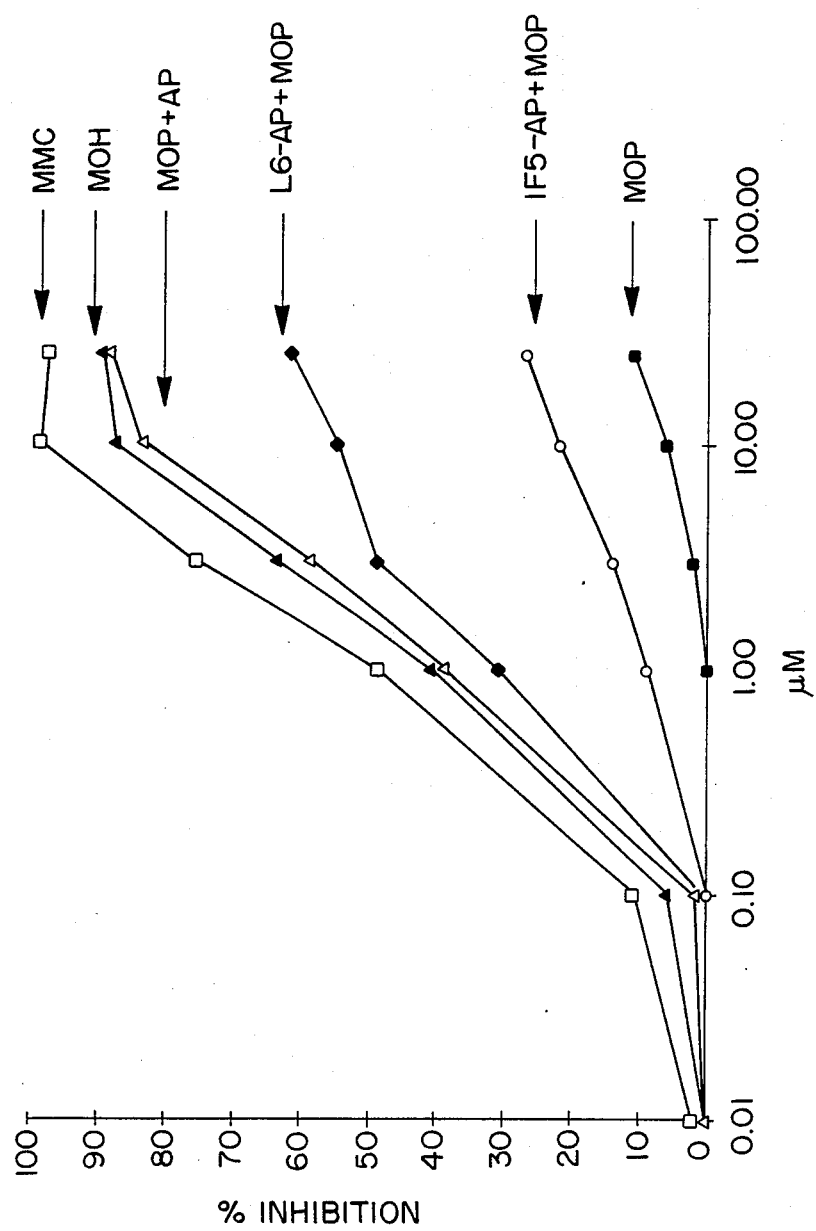
FIG. 16 is a comparative graphical presentation of the percent inhibition of $^3$H-thymidine incorporation into the DNA of H2981 tumor cells treated with □: mitomycin C (MMC), ▲: MOH, ■: MOP, Δ: MOP+AP, ●: L6-AP+MOP or O: 1F5-AP+MOP. The graph depicts the increase in cytotoxic activity observed when the tumor cells were pretreated with the L6-AP conjugate of the invention followed by MOP treatment as compared to the activity seen upon treatment with MOP alone.
Figure 17:
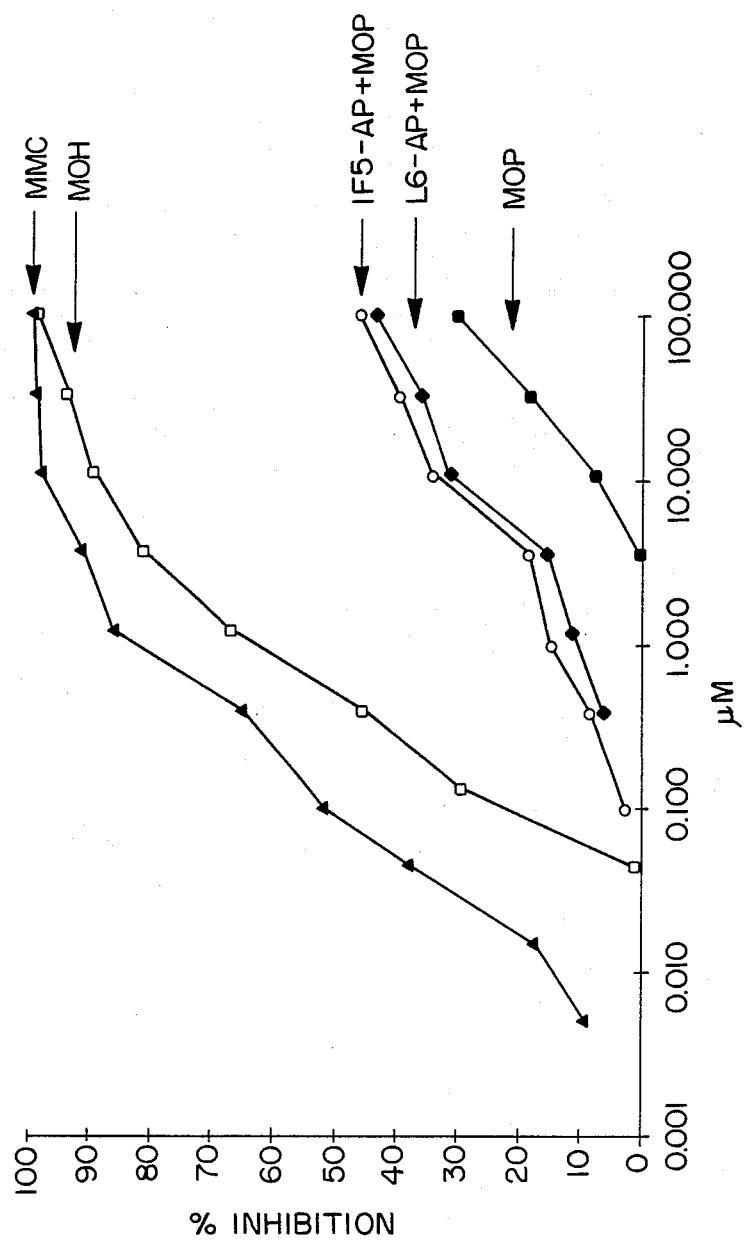
FIG. 17 is a comparative graphical presentation of the percent inhibition of $^3$H-thymidine incorporation into the DNA of CEM cells treated with ▲: MMC, □: MOH, ■: MOP, ●: L6-AP+MOP or O: 1F5-AP+MOP. This graph demonstrates the specificity of the enhanced cytotoxicity seen in FIG. 16 above because a significant enhancement is not seen on CEM cells that lack the L6 antigen.

Briefly, a suspension of 10$^6$ H2981 or CEM cells in 0.1 ml of IMDM containing 10% fetal calf serum was incubated for 1 h at 4° C. in the presence of 10 $\mu$g/ml of conjugate. The cells were washed twice with the medium containing 10% fetal calf serum, resuspended in 1 ml of phosphate buffered saline, pH 7.2 (PBS) and plated into 96-well microtiter plates (10,000 cells/well). The prodrug in PBS was then added and incubation at 37° C. was commenced for 1 h (for MOP) or 5 h (for EP). The cells were then washed twice and incubation was continued for a total of 24 h (including a 6 h pulse with $^3$H-thymidine, 1.0 $\mu$Ci/well). The plates were frozen at −70° C. to detach the cells and after thawing, the cells were harvested onto glass fiber discs. The filters were counted on a Beckman 3801 scintillation counter and the cytotoxic effects of the conjugate/prodrug combinations were compared to the cytotoxicity seen upon treatment of the cells with the prodrug or parent drug alone. The results are shown in FIGS. 15–17.

Figure 15:
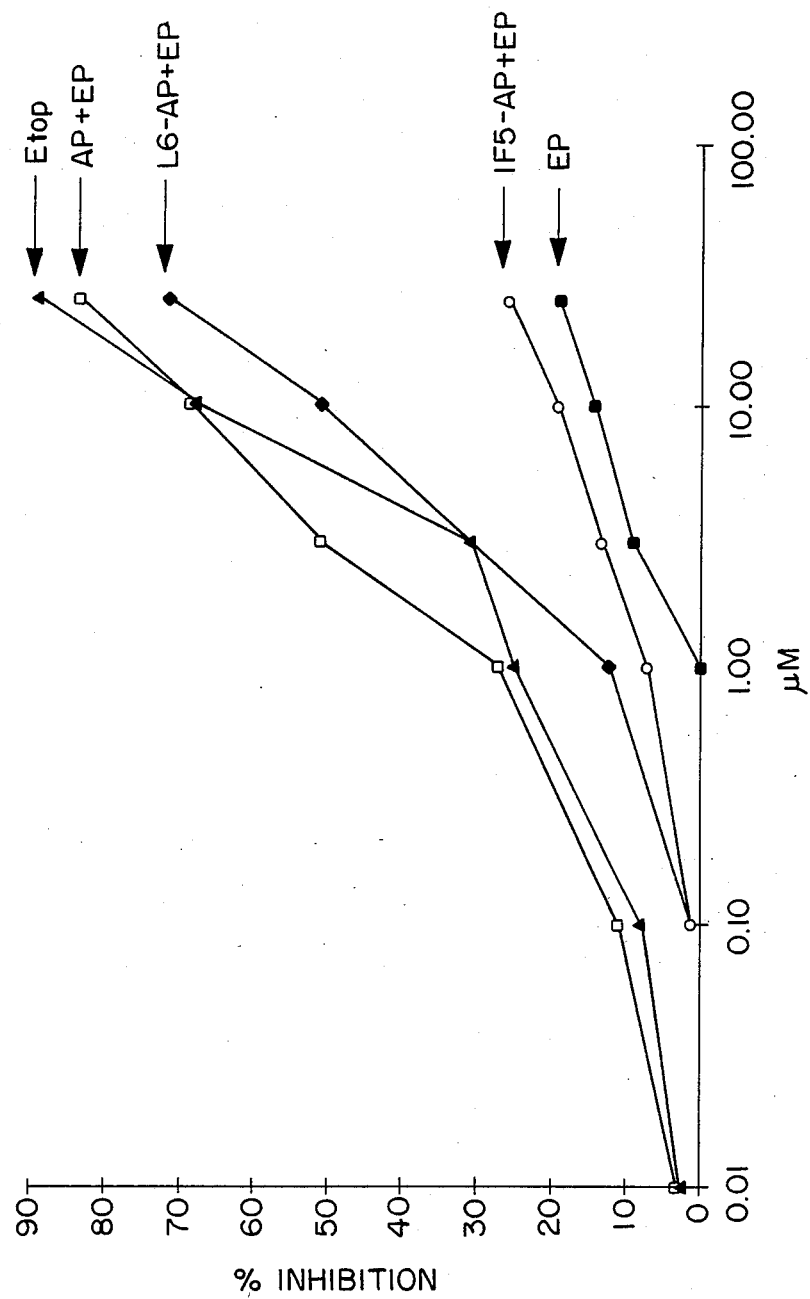
FIG. 15 is a comparative graphical presentation of the percent inhibition of $^3$H-thymidine incorporation into the DNA of H2981 tumor cells treated with ▲: etoposide, ■: EP, □: AP+EP, ●: L6-AP+EP or O: 1F5-AP+EP. The graph depicts the increase in cytotoxic activity over EP alone observed when the tumor cells were pretreated with the L6-AP conjugate of the invention.

As shown in FIG. 15, etoposide (IC$_{50}$ of 2 $\mu$M) was significantly more toxic to the H2981 cells than EP (20% kill at 30 $\mu$M). Pretreatment of the cells with 1F5-AP prior to prodrug exposure resulted in a very slight enhancement of cytotoxicity. However, a dramatic increase of cytotoxic activity was observed when the cells were first exposed to L6-AP and then to EP. The cytotoxic effect was comparable to that of etoposide alone.

A similar result was observed using mitomycin derivatives. As indicated in FIG. 16, MMC and MOH were equally cytotoxic towards H2981 cells and had $IC_{50}$ values of about 1 $\mu M$. The phosphate prodrug, MOP, was much less cytotoxic (5% cell kill at 10 $\mu M$), probably owing to its inability to penetrate the cell. However, the activity of MOP was comparable to MOH and MMC when the tumor cells were pre-exposed to the L6-AP conjugate of the invention. This enhancement was antigen specific, since the non-binding conjugate, 1F5-AP, did not significantly affect the cytotoxic activity of the prodrug. Neither L6-AP nor 1F5-AP dramatically enhanced the cytotoxic effect of MOP against CEM cells, consistent with the fact that the conjugates do not bind to this cell line (see FIG. 17). Thus, these results indicate that the phosphate group of each of the tested prodrugs inactivates the drug and that upon hydrolysis of that phosphate group by an antibody-enzyme conjugate bound to the tumor cell surface, either of the prodrugs, EP and MOP, yield active cytotoxic drugs.

In Vivo Antitumor Effect Of The Conjugate/Mitomycin Prodrug Combination Of The Invention Prior to investigating the in vivo antitumor activity of MOP in combination with the L6-AP conjugate of the invention, the relative toxicities of the prodrug and its released active derivative, MOH, were determined in Balb C nu/nu mice. When the drugs were administered (i.p.) in two equal doses spaced 4 days apart, $LD_{50}$ values of 45 and 90 mg drug/kg body weight were obtained for MOH and MOP, respectively. It was also found that considerably more drug could be administered using smaller doses over a longer period of time. Total amounts of up to 40 mg/kg of MOH and 100 mg/kg of MOP were well tolerated if given in 4 equal doses over a 25 day period. These studies indicated that significantly more of the mitomycin prodrug was tolerated because of its reduced toxicity.

Therapy studies were then performed on nude Balb C nu/nu female mice (6 mice per treatment group) (4-6 wk old) obtained from Life Sciences (St. Petersburg, Fla.) that had been implanted (s.c., right hind flank) with a H2981 tumor obtained from in vivo sourcing. The experiments were run when the tumors reached approximately 100 mm$^3$ in volume. The L6-AP and 1F5-AP conjugates (0.1 ml containing 250 $\mu g$ antibody in PBS) were each administered (i.p.) 18-24 h prior to treatment with MOP (0.2 ml containing 0.6 mg MOP in $H_2O$). Tumor growth was compared to that observed in untreated mice and in mice treated with maximum tolerated doses of MOP (0.2 ml containing 0.6 mg MOP in $H_2O$) or MOH (0.2 ml containing 0.2 mg MOH in $H_2O$) alone.

Figure 18:
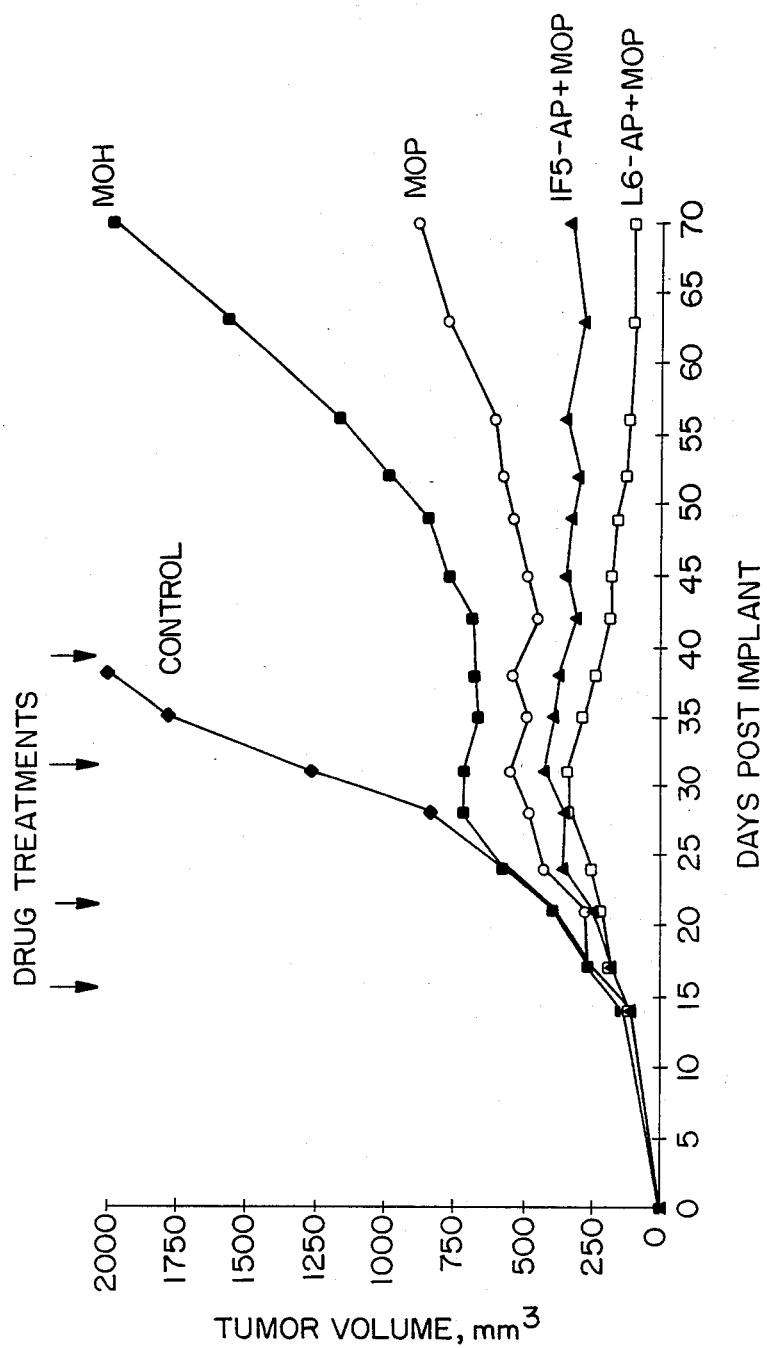
FIG. 18 is a comparative graphical presentation of tumor volume over time in mice ●: untreated (control) or treated with ■: MOH, O: MOP, ▲: 1F5-AP+MOP or □: L6-AP+MOP. Arrows indicate the spaced drug treatments and where applicable, the conjugates were administered 18–24 hours earlier than each drug treatment. The graph depicts the pronounced antitumor effect observed upon treatment of the tumor with L6-AP+MOP.

As shown in FIG. 18, both MOH and MOP had significant antitumor activities in vivo. The time required to reach an average tumor volume of 750 mm$^3$ was 45 days in mice treated with MOH, 63 days in mice treated with the MOP prodrug and 27 days in the control group. As discussed above, the MOP prodrug was less toxic to the animals and therefore the higher dosage that could be administered resulted in a greater antitumor effect than that seen with the MOH derivative. Although the non-binding conjugate, 1F5-AP, enhanced the activity of MOP somewhat, a much more pronounced effect was observed in the group that received L6-AP prior to MOP treatment. As the figure indicates, at day 70, tumors that had been pretreated with the L6-AP conjugate (followed by MOP treatment) were approximately one third the size of tumors pretreated with the 1F5-AP conjugate. Furthermore, as Table 3 below indicates, by day 63 post-implant, 3 out of 6 tumors in the L6-AP+ MOP-treated mice underwent complete regression and the remaining 3 tumors had not increased in size from the onset of treatment. In contrast, 3 out of 5 tumors in the 1F5-AP+MOP-treated group actually progressed in size, 2 out of 5 of the tumors were stable, and there were no partial or complete regressions.

TABLE 3

RESPONSE OF TUMORS (BY DAY 63) TO TREATMENT WITH ANTIBODY-AP CONJUGATES AND MITOMYCIN DERIVATIVES

| GROUP | TUMOR RESPONSES | | | |
|---|---|---|---|---|
| | PROGRESSION | STABLE | PARTIAL REGRESSION | COMPLETE REGRESSION |
| Control | 6/6 | | | |
| MOH | 6/6 | | | |
| MOP | 4/5 | 1/5 | | |
| 1F5-AP + MOP | 3/5 | 2/5 | | |
| L6-AP + MOP | | | 3/6 | 3/6 |

These experiments clearly demonstrate the specificity and enhanced antitumor effect of the targeted enzyme/MOP combination of the invention in vivo.

EXAMPLE 3

This example demonstrates the applicability of the immunoconjugates, prodrugs and methods of this invention for the delivery of a number of different drugs to tumor cells. Using the antibody-alkaline phosphatase conjugate, L6-AP, in combination with the prodrugs, EP and MOP, enhanced antitumor activity in vivo was demonstrated. Thus, the present invention provides the use of a single antibody-targeted enzyme with a panel of prodrugs for combination chemotherapy against tumors.

The prodrugs, EP and MOP, were prepared as described in Examples 1 and 2, respectively. Preparation of the L6-AP and 1F5-AP immunoconjugates is described in Example 1. The in vivo studies on nude mice were carried out as described in Examples 1 and 2 above. Thus, nude mice that had been implanted with a H2981 tumor were pre-exposed to the L6-AP or 1F5-AP conjugate 18-24 h prior to treatment with a combination of MOP/EP (0.2 ml containing 1 mg EP and 0.3 mg MOP in $H_2O$). Tumor growth was compared to that observed in untreated mice and in mice treated with the MOP/EP combination alone.

Figure 19:
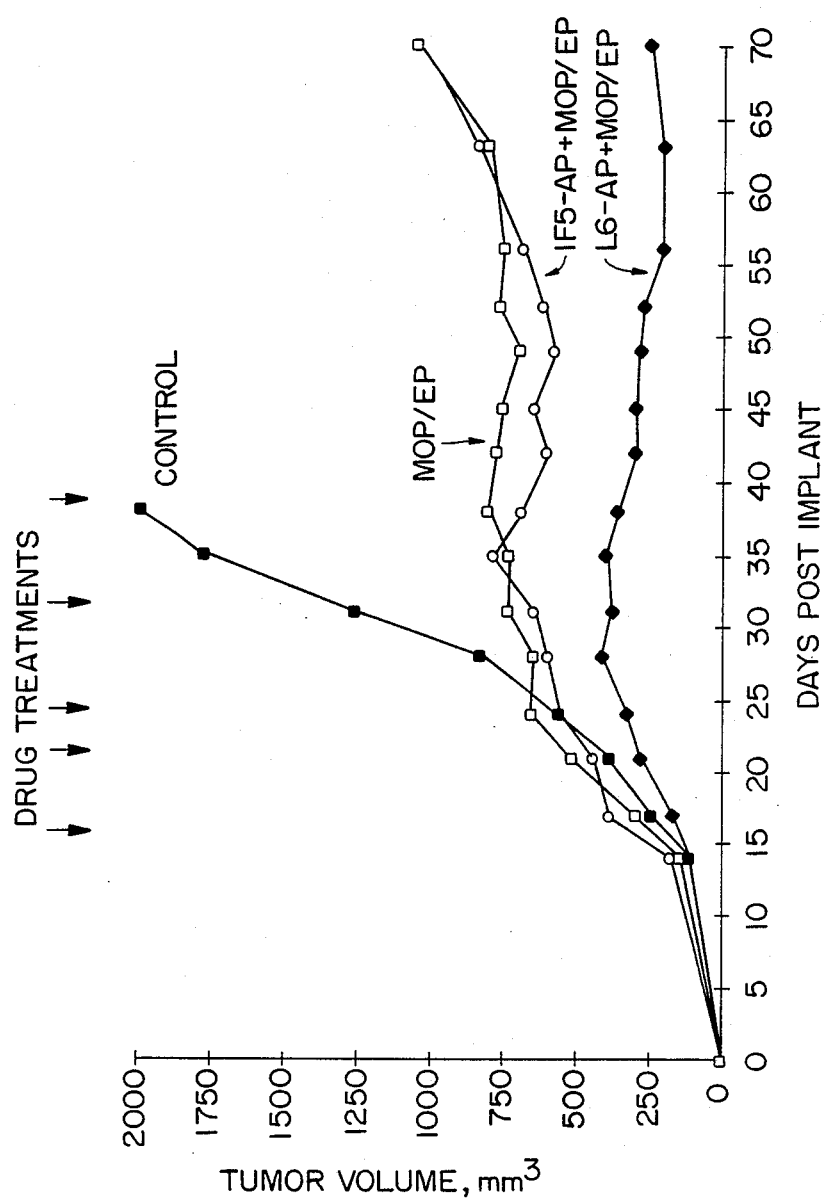
FIG. 19 is a comparative graphical presentation of tumor volume over time in mice ■: untreated (control) or treated with □: MOP/EP, O: 1F5-AP+MOP/EP or ●: L6-AP+MOP/EP. Arrows indicate the spaced drug treatments and where applicable, the conjugates were administered 18–24 hours earlier than each drug treatment. The graph demonstrates the pronounced antitumor effect observed upon treatment of the tumor with the L6-AP conjugate of this invention and a combination of the prodrugs, MOP and EP.

As shown in FIG. 19, the antitumor activities of the MOP/EP combination alone and the MOP/EP combination plus 1F5-AP treatment were approximately equal. And, as Table 4 below indicates, all of the tumors in these two groups as well as the tumors of the untreated control mice grew in size. Pre-treatment of the tumor-bearing mice with the L6-AP conjugate followed by the MOP/EP combination, however, resulted in a pronounced antitumor response. As FIG. 19 indicates, at day 70, tumors that had been pretreated with L6-AP (followed by combined MOP/EP treatment) were approximately one third the size of the tumors pretreated with the 1F-AP conjugate. Furthermore, Table 4 shows that by day 63 post-implant, one out of six tumors in the L6-AP-pretreated group of mice had completely regressed, 3 out of six tumors had stopped growing and only two out of six tumors progressed in size.

TABLE 4

RESPONSE OF TUMORS (BY DAY 63) TO TREATMENT WITH ANTIBODY-AP CONJUGATES AND MITOMYCIN/ETOPOSIDE COMBINATIONS

| GROUP | TUMOR RESPONSES | | | |
|---|---|---|---|---|
| | PRO-GRESSION | STABLE | PARTIAL REGRESSION | COMPLETE REGRESSION |
| Control | 6/6 | | | |
| MOP/EP | 5/5 | | | |
| 1F5-AP + MOP/EP | 6/6 | | | |
| L6-AP + MOP/EP | 2/6 | | 3/6 | 1/6 |

Thus, these in vivo studies indicate the applicability of the conjugates, prodrugs and methods of this invention for combination therapy against tumors.

Alternatively, the conjugates of this invention such as L6-AP can be used with other combinations of prodrugs, such as EP, adriamycin-14-phosphate and 5-fluorouridine monophosphate to deliver a number of different cytotoxic agents to tumor cells.

Again, preparation of the antibody-enzyme conjugate, L6-AP, and the prodrug, etoposide-4'-phosphate, is as described in Example 1. Adriamycin-14-phosphate is prepared as described in U.S. Pat. No. 4,185,111, issued to J. B. Ducep on Jan. 22, 1980. 5-Fluorouridine monophosphate is prepared as described in M. J. Robins et al., *Can. J. Chem.*, 53, pp. 1302-1306 (1975).

The reaction of L6-AP with the three above-mentioned prodrugs is carried out as follows: either AP alone or the L6-AP conjugate (final AP concentration 5 μg/ml) is added to solutions of etoposide-4'-phosphate or adriamycin-14-phosphate (0.1 mM) in Tris buffer (100 mM) containing MgCl$_2$ (1 mM) and ZnCl$_2$ (0.1 mM) at pH 7.0. For the 5-fluorouridine prodrug, reaction conditions require a solution of 5-fluorouridine (3 μM) in phosphate buffer (100 mM) at pH 8.0. The reaction of L6-AP with either the etoposide phosphate or 5-fluorouridine prodrug is monitored as described in Example 1. The reaction of L6-AP with adriamycin-14-phosphate is monitored by HPLC using an IBM C-18 column (3 μ, 4.5×100 mm) and 65% methanol in water containing 3% ammonium acetate as eluant (0.5 ml/min, monitored at 495 nm).

The reaction of the antibody-AP conjugate with each prodrug results in the removal by hydrolysis of the phosphate moieties to release the free drugs [see, e.g., R. B. McComb et al., *Alkaline Phosphatase*, Plenum Press (New York 1979)].

The cytotoxicity for tumor cells of each of the three prodrugs in the presence of the L6-AP conjugate of this invention can be demonstrated using the colony inhibition assay as described in Example 1 above. Upon removal of the phosphate moiety from each of the prodrugs by the conjugate, etoposide, adriamycin and 5-fluorouridine are released. Each of these drugs has been shown to be potent antitumor agents [see, e.g., P. J. O'Dwyer et al., "Etoposide: Current Status Of An Active Anticancer Drug", *New England Journal Of Medicine*, 312, pp. 692-700 (1985); M. J. Embleton et al., "Antibody Targeting Of Anti-Cancer Agents", in *Monoclonal Antibodies For Cancer Detection And Therapy*, R. W. Baldwin and V. S. Byers (ed.s), pp. 321-22 (Academic Press 1985); U.S. Pat. No. 4,185,111, supra; S. T. Crooke and S. D. Reich (ed.s), *Anthracyclines: Current Status And New Developments*, Academic Press (New York 1980); and C. Heidelberger et al., "Fluorinated Pyrimidines And Their Nucleosides" in *Adv. Enzymol. Relat. Areas Mol. Biol.*, 54, pp. 57-119 (1983)].

The prodrugs of etoposide, adriamycin and 5-fluorouridine can therefore by used together or sequentially for the release of the corresponding known antitumor agents at the site of the tumor by the antibody-alkaline phosphatase conjugates of this invention. It has been demonstrated, for example, that antitumor agents administered in combination with each other can act synergistically [see, e.g., S. Monfardini et al., *Manual of Cancer Chemotherapy*, UICC Technical Report Series, 56 (b 1981)]. This embodiment of the invention therefore provides a method for combined chemotherapy against tumors.

EXAMPLE 4

The following example demonstrates the use of still other immunoconjugates and prodrugs of the invention for the conversion of a relatively non-cytotoxic prodrug into an active antitumor agent displaying in vitro cytotoxicity toward tumor cells. According to this example, an L6-penicillin V amidase (referred to hereinafter as "PVA") immunoconjugate is used to convert a N-phenoxyacetyl derivative of adriamycin into the known antitumor agent, adriamycin.

Preparation Of Antibody-Penicillin V Amidase Conjugates Of The Invention

In this example, an L6-PVA immunoconjugate and an 1F5-PVA conjugate were prepared. The antibodies L6 and 1F5 and their sources have been described earlier. The amidase enzyme utilized was a penicillin V amidase isolated from a fungal culture of *Fusarium oxysporum* according to the methods disclosed by D. A. Lowe et al., "Enzymatic Hydrolysis Of Penicillin V to 6-Aminopenicillanic Acid By *Fusarium Oxysporum*", *Biotechnology Letters*, 8 (3), pp. 151-56 (1986). *Fusarium oxysporum* strains from which this enzyme can be isolated are deposited with the ATCC. Thus, PVA is a readily-available enzyme that converts penicillin-V to penicillanic acid. More specifically, PVA hydrolyzes the phenoxyacetyl amide bond of penicillin-V to yield penicillanic acid. The enzyme, which reacts with phenoxyacetamides, may therefore be used to cleave prodrugs of known cytotoxic agents that have been derivatized with phenoxyacetic acid or p-hydroxyphenoxyacetic acid.

The antibody-PVA conjugates of this embodiment of the invention were prepared in essentially the same manner as described for the AP conjugates of Example 1. The antibodies, L6 and 1F-5, were reacted with iminothiolane as described and the number of sulfhydryl groups introduced onto each of the antibodies was determined to be between 1-2.

The PVA enzyme was then dissolved at 9 mg/ml in PBS and treated with SMCC (Pierce Chemical Co., 100 mM in DMF) so that the final concentration was 5 mM. Treatment with SMCC introduced maleimido groups onto the enzyme. After 30 min at 30° C., the modified enzyme was purified by gel filtration on G-25 PD-10 Sephadex (Pharmacia, Upsalla, Sweden) and eluted with PBS. The modified PVA was then added to a solution of each thiolated antibody in a 3:1 molar ratio. Each reaction mixture was saturated with nitrogen and left at room temperature for 3 h and then incubated at 4° C. for an additional 18 h. At that point, 2-aminoethanethiol (1 mM final concentration) was added to each solution to block any additional unreacted maleimides.

Each reaction mixture was then passed through a gel filtration column (G-25), using 20 mM Tris, pH 7.2, with 50 mM NaCl as the eluant. The resulting mixtures were purified on DEAE Sephadex columns (2.5×10 cm). Fractions were monitored at 280 nm. The unreacted antibody of each mixture did not bind to the column and the conjugate and unreacted PVA were eluted with 20 mM Tris, pH 7.2, with 0.5 M NaCl. The fractions containing PVA and conjugate were then concentrated using an Amicon YM-30 ultrafiltration filter and purified on a Sephacryl S-300 column (2.5×95 cm) using PBS as eluant. Fractions were monitored at 280 nm and those that contained pure conjugate, as determined by SDS-PAGE (4–12% gradient gel), were pooled.

Preparation Of A Novel Adriamycin Prodrug

Figure 20:
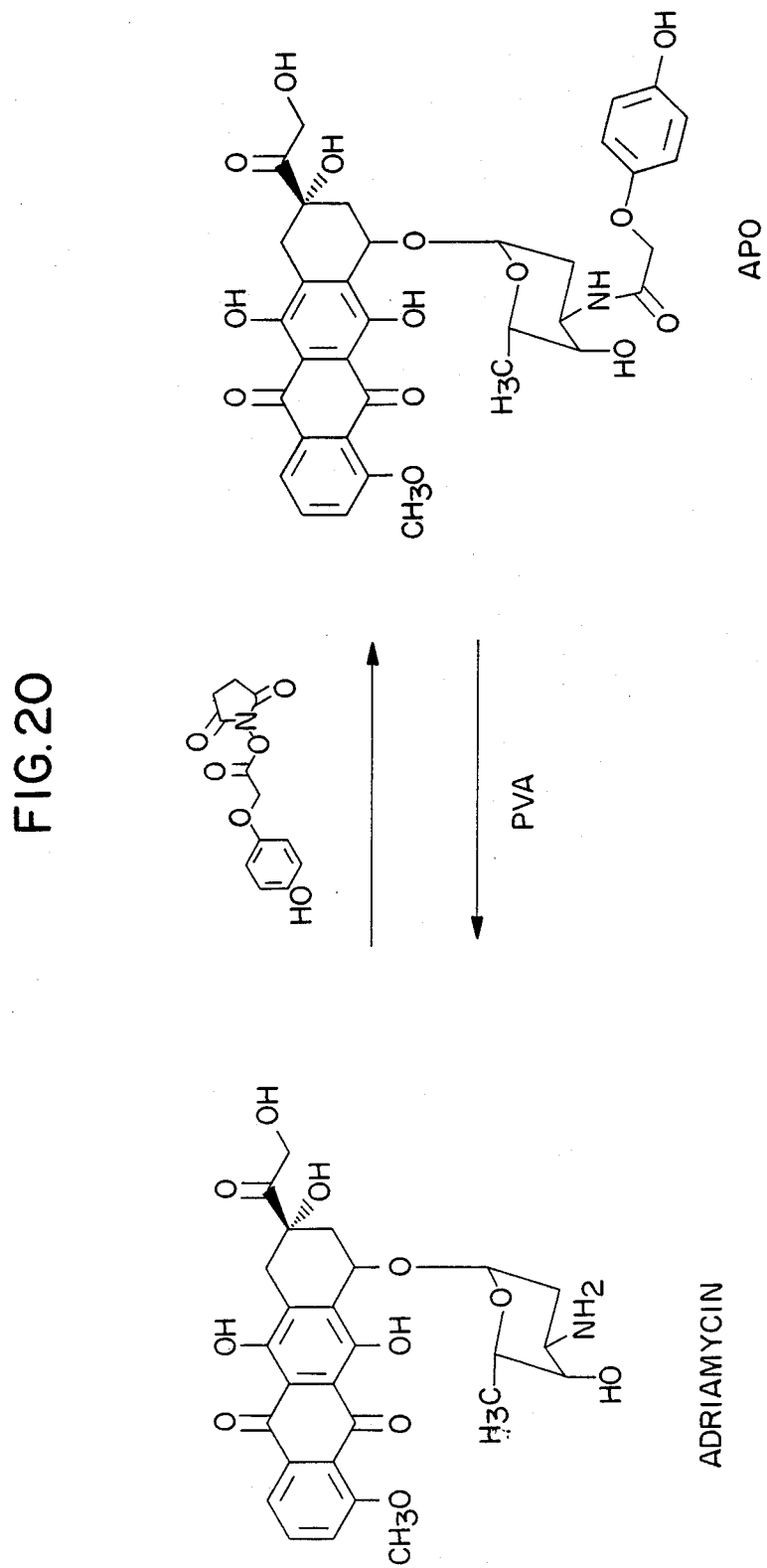
FIG. 20 depicts the chemical structure of an adriamycin prodrug of the invention ("APO") and its preparation from adriamycin.

Each of the antibody-PVA conjugates prepared above was then reacted with a novel adriamycin prodrug. More particularly, the prodrug utilized was N-(p-hydroxyphenoxy acetyl)adriamycin (referred to hereinafter as "APO"), wherein adriamycin is acylated at the amino-sugar position with p-hydroxy-phenoxyacetic acid as depicted in FIG. 20.

This adriamycin prodrug was synthesized as follows:

Into 10 ml of tetrahydrofuran were placed 84 mg (0.5 mmole) of p-hydroxy-phenoxyacetic acid, 57 mg (0.5 mmole) of N-hydroxysuccinimide, and 100 mg (0.49 mmole) of dicyclohexylcarbodiimide. This mixture was stirred for 2 h at which time the solution was filtered and the filtrate added to 200 mg (0.35 mmole) of adriamycin hydrochloride. 0.1 ml of triethylamine was added to the reaction mixture and stirring was continued for 4 h. The reaction mixture was then filtered through glass wool and evaporated to a residue under high vacuum. The resulting mixture was purified on a silica gel 60 column (2.5×20 cm) eluted with 95:5 dichloromethane:methanol. The pooled fractions were purified again on the same kind of column to yield 70 mg (0.1 mmole, 30% yield) of pure N-(p-hydroxyphenoxyacetyl) adriamycin.

FAB MS m/e 694.2125 (M+H)+. Calculated $C_{35}H_{36}NO_{14}$, 694.2136. 360 MHz $^1$H NMR (CDCl$_3$) $\delta$1.06 (d, 3H, sugar CH$_3$), 1.5–2.2 (m, 6H, sugar H), 3.0 (q, 2H) 4.0 (s, 3H, OCH$_3$), 4.35 (s, 2H, COCH$_2$O), 4.8–5.0 (m, 3H), 5.2 and 5.4 (s, 1H), 6.6–6.8 (dd, 4H, phenoxy ArH), 7.4–7.9 (m, 3H, 2,3,4-H), 9.0 (s, 1H, Ar'OH), 11.61 and 12.39 (s, 1H, ArOH).

It should be understood that other phenoxyacetyl amide derivatives of adriamycin can be synthesized using substantially the same procedure as described above. For example, N-(phenoxyacetyl)adriamycin can be synthesized as described in this section wherein the p-hydroxyphenoxyacetic acid is replaced by 0.5 mmole (76 mg) of phenoxyacetic acid. Similarly, N-(p-hydroxyphenoxyacetyl)melphalan or daunomycin prodrugs or N-(phenoxyacetyl)melphalan or daunomycin prodrugs can be synthesized by this synthetic protocol, wherein 100 mg of mephalan or 200 mg of daunomycin (0.35 mmole) are used.

Figure 21:
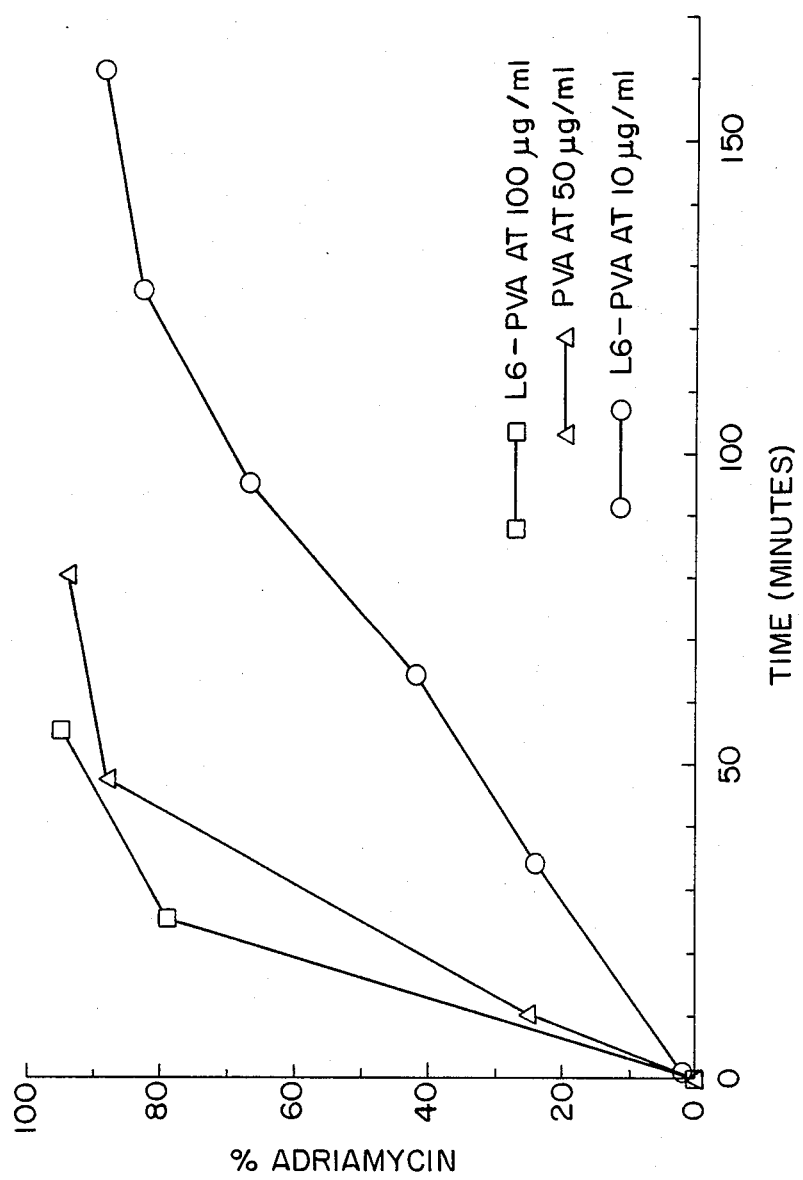
FIG. 21 is a comparative graphical presentation of the percentage of adriamycin released over time upon reaction of APO with Δ: free penicillin V amidase enzyme or O and □: the L6-PVA conjugate of the invention at 10 and 100 μg total protein/ml, respectively. The course of the reaction was monitored by HPLC.

Reaction Of An Antibody-Penicillin V Amidase Conjugate With An Adriamycin Prodrug The ability of the antibody-PVA conjugate, L6-PVA, to convert the novel prodrug, APO, to adriamycin was measured as follows: either (a) PVA alone (final concentration:50 μg/ml), (b) 100 μg/ml of the L6-PVA conjugate (final PVA concentration: 25 μg/ml) or (c) 10 μg/ml of L6-PVA (final PVA concentration: 2.5 μg/ml) were added to a solution of APO (0.1 mM) in PBS. Each reaction was monitored by HPLC using a Phenominex C-18 column (3 μm, 4.5×100 mm) and a gradient elution of 20–60% tetrahydrofuran in water with 0.1% $H_3PO_4$ (1.0 ml/min, monitored at 495 nm). Under these conditions, the adriamycin eluted at 8.9 minutes and the APO eluted at 12.2 minutes. The results are shown in FIG. 21.

As the figure demonstrates, the amide group of APO was in fact hydrolyzed by PVA as indicated by the generation of adriamycin. Under the conditions used, the half life for the hydrolysis of APO by PVA was approximately 20 min. Furthermore, it was found that within 40 minutes of the start of the reaction, either the enzyme alone or the antibody-PVA conjugate was able to effect the hydrolysis of at least 80% of APO to adriamycin. The conjugate at 10 μg/ml (2.5 μg/ml of PVA) was able to effect this level of hydrolysis in 120 minutes. Finally, it is evident from these studies that the antibody-PVA conjugate of this invention did not exhibit any apparent loss in enzymatic activity due to the attachment of the enzyme to the antibody as evidenced by the fact that the conjugate and free enzyme displayed similar abilities in hydrolyzing APO to adriamycin.

Serum Stability Of The Novel Adriamycin Prodrug Of The Invention

The stability of APO in human serum was determined using HPLC and measuring the rate of disappearance of APO and the rate of formation of adriamycin. Thus, a solution of APO (10 mM in dimethylformamide) was added to fresh human serum such that the final concentration was 0.1 mM. Aliquots (50 μl) were diluted with methanol (50 μl) to precipitate serum proteins. These samples were then centrifuged and analyzed by HPLC as described immediately above. No hydrolysis of APO to adriamycin occurred in two hours.

Binding Of The Antibody-PVA Conjugates To H2981 Tumor Cells

Figure 22:
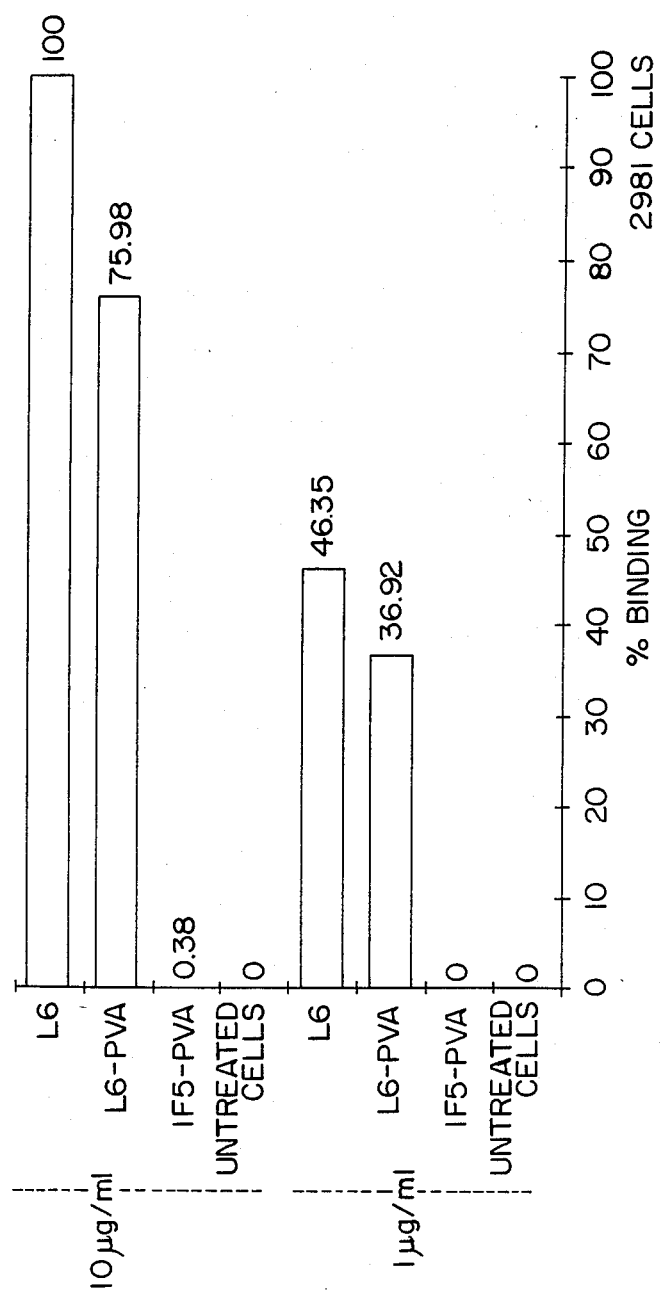
FIG. 22 depicts the comparative binding to H2981 tumor cells of the L6 monoclonal antibody and the L6-PVA and 1F5-PVA conjugates of the invention.

The ability of the L6-PVA and 1F5-PVA conjugates of the invention to bind to H2981 tumor cells was measured as described in Examples 1 and 2. The results of the binding assay are depicted in FIG. 22.

FACS analysis indicated that both L6 and the L6-PVA conjugate bound strongly to the tumor cells while the 1F5-PVA conjugate did not display any significant amount of binding. This binding study indicates firstly that conjugation to the enzyme did not substantially affect the binding ability of the antibody component of the immunoconjugates of this invention. Secondly, this assay again demonstrates the specificity of binding of the conjugates; the L6-PVA conjugate binding to the L6-positive H2981 tumor cells and the 1F5-PVA conjugate, due to the 1F5 antibody's lack of specificity for the tumor cells, showing essentially no binding.

In Vitro Cytotoxicity Of The Antibody-PVA Conjugate/Adriamycin Prodrug Combination Of The Invention On H2981 Tumor Cells The in vitro cytotoxic effect of the antibody-PVA/adriamycin prodrug combination of the invention toward H2981 tumor cells was measured using the $^3$H-thymidine uptake assay described in Examples 1 and 2 above. Briefly, the H2981 tumor cells were plated into 96-well microtiter plates in IMDM (10,000 cells/well) and were allowed to attached for 18 h at 37° C. The antibody-PVA conjugates, L6-PVA or 1F5-PVA, were then added at a concentration of 10 μg/ml of antibody and the plates were incubated for 30 min at 4° C. The wells were then washed four times with IMDM and APO was added at varying concentrations in IMDM. After two h, the wells were again washed, IMDM was added and the cells were left for 18 h at 37° C. At that point, $^3$H-thymidine was added (1 μCi per well) and after 6 h, the plates were frozen at −70° C. to detach the cells. After thawing, the cells were harvested onto glass fiber filters. The incorporation of $^3$H-thymidine was measured in a Beckman 3801 scintillation counter and compared to cells treated with APO or adriamycin (ADM) alone.

Figure 23:
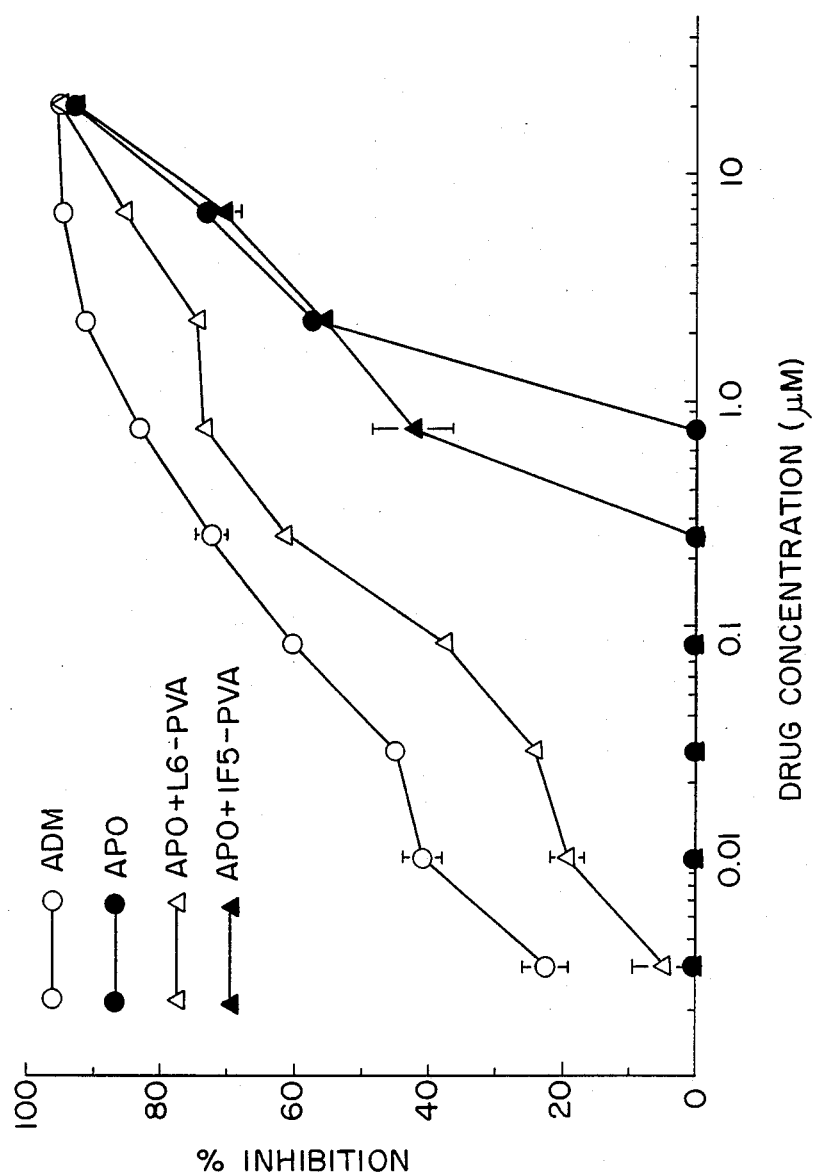
FIG. 23 is a comparative graphical presentation of the percent inhibition of $^3$H-thymidine incorporation into the DNA of H2981 tumor cells treated with O: adriamycin (ADM), ●: APO, △: L6-PVA+APO or ▲: 1F5-PVA+APO. The graph depicts the increase in cytotoxic activity observed when the tumor cells were pretreated with the L6-PVA conjugate followed by APO treatment as compared to the activity seen upon treatment with APO alone.

Using this assay, we measured the inhibition of $^3$H-thymidine incorporation into the DNA of the tumor cells and thus, the cytotoxic effect of the prodrug, APO, on the cells with or without pretreatment of the cells with the L6-PVA or 1F5-PVA conjugates. The cytotoxic effects of these combinations were compared to the cytotoxicity observed upon treatment of the cells with the parent drug, adriamycin, alone. As shown in FIG. 23, on tumor cells untreated with any conjugate, adriamycin, with an IC$_{50}$ of 38 nM, was significantly more toxic than APO with an IC$_{50}$ of 2 μM. This was expected based upon previous reports showing that adriamycin amides are less toxic than adriamycin [see, e.g., Y. Levin and B. A. Sela, *FEBS Letters*, 98, p. 119 (1979) and R. Baurain et al., *J. Med. Chem.*, 23, p. 1171 (1980)]. Pretreatment of the cells with L6-PVA enhanced the cytotoxicity of APO 20-fold to a level comparable to that seen with adriamycin alone. Pretreatment of the cells with 1F5-PVA did not affect the toxicity of APO at all. These results indicate that the L6-PVA conjugate is capable of hydrolyzing the relatively non-cytotoxic prodrug, APO, to kill the tumor cells to an extent comparable to the use of adriamycin alone and that this cytotoxicity is antigen specific as indicated by the fact that the 1F5-PVA conjugate, which does not bind significantly to this particular tumor cell line, showed no such cytotoxicity.

Binding Of The Antibody-PVA Conjugates To Daudi Lymphoma Cells

Figure 24:
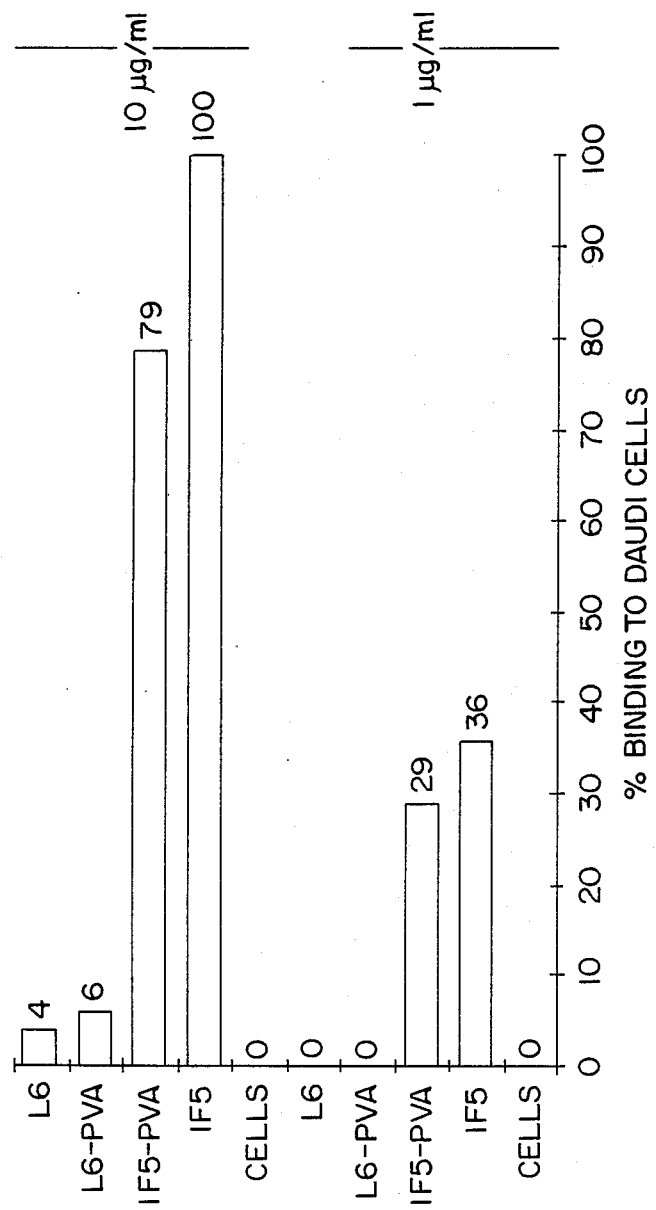
FIG. 24 depicts the comparative binding to Daudi lymphoma cells of the L6 and 1F5 monoclonal antibodies and the L6-PVA and 1F5-PVA conjugates of the invention.

The ability of the L6-PVA and 1F5-PVA conjugates of the invention to bind to the known Daudi cell line was also measured. This cell line is a Burkitt lymphoma cell line, deposited with the ATCC (ATCC # CCL 213), that expresses the CD-20 antigen to which the 1F5 antibody binds. The binding assay was carried out as described in Example 1, except that the cells used were Daudi cells, and the results are depicted in FIG. 24.

In this instance, the 1F5 monoclonal antibody and the 1F5-PVA conjugate both bound strongly to the lymphoma cells. Thus, this study again indicates that the binding ability of the conjugates was not significantly affected by the conjugation procedure.

Furthermore, as the figure indicates, the L6 antibody and the L6-PVA conjugate showed no appreciable binding to the Daudi cells. This was to be expected because Daudi tumor cells do not possess the antigen with which the L6 antibody reacts. Thus, this study taken in combination with the previous binding studies described herein, clearly demonstrates the specificity of binding of the conjugates of this invention, i.e., the L6-containing conjugates bind specifically to L6-positive tumor cells and the 1F5-containing conjugates bind specifically to CD-20-positive tumor cells.

In Vitro Cytotoxicity Of The Antibody-PVA Conjugate/Adriamycin Prodrug Combination Of The Invention On Daudi Cells We then tested the in vitro cytotoxic effect on Daudi cells of the L6-PVA or 1F5-PVA conjugate in combination with the APO prodrug.

The $^3$H-thymidine assay was performed essentially as described in the examples above with slight modifications due to the fact that the Daudi cells are non-adherent. Thus, approximately 250,000 Daudi cells in IMDM were plated into each well of a 96-well microtiter plate and the antibody-enzyme conjugate added. The reaction mixture was incubated at 4° C. for 30 min. Unbound antibody-enzyme conjugate was removed by centrifuging at 500×g for 5 min and removing the supernatant. The cells were resuspended in IMDM and the washing procedure was repeated three times to remove all unbound conjugate. APO in IMDM was then added for 2 h and washed once as described above. The remainder of the assay was performed as described in the examples above.

Figure 25:
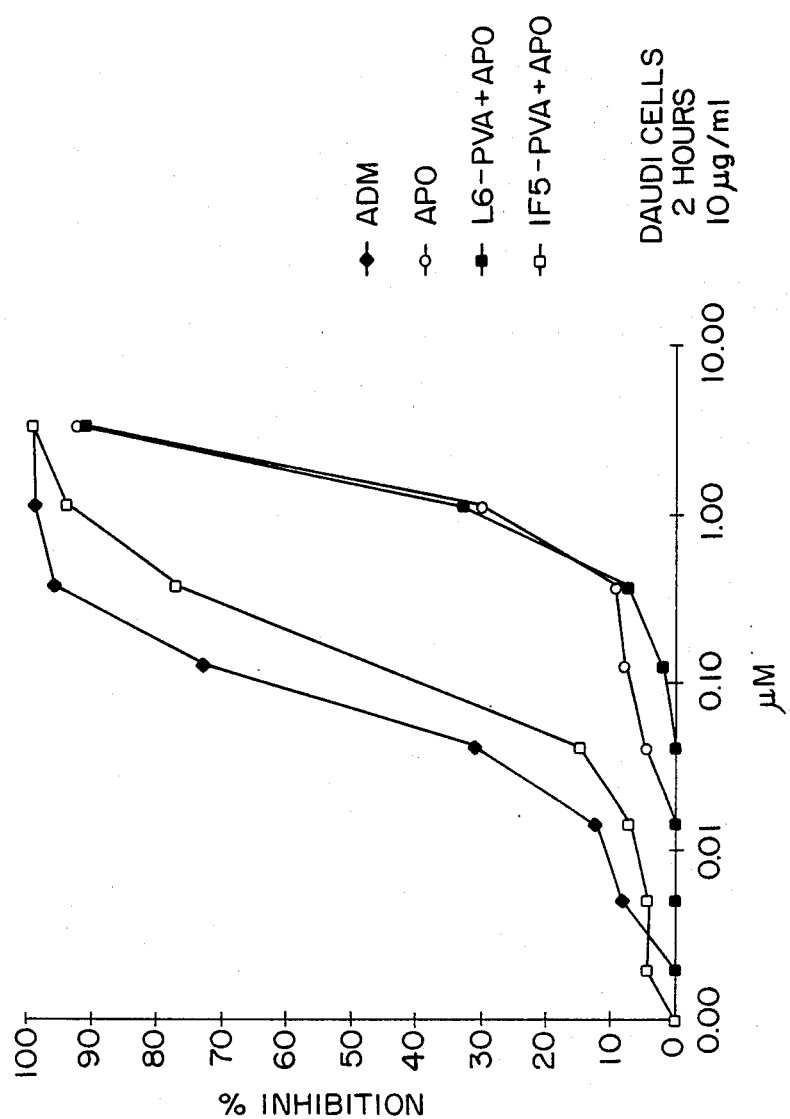
FIG. 25 is a comparative graphical presentation of the percent inhibition of $^3$H-thymidine incorporation into the DNA of Daudi lymphoma cells treated with ●: ADM, O: APO, ■: L6-PVA+APO or □: 1F5-PVA+APO. The graph depicts the increase in cytotoxic activity observed when the tumor cells were pretreated with the 1F5-PVA conjugate followed by APO treatment as compared to the cytotoxic effect seen upon treatment of the cells with APO alone.

Using this assay, we measured the inhibition of $^3$H-thymidine incorporation into the DNA of the Daudi cells and thus, the cytotoxic effect of the APO prodrug on the cells with or without pretreatment of the cells with the L6-PVA or 1F5-PVA conjugate. The cytotoxic effects of these combinations were compared to the cytotoxicity observed upon treatment of the cells with adriamycin alone. As shown in FIG. 25, on Daudi cells untreated with any conjugate, adriamycin was significantly more toxic than APO. Pretreatment of the cells with the 1F5-PVA conjugate significantly enhanced the cytotoxicity of the APO prodrug to a level comparable to that seen with adriamycin alone, whereas pretreatment with the L6-PVA conjugate resulted in no such enhancement.

It should be noted that the results obtained from these binding and cytotoxicity studies are the opposite of the results obtained with these conjugates in the studies described earlier in this example using H2981 tumor cells where the L6-PVA plus APO combination showed enhanced cytotoxic effects and the 1F5-PVA plus APO combination did not. This was to be expected given the different specificities of the L6 and 1F5 antibodies of the conjugates and clearly demonstrates the specificity of the cytotoxic effects obtained with the conjugate/prodrug combinations of the invention.

Furthermore, this study indicates the usefulness of the 1F5-PVA conjugate in combination with APO for the production of cytotoxic effects on tumor cells in vitro. Thus, the in vitro cytotoxicity studies of this example demonstrate the applicability of the present invention to any conjugate containing an antibody reactive with a tumor-associated antigen for the treatment of tumors with which that antibody reacts.

EXAMPLE 5

Figure 26:
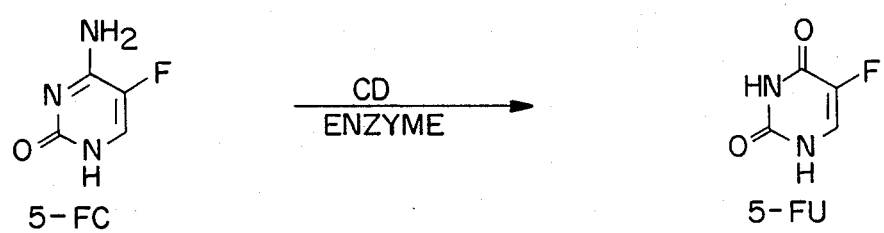
FIG. 26 depicts the chemical structures of 5-fluorocytosine ("5-FC") and 5-fluorouracil ("5-FU"). 5-FC is a prodrug that is converted to 5-FU according to the methods of this invention.

This example relates to the use of the immunoconjugates and methods of this invention to convert the prodrug, 5-fluorocytosine, (referred to hereinafter as "5-FC"), into the antitumor drug, 5-fluorouracil (referred to hereinafter as "5-FU"), by an antibody-bound cytosine deaminase (CD) enzyme (see FIG. 26). The antibody-CD conjugate/5-FC prodrug combination of this embodiment demonstrated a significant cytotoxic effect toward tumor cells in vitro.

Preparation Of Antibody-Cytosine Deaminase Conjugates Of The Invention

L6-CD and 1F5-CD immunoconjugates were prepared using the L6 and 1F5 monoclonal antibodies referenced in earlier examples and a cytosine deaminase enzyme. Although CD enzymes have been detected and isolated from a variety of microorganisms [see, e.g., West et al., *Biochem. Biophys. Acta.*, 719, pp. 251–58 (1982)], the particular CD utilized in this example was purified from compressed bakers' yeast in a manner similar to that reported by P. L. Ipata et al., "Baker's Yeast Cytosine Deaminase. Some Enzymatic Properties And Allosteric Inhibition By Nucleosides And Nucleotides," *Biochemistry*, 10, pp. 4270–76 (1971).

Briefly, yeast cells (*Saccharomyces cerevisiae*) (2.0 kg) were plasmolyzed with ethyl acetate and ammonium sulfate precipitation (50–73%) was performed twice to obtain a crude enzyme preparation. The ammonium sulfate pellet was dialyzed against 10 mM Tris-Cl buffer, pH 8.0, applied to a Q-Sepharose anion exchange column (Pharmacia), and eluted with a KCl gradient (0–0.3 M).

Fractions were analyzed for CD activity using 3 mM cytosine (or 5-FC) as substrate in PBS at 27° C. according to the procedure of T. Nishiyama et al., "Antineoplastic Effects In Rats Of 5-Fluorocytosine In Combination With Cytosine Deaminase Capsules," *Cancer Research*, 45, pp. 1753–61 (1985)]. Thus, according to this procedure, a small amount of the enzyme preparation was added to the substrate, cytosine (or 5-FC), and the course of the reaction was monitored via UV spectrophotometry for the generation of uracil (or 5-FU) on aliquots that were quenched with 0.1 N HCl. Ratios of 250/280 (for cytosine) and 255/290 (for 5-FC) were used to measure the amount of uracil or 5-FU formed. This procedure for determining CD activity was utilized at each stage of the purification of the CD enzyme as well as during the purification of the CD-containing conjugates of this invention described below.

Thus, the active fractions from the KCl gradient were pooled, concentrated and purified on a G-75 Sephadex column. At this stage, SDS-PAGE (14%, non-reducing) indicated that the fraction containing CD activity was comprised of a major protein of MW 18 kd and minor amounts of proteins at 20 and 30 kd. The CD activity of this fraction was 10 U/mg protein (using cytosine as substrate). Other preparations yielded material with activity as high as 17 U/mg protein. All protein assays were conducted using the BCA protein assay reagent available from Pierce (Rockford, Ill.).

The purified CD was then conjugated to the L6 or 1F5 monoclonal antibodies in essentially the same manner as described for the AP conjugates of Example 1. The crude conjugates (untreated with iodoacetamide) were purified by gel filtration on S-200 Sepharose using PBS as eluant. Fractions were monitored at 280 nm and the CD activity of each fraction was assayed as described immediately above. Fractions containing conjugates with appropriate levels of CD-antibody ratios were pooled and analyzed by SDS-PAGE on a 4–12%, non-reducing gradient gel to yield purified L6-CD and 1F5-CD conjugate preparations.

Figure 27:
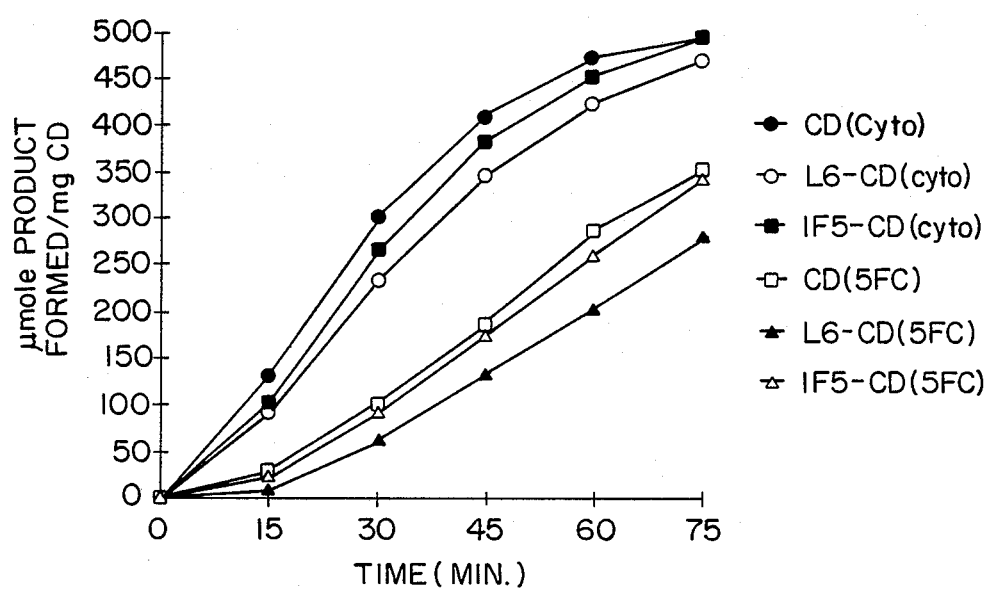
FIG. 27 is a comparative graphical presentation of the amount of product formed over time upon reaction of cytosine (cyto) with ●: CD, O: L6-CD or ■: 1F5-CD or upon reaction of 5FC with □: CD, ▲: L6-CD or △: 1F5-CD. The product formed using cytosine as substrate was uracil and the product formed using 5-FC as substrate was 5-FU. The course of the reaction was monitored spectrophotometrically.

Reaction Of The Antibody-Cytosine Deaminase Conjugates With The Prodrug, 5-Fluorocytosine The ability of the L6-CD and 1F5-CD conjugates of the invention to convert the prodrug, 5-FC, to 5-FU or the substrate cytosine to uracil was measured as follows: either free CD (final concentration: 5 $\mu$g/ml), the L6-CD conjugate (final CD concentration: 5 $\mu$g/ml) or the 1F5-CD conjugate (final CD concentration: 5 $\mu$g/ml) was added to a solution of 3 mM of a) cytosine or b) 5-FC in PBS at 27° C. and the amount of product formed over time was measured spectrophotometrically as described in the example section above. The results are shown in FIG. 27.

As the figure indicates, 5-FU was generated from the prodrug, 5-FC, by both the free CD enzyme and the antibody-CD conjugates of the invention. The figure also shows that there was no significant loss in CD enzyme activity due to attachment of the enzyme to the antibody of either conjugate as evidenced by the fact that the conjugates displayed activities equal to that of CD alone. The specific activity of the free enzyme and conjugates was approximately 4 U/mg enzyme.

For comparison, the reactivity of the conjugates were tested using cytosine, instead of 5-FC, as substrate. As the figure indicates, with cytosine as the substrate, the conjugates also displayed CD activities essentially equal to that of the free CD enzyme alone. The specific activity of the conjugates—10 U/mg bound enzyme—further indicated that the original enzyme activity of CD was preserved in the conjugate. This level of activity was maintained for several weeks when the conjugates were stored in PBS at 4° C.

Binding Of The Antibody-CD Conjugates To H2981 Tumor Cells

Figure 28:
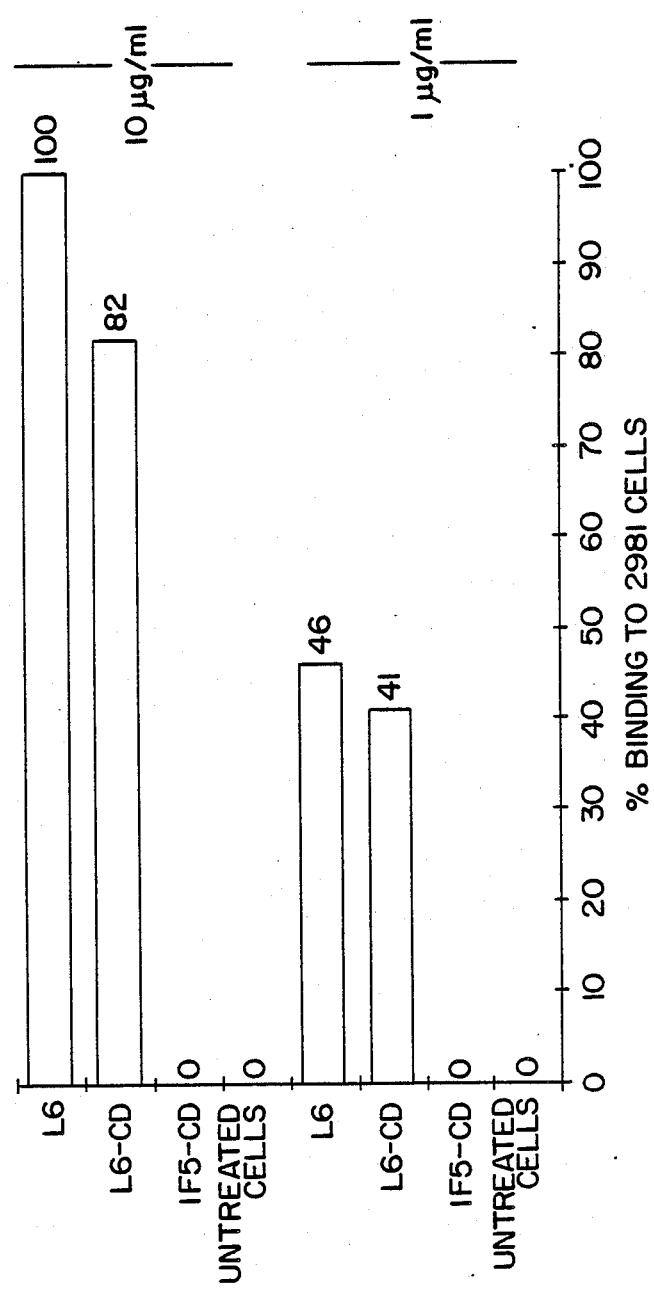
FIG. 28 depicts the comparative binding to H2981 tumor cells of the L6 monoclonal antibody and the L6-CD and 1F5-CD conjugates of the invention.

The ability of the L6-CD and 1F5-CD conjugates of the invention to bind to H2981 tumor cells was measured as described in Examples 1 and 2. The results of the binding assay are depicted in FIG. 28.

FACS analysis indicated that both L6 and L6-CD bound strongly to the tumor cells while the 1F5-CD conjugate displayed no binding to the cells. As with the previous binding studies described hereinbefore, this assay indicates the preservation of the binding activity of these conjugates despite conjugation of the antibody to the enzyme, as well as the specificity of binding of the conjugates.

In Vitro Cytotoxicity Of The Antibody-CD Conjugate/5-FC Prodrug Combination Of The Invention On H2981 Tumor Cells The in vitro cytotoxicity of the antibody-CD/5-FC prodrug combination of the invention toward H2981 tumor cells was measured using a $^3$H-leucine uptake assay similar to the $^3$H-thymidine uptake assay described in Examples 1 and 2.

According to this assay, a suspension of $10^4$ H2981 cells in 0.1 ml of IMDM with 10% (vol/vol) fetal calf serum was plated in 96-well mitrotiter plates and allowed to adhere overnight at 37° C. The plates were then washed and the L6-CD or 1F5-CD conjugate (10

μg total protein/ml containing 10 U/mg bound enzyme CD activity, using cytosine as substrate) in 0.1 ml IMDM was added. After 30 min at 4° C., the plates were washed four times and 0.15 ml of leucine-free RPMI media containing varying concentrations of the drugs, 5-FC or 5-FU, was added to the wells. The cells were incubated for 18 h at 37° C. and then pulsed for 6 h with $^3$H-leucine (1 μCi/well) in 0.05 ml of leucine-free RPMI. The plates were then processed as described in Examples 1 and 2 for the $^3$H-thymidine uptake assay.

Figure 29:
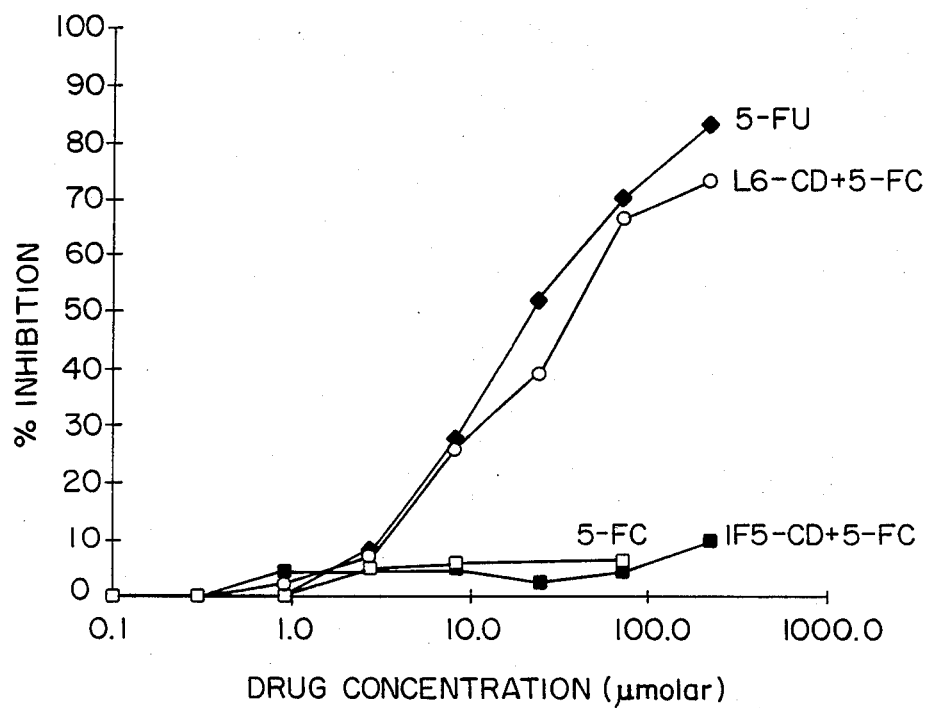
FIG. 29 is a comparative graphical presentation of the percent inhibition of $^3$H-leucine incorporation into the protein of H2981 tumor cells treated with ●: 5-FU, □: 5-FC, O: L6-CD+5-FC or ■: 1F5-CD+5-FC. The graph depicts the increase in cytotoxic activity observed when the tumor cells were pretreated with the L6-CD conjugate followed by 5-FC treatment as compared to the activity seen upon treatment with 5-FC alone.

Using this assay, we measured the inhibition of $^3$H-leucine into the protein of the tumor cells and thus, the cytotoxic effect of the prodrug, 5-FC, on the cells with or without pretreatment of the cells with the L6-CD or 1F5-CD conjugates. The cytotoxic effects of these combinations were compared to the cytotoxicity observed upon treatment of the cells with the parent drug, 5-FU, alone. As shown in FIG. 29, on tumor cells untreated with any conjugate, 5-FC exhibited very little cytotoxic activity whereas 5-FU inhibited cell growth with an IC$_{50}$ of 20 μM. However, pretreatment of the cells with the L6-CD conjugate enhanced the cytotoxicity of 5-FC to a level equal to that seen with 5-FU alone. This result is consistent with the fact that antigen-bound L6-CD is capable of converting the non-toxic prodrug, 5-FC, into 5-FU. The non-binding conjugate, 1F5-CD, showed no such enhancement, indicating the antigen-specific nature of this enhanced cytotoxicity.

While we have hereinbefore presented a number of embodiments of this invention, it is apparent that our basic construction can be altered to provide other embodiments which utilize the methods, immunoconjugates and prodrugs of this invention. Therefore, it will be appreciated that the scope of this invention is to be defined by the claims appended hereto rather than by the specific embodiments which have been presented hereinbefore by way of example.

We claim:

1. A method for the delivery of cytotoxic agents to tumor cells comprising: the administration of an effective amount of at least one antibody-enzyme conjugate comprising an antibody reactive with an antigen on the surface of said tumor cells conjugated to an enzyme which converts at least one prodrug, that is weakly cytotoxic to tumor cells compared to its corresponding parent drug, into the more cytotoxic parent drug, and the administration of an effective amount of said prodrug.

2. The method of claim 1, wherein the antibody is selected from the group consisting of polyclonal, monoclonal or chimeric antibodies.

3. The method of claim 1, wherein the antibody is selected from the group consisting of monoclonal antibodies L6, 96.5 and 1F5.

4. The method of claim 1, wherein the enzyme is selected from the group consisting of alkaline phosphatases, penicillin amidases, arylsulfatases, cytosine deaminases, proteases, D-alanyl carboxypeptidases, carbohydrate-cleaving enzymes and β-lactamases.

5. The method of claim 1, wherein the enzyme is alkaline phosphatase.

6. The method of claim 1, wherein the enzyme is a penicillin V amidase.

7. The method of claim 1, wherein the enzyme is cytosine deaminase.

8. The method of claim 1, wherein the parent drug is selected from the group consisting of etoposide, teniposide, adriamycin, daunomycin, carminomycin, aminopterin, dactinomycin, mitomycins, cis-platinum and cis-platinum analogues, bleomycins, esperamicins, 5-fluorouracil, melphalan and other nitrogen mustards.

9. The method of claim 1, wherein the parent drug is etoposide.

10. The method of claim 1, wherein the parent drug is a mitomycin.

11. The method of claim 1, wherein the parent drug is adriamycin.

12. The method of claim 1, wherein the parent drug is 5-fluorouracil.

13. The method of claim 1, wherein the prodrug is selected from the group consisting of phosphate-containing prodrugs, sulfate-containing prodrugs, peptide-containing prodrugs, glycosylated prodrugs, β-lactam-containing prodrugs, D-amino acid-modified prodrugs, phenoxyacetamide-containing prodrugs or substituted-phenoxyacetamide-containing prodrugs, and phenylacetamide-containing prodrugs or substituted-phenylacetamide-containing prodrugs.

14. The method of claim 1, wherein the prodrug is selected from the group consisting of etoposide phosphates, etoposide thiophosphates, etoposide sulfates, teniposide phosphates, teniposide thiophosphates, teniposide sulfates, adriamycin phosphates, adriamycin sulfates, $N^7$-$C_{1-8}$ alkyl mitomycin phosphates and $N^7$-$C_{1-8}$alkyl mitomycin sulfates.

15. The method of claim 1, wherein the prodrug is etoposide-4'-phosphate or a pharmaceutically acceptable salt thereof.

16. The method of claim 1, wherein the prodrug is 7-(2'-aminoethylphosphate)mitomycin or a pharmaceutically acceptable salt thereof.

17. The method of claim 1, wherein the prodrug is selected from the group consisting of N-(p-hydroxyphenoxyacetyl) adriamycin, N-(phenoxyacetyl)adriamycin, N-(p-hydroxyphenylacetyl)adriamycin and N-(phenylacetyl)adriamycin.

18. The method of claim 1, wherein the prodrug is selected from the group consisting of 5-fluorouridine monophosphate and 5-fluorocytosine.

19. The method of claim 1, wherein the antibody-enzyme conjugate is L6-AP.

20. The method of claim 1, wherein the antibody-enzyme conjugate is 96.5-AP.

21. The method of claim 1, wherein the antibody-enzyme conjugate is 1F5-AP.

22. The method of claim 1, wherein the antibody-enzyme conjugate is L6-PVA.

23. The method of claim 1, wherein the antibody-enzyme conjugate is 1F5-PVA.

24. The method of claim 1, wherein the antibody-enzyme conjugate is L6-CD.

25. The method of claim 1, wherein the antibody-enzyme conjugate is 1F5-CD.

26. The method of claim 1, wherein the antibody-enzyme conjugate is L6-AP and the prodrug is etoposide-4'-phosphate, $N^7$-$C_{1-8}$ alkyl mitomycin phosphate or pharmaceutically acceptable salts thereof.

27. The method of claim 1, wherein the antibody-enzyme conjugate is L6-PVA and the prodrug is selected from the group consisting of N-(p-hydroxyphenoxyacetyl)adriamycin and N-(phenoxyacetyl)adriamycin.

28. The method of claim 1, wherein the antibody-enzyme conjugate is L6-CD and the prodrug is 5-fluorocytosine.

29. The method of claim 1, wherein the tumor cells are of an origin selected from the group consisting of carcinomas, melanomas, lymphomas, and bone and soft tissue sarcomas.

30. A method for the delivery of a combination of cytotoxic agents to tumor cells comprising: the administration of an effective amount of an antibody-enzyme conjugate comprising an antibody reactive with an antigen on the surface of said tumor cells conjugated to an enzyme which converts more than one prodrug, each of which is weakly cytotoxic to tumor cells compared to its corresponding parent drug, into the more cytotoxic parent drug, and the administration of an effective amount of more than one of said prodrugs.

31. The method of claim 1, wherein the enzyme is selected from the group consisting of alkaline phosphatases, penicillin amidases, arylsulfatases, cytosine deaminases, proteases, D-alanyl carboxypeptidases, carbohydrate-cleaving enzymes and β-lactamases.

32. The method of claim 31, wherein the enzyme is alkaline phosphatase.

33. The method of claim 30, wherein the parent drug is selected from the group consisting of etoposide, teniposide, adriamycin, daunomycin, carminomycin, aminopterin, dactinomycin, mitomycins, cis-platinum and cis-platinum analogues, bleomycins, esperamicins, 5-fluorouracil, melphalan and other nitrogen mustards.

34. The method of claim 30, wherein the prodrugs are selected from the group consisting of phosphate-containing prodrugs, sulfate-containing prodrugs, peptide-containing prodrugs, glycosylated prodrugs, β-lactam-containing prodrugs, D-amino acid-modified prodrugs, phenoxyacetamide-containing prodrugs or substituted-phenoxyacetamide-containing prodrugs, and phenylacetamide-containing prodrugs or substituted-phenylacetamide-containing prodrugs.

35. The method of claim 30, wherein the prodrugs are selected from the group consisting of etoposide phosphates, etoposide thiophosphates, etoposide sulfates, teniposide phosphates, teniposide thiophosphates, teniposide sulfates, adriamycin phosphate, adriamycin sulfates, N-phenoxyacetyl derivatives of adriamycin, N-phenylacetyl derivatives of adriamycin, $N^7$-$C_{1-8}$ alkyl mitomycin phosphates and $N^7$-$C_{1-8}$ alkyl mitomycin sulfates.

36. The method of claim 30, wherein one of the prodrugs is 5-fluorocytosine or 5-fluorouridine monophosphate.

37. The method of claim 30, wherein the prodrugs are etoposide-4'-phosphate, $N^7$-$C_{1-8}$ alkyl mitomycin phosphate or pharmaceutically acceptable salts thereof.

38. The method of claim 30, wherein the antibody-enzyme conjugate is selected from the group consisting of L6-AP, 96.5-AP, and 1F5-AP.

39. The method of claim 30, wherein the antibody-enzyme conjugate is L6-AP and the prodrugs are etoposide-4'-phosphate and $N^7$-$C_{1-8}$ alkyl mitomycin phosphate or pharmaceutically acceptable salts thereof.

40. A method for the delivery of a combination of cytotoxic agents to tumor cells comprising: the administration of an effective amount of more than one antibody-enzyme conjugate, wherein the antibody of each conjugate is reactive with the same or a different antigen located on the surface of said tumor cells and the enzyme of each conjugate is the same or different and which converts at least one prodrug, that is weakly cytotoxic to tumor cells compared to its corresponding parent drug, into the more cytotoxic parent drug, and the administration of an effective amount of said prodrug or prodrugs.

41. The antibody-enzyme conjugate, L6-AP.
42. The antibody-enzyme conjugate, 96.5-AP.
43. The antibody-enzyme conjugate, 1F5-AP.
44. The antibody-enzyme conjugate, L6-PVA.
45. The antibody-enzyme conjugate, 1F5-PVA.
46. The antibody-enzyme conjugate, L6-CD.
47. The antibody-enzyme conjugate, 1F5-CD.
48. A compound having the formula:

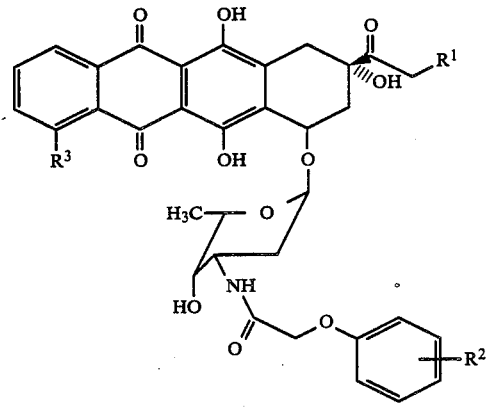

wherein:
$R^1$ is H, and $R^3$ is OH or $OCH_3$; or
$R^1$ is OH and $R^3$ is $OCH_3$; and
$R^2$ is H or OH.

49. A compound having the formula:

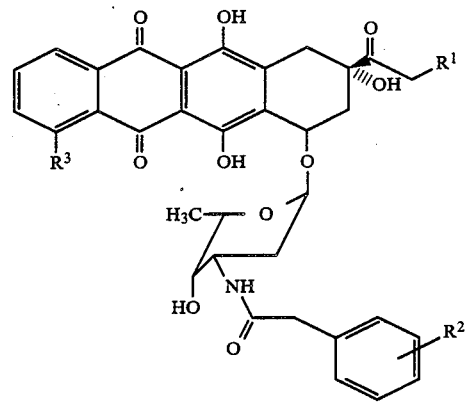

wherein:
$R^1$ is H, and $R^3$ is OH or $OCH_3$; or
$R^1$ is OH and $R^3$ is $OCH_3$; and
$R^2$ is H or OH.

50. N-(p-hydroxyphenoxyacetyl)adriamycin.
51. N-(phenoxyacetyl)adriamycin.
52. A pharmaceutically acceptable composition useful in the treatment of tumors which comprises a pharmaceutically effective amount of at least one antibody-enzyme conjugate according to claim 1.

53. A combination of at least one antibody-enzyme conjugate according to claim 1 and at least one prodrug that is weakly cytotoxic to tumor cells compared to its corresponding parent drug.

54. The combination of claim 53, wherein the antibody-enzyme conjugate is selected from the group consisting of L6-AP, L6-PVA and L6-CD.

55. The combination of claim 53, wherein the prodrug is selected from the group consisting of phosphate-containing prodrugs, sulfate-containing prodrugs, peptide-containing prodrugs, glycosylated prodrugs, β-lactam-containing prodrugs, D-amino acid-modified prodrugs, phenoxyacetamide-containing prodrugs or substituted-phenoxyacetamide-containing prodrugs, and phenylacetamide-containing prodrugs or substituted-phenylacetamide-containing prodrugs.

56. The combination of claim 53, wherein the prodrug is selected from the group consisting of etoposide phosphates, etoposide thiophosphates, etoposide sulfates, teniposide phosphates, teniposide thiophosphates, teniposide sulfates, adriamycin phosphates, adriamycin sulfates, N-phenoxyacetyl derivatives of adriamycin, N-phenylacetyl derivatives of adriamycin, mitomycin phosphates, mitomycin sulfates, 5-fluorouridine monophosphate and 5-fluorocytosine.

57. The combination of claim 53, wherein the antibody-enzyme conjugate is L6-AP and the prodrug is etoposide-4'-phosphate, $N^7$-$C_{1-8}$ alkyl mitomycin phosphate or pharmaceutically acceptable salts thereof.

58. A method for treating mammalian tumors comprising the step of administering to a mammal a pharmaceutically effective amount of at least one antibody-enzyme conjugate according to claim 1 and a pharmaceutically effective amount of at least one prodrug according to claim 1.

59. The method of claim 58, wherein the prodrug is selected from the group consisting of phosphate-containing prodrugs, sulfate-containing prodrugs, peptide-containing prodrugs, glycosylated prodrugs, β-lactam-containing prodrugs, D-amino acid-modified prodrugs, phenoxyacetamide-containing prodrugs or substituted-phenoxyacetamide-containing prodrugs, and phenylacetamide-containing prodrugs or substituted-phenylacetamide-containing prodrugs.

60. The method of claim 58, wherein the prodrug is selected from the group consisting of 5-fluorouridine monophosphate and 5-fluorocytosine.

61. The method of claim 58, wherein the antibody-enzyme conjugate is L6-AP and the prodrug is etoposide-4'-phosphate, $N^7$-$C_{1-8}$ alkyl mitomycin phosphate or pharmaceutically acceptable salts thereof.

62. A method for the delivery of cytotoxic agents to tumor cells comprising: the administration of an effective amount of at least one fusion protein comprising at least the antigen binding region of an antibody reactive with a tumor-associated antigen linked to at least a functionally active portion of an enzyme which converts at least one weakly cytotoxic prodrug into its more cytotoxic parent drug, and the administration of an effective amount of said prodrug.

63. The method of claim 62, wherein the antibody is selected from the group consisting of monoclonal antibodies L6, 96.5 and 1F5.

64. The method of claim 62, wherein the enzyme is selected from the group consisting of alkaline phosphatases, penicillin amidases, aryl sulfatases, cytosine deaminases, proteases, D-alanyl carboxypeptidases, carbohydrate-cleaving enzymes and β-lactamases.

* * * * *